United States Patent
Coates et al.

(10) Patent No.: US 8,710,283 B2
(45) Date of Patent: Apr. 29, 2014

(54) ISOSELECTIVE POLYMERIZATION OF EPOXIDES

(71) Applicant: Cornell University, Ithaca, NY (US)

(72) Inventors: Geoffrey W. Coates, Lansing, NY (US); Wataru Hirahata, Sodegaura (JP)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/624,187

(22) Filed: Sep. 21, 2012

(65) Prior Publication Data
US 2013/0079491 A1 Mar. 28, 2013

Related U.S. Application Data

(60) Division of application No. 12/706,077, which is a continuation of application No. PCT/US2008/073530, filed on Aug. 18, 2008, now abandoned.

(60) Provisional application No. 60/935,529, filed on Aug. 17, 2007.

(51) Int. Cl.
*C07C 25/00* (2006.01)

(52) U.S. Cl.
USPC ........... 570/183; 570/187; 502/107; 528/409; 528/412; 556/34

(58) Field of Classification Search
USPC ........... 570/183, 187; 502/109; 528/409, 412; 566/34
See application file for complete search history.

(56) References Cited

U.S. PATENT DOCUMENTS

| | | | |
|---|---|---|---|
| 6,465,594 B1 | 10/2002 | Tamao et al. | |
| 7,399,822 B2 | 7/2008 | Coates et al. | |
| 8,026,317 B2 | 9/2011 | Coates et al. | |
| 2009/0030172 A1* | 1/2009 | Zheng et al. | 528/271 |

FOREIGN PATENT DOCUMENTS

WO WO-09026261 A2 2/2009

OTHER PUBLICATIONS

Campbell et al., "Unsymmetrical salen-type ligands: high yield synthesis of salen-type Schiff bases containing two different benzaldehyde moieties," Tetrahedron Letters, 42: 1221-1225, 2001.
Coates et al., "Discrete Metal-Based Catalysts for the Copolymerization of CO2 and Epoxides: Discovery, Reactivity, Optimization, and Mechanism," Angewandte Chemie International Edition, 43(48); 6618-6639, 2004.
Grove et al., "Crystalline products isolated from solutions with commercially available 2,3-bis(2-pyridyl)pyrazine (dpp) as reactant: Detection of a dimerized form of dpp," Journal of Molecular Structure, 800: 1-7, 2006.
Hirahata et al., "Enantioselective Polymerization of Epoxides: A Highly Active and Selective Catalyst for the Preparation of Stereoregular Polyethers and Enantiopure Epoxides," J. Am. Chem. Soc., 130: 17658-17659, 2008.

(Continued)

*Primary Examiner* — Shane Fang
(74) *Attorney, Agent, or Firm* — Choate Hall & Stewart LLP; Charles E. Lyon

(57) ABSTRACT

The present invention provides novel bimetallic complexes and methods of using the same in the isoselective polymerization of epoxides. The invention also provides methods of kinetic resolution of epoxides. The invention further provides polyethers with high enantiomeric excess that are useful in applications ranging from consumer goods to materials.

47 Claims, 27 Drawing Sheets

(56) References Cited

OTHER PUBLICATIONS

Inoue et al., "Preparation of Optically Active Poly (propylene oxide) by Asymmetric Induction," Makromolekulare Chemie, 53: 215-218, 1962.

International Preliminary Report on Patentability (3 pages.), mailed Mar. 17, 2009.

International Search Report for PCT/US08/073530, mailed Mar. 17, 2009.

Kozitsyna et al., "Oxidative esterification of alkenes via π- and σ-organopalladium complexes: new pathways for the reaction," Journal of Organometallic Chemistry, 636: 69-75, 2001.

Nielsen et al., "Mechanistic Investigation Leads to a Synthetic Improvement in the Hydrolytic Kinetic Resolution of Terminal Epoxides," J. Am. Chem. Soc., 126: 1360-1362, 2004.

Peretti et al., "A Highly Active, Isospecific Cobalt Catalyst for Propylene Oxide Polymerization," J. Am. Chem. Soc., 127: 11566-11567, 2005.

Ready et al., "Highly Active Oligomeric (salen) Co Catalysts for Asymmetric Epoxide Ring-Opening Reactions," J. Am. Chem. Soc., 123: 2687-2688, 2001.

Schaus et al., "Highly Selective Hydrolytic Kinetic Resolution of Terminal Epoxides Catalyzed by Chiral (salen) Co Complexes. Practical Synthesis of Enantioenriched Terminal Epoxides and 1,2-Diols," J. Am. Chem. Soc., 124(7): 1307-1315.

Schilling et al., "Carbon-13 NMR Determination of Poly (propylene oxide) Microstructure," Macromolecules, 19: 1337-1343, 1986.

Tsuruta et al., "Resolution of DL-Propylene Oxide by Asymmetric-induced Polymerization," Makromolekulare Chemie, 55: 230-231, 1962.

Ugur et al., "Stereoregularity of Fractionally Crystallized Poly(propylene Oxide) Samples by C-NMR Spectroscopy," Journal of Polymer Science: Part A: Polymer Chemistry, 27: 1749-1761, 1989.

Written Opinion for PCT/US08/073530 (5 pages, mailed Mar. 17, 2009.

Zhang et al., "Biaryl-Based Macrocyclic and Polymeric Chiral (Salophen) Ni (II) Complexes: Synthesis and Spectroscopic Study," J. Org. Chem., 66: 481-487, 2001.

\* cited by examiner (a)

(b)

(a)

(b)

(a)

(b)

ISOSELECTIVE POLYMERIZATION OF EPOXIDES

CROSS REFERENCE TO RELATED APPLICATIONS

The present application is a divisional of U.S. Utility patent application Ser. No. 12/706,077 filed Feb. 16, 2010, which is a continuation of International Patent Application No. PCT/US08/73530, filed Aug. 18, 2008, which claims priority to U.S. Provisional Patent Application Ser. No. 60/935,529, filed Aug. 17, 2007, the entirety of each of which is hereby incorporated by reference.

BACKGROUND OF THE INVENTION

Enantiomerically pure polymers are valuable due to their optically active properties for uses ranging from materials science to synthetic organic chemistry. These polymers can be prepared by the polymerization of enantiomerically pure monomers. However, most enantiomerically pure monomers are difficult and/or expensive to prepare compared to their racemic counterparts, such that polymerization of enantiometically pure monomers is not a realistic option.

Some efforts have been made to develop enantioselective methods for preparing enantiomerically pure polymers. Specifically, Furukawa and co-workers (Tsuruta, Teiji; Inoue, Shohei; Yoshida, Norimasa; Furukawa, Junji., Makromolekulare Chemie (1962), 55, 230-1; Inoue, Shohei; Tsuruta, Teiji; Furukawa, Junji., Makromol (1962), 215-18) have described the enantioselective polymerization of racemic propylene oxide (PO) with catalysts consisting of $ZnEt_2$ and enantiomerically pure alcohols such as (+)-borneol. This system produces optically active crystalline poly(PO) and enantio-enriched PO with a selectivity factor ($k_{rel}=k_{fast}/k_{slow}$) of 1.5. Since this discovery, numerous combinations of alkyl metals and chiral alcohols have been evaluated for the enantioselective polymerization of PO. However, no catalyst has been identified that demonstrates high enantioselectivity in this reaction.

SUMMARY OF THE INVENTION

The present invention encompasses the recognition that the isoselective polymerization of epoxides is useful for providing isotactic or enantiopure polyethers. In certain embodiments, the present invention provides bimetallic complexes for the isoselective polymerization of epoxides.

According to one aspect, the present disclosure provides a bimetallic complex of formula I:

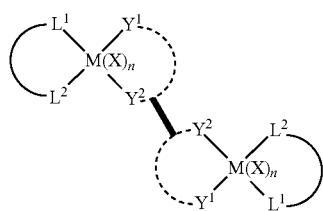

wherein:
M is a metal atom;
X is a nucleophile;
n is an integer from 0 to 2, inclusive each occurrence of $L^1$, $L^2$, $Y^1$, and $Y^2$ is independently —O—, —P(R')$_2$—, =NR'—, or —N(R')$_2$—;
each occurrence of

is an optionally substituted moiety selected from the group consisting of $C_{2-12}$ aliphatic, $C_{7-12}$ arylalkyl; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;
each occurrence of

is an optionally substituted moiety selected from the group consisting of $C_{7-12}$ arylalkyl; 6-10-membered aryl; and 5-10-membered heteroaryl having 1-4 heteroatoms independently selected from nitrogen, oxygen, or sulfur;

⟍ represents a single bond directly attached to an aryl or heteroaryl ring of each

each occurrence of R' is hydrogen or an optionally substituted moiety selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—; or
two R' are taken together with their intervening atoms to form a monocyclic or bicyclic 5-12-membered ring;
wherein a substituent may comprise one or more organic cations; and
each occurrence of R$^y$ is independently hydrogen or an optionally substituted $C_{1-6}$ aliphatic group.

According to one aspect, the present invention provides a polymer of formula:

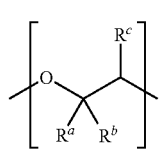

wherein:
R$^a$ is an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and each of $R^b$ and $R^c$ is independently hydrogen or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and wherein any of ($R^a$ and $R^c$), ($R^b$ and $R^c$), and ($R^a$ and $R^b$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

According to one aspect, the present invention provides a method of polymerization, the method comprising:

a) providing a prochiral epoxide of formula:

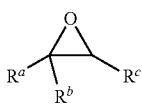

wherein:

$R^a$ is an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and each of $R^b$ and $R^c$ is independently hydrogen or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

wherein any of ($R^a$ and $R^c$), ($R^b$ and $R^c$), and ($R^a$ and $R^b$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl;

and b) treating the epoxide with a bimetallic catalyst under suitable conditions to form a polymer of formula:

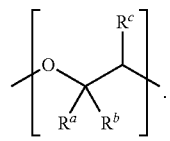

In certain embodiments, the method further comprises the step of recovering unreacted epoxide, wherein the recovered epoxide is enantiomerically enriched.

According to one aspect, the present disclosure provides materials suitable for food packaging, electronics, consumer goods, chiral chromatographic media, polymeric reagents, and polymeric catalysts, the materials comprising a provided polymer as described herein. In certain embodiments, the material is oil resistant. In certain embodiments, the material is a film. In some embodiments, the material is extruded. In some embodiments, the material is thermoformed.

DEFINITIONS

Figure 1:
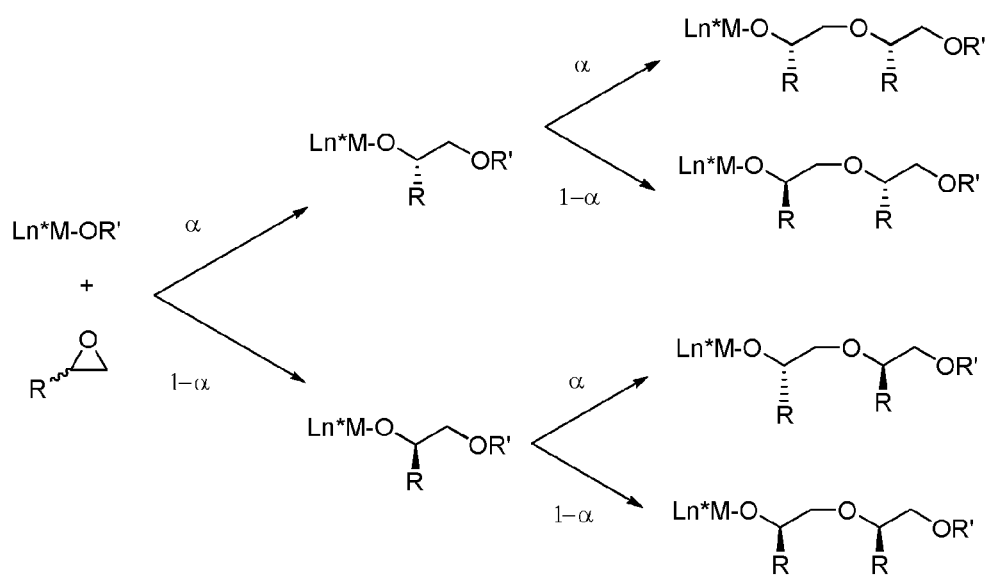
FIG. 1 depicts the a parameter of an enantiopure catalyst.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "axial chirality", refers to chirality in which a molecule, or a portion thereof, does not possess a stereogenic center but has an axis of chirality about which a set of substituents is held in a spatial arrangement that is not superimposable on its minor image. Axial chirality may be observed, for example, in atropisomeric biaryl compounds where the rotation about the aryl-aryl bond is restricted. It will be appreciated that a compound of the present invention may possess axial chirality whether or not other stereogenic centers are present elsewhere in the molecule.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "epoxide", as used herein, refers to a substituted oxirane. Such substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted.

Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}$—$CH(OR^\circ)_2$; —$(CH_2)_{0-4}SR^\circ$; —$(CH_2)_{0-4}$ Ph, which may be substituted with $R^\circ$; —$(CH_2)_{0-4}$ $O(CH_2)_{0-1}$ Ph which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)N(R^\circ)_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)RO_2$; —$OP(O)RO_2$; —$OP(O)(OR^\circ)_2$; $SiR^\circ_3$; —$(C_{1-4}$ straight or branched)alkylene)O—$N(RO)_2$; or —$(C_{1-4}$ straight or branched)alkylene)C(O)O—$N(R^\circ)_2$, wherein each $R^\circ$ may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}$ $CH(OR^\bullet)_2$; —$P(haloR^\bullet)$, —CN, —$N_3$, —$(CH_2)_{0-2}$ $C(O)R^\bullet$, —$(CH_2)_{0-2}C(O)OH$, —$(CH_2)_{0-2}C(O)OR^\bullet$, —$(CH_2)_{0-4}$ $C(O)N(R^\circ)_2$; —$(CH_2)_{0-2}SR^\bullet$, —$(CH_2)_{0-2}SH$, —$(CH_2)_{0-2}$ $NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*)_2)_{2-3}O$—, or —$S(C(R^*)_2)_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^*$), —CN, —$C(O)OH$, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. A substitutable nitrogen may be substituted with three $R^\dagger$ substituents to provide a charged ammonium moiety —N⁺(R†)₃, wherein the ammonium moiety is further complexed with a suitable counterion.

Suitable substituents on the aliphatic group of R† are independently halogen, —R●, —(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently $C_1$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate and/or extent of a chemical reaction, while not being consumed or undergoing a permanent chemical change itself.

As used herein, the term "tetravalent" refers to metal centers having four permanent contact points with other atoms of a bimetallic complex. The tetravalent descriptor is exclusive of other initiators, nucleophiles, solvent molecules, or counterions that may form additional contact points with a metal center.

DETAILED DESCRIPTION OF CERTAIN EMBODIMENTS

The present invention provides novel isotactic polyethers that are useful in a variety of applications ranging from consumer packaging to materials. It has been unexpectedly found that the use of a non-racemic bimetallic complex as described herein affords polyethers of high isotacticity. In certain embodiments, the present invention provides methods of using a provided bimetallic complex to afford novel polyethers. In certain embodiments, the present invention provides methods of using a provided bimetallic complex to achieve kinetic resolution of epoxides.

I. Bimetallic Complexes

As generally described above, the present invention provides bimetallic complexes useful for polymerization of epoxides. In certain embodiments, the bimetallic complex is of formula I:

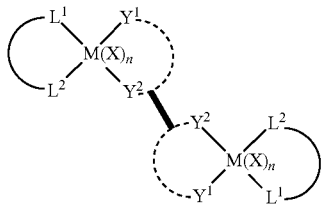

I wherein:
M is a metal atom;
X is a nucleophile;
n is an integer from 0 to 2, inclusive
each occurrence of $L^1$, $L^2$, $Y^1$, and $Y^2$ is independently —O—, —P(R')₂—, =NR'—, or —N(R')₂—;
each occurrence of

is an optionally substituted moiety selected from the group consisting of $C_{2-12}$ aliphatic, $C_{7-12}$ arylalkyl; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

each occurrence of

is an optionally substituted moiety selected from the group consisting of $C_{7-12}$ arylalkyl; 6-10-membered aryl; and 5-10-membered heteroaryl having 1-4 heteroatoms independently selected from nitrogen, oxygen, or sulfur;

↘ represents a single bond directly attached to an aryl or heteroaryl ring of each

each occurrence of R' is hydrogen or an optionally substituted moiety selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR^y—, —N(R^y)C(O)—, —C(O)N(R^y)—, —OC(O)N(R^y)—, —N(R^y)C(O)O—, —OC(O)O—, —O—, —C(O)—, —OC(O)—, —C(O)O—, —S—, —SO—, —SO₂—, —C(=S)—, —C(=NR^y)—, —C(=NOR^y)— or —N=N—; or two R' are taken together with their intervening atoms to form a monocyclic or bicyclic 3-12-membered ring; wherein a substituent may comprise one or more organic cations; and each occurrence of R^y is independently hydrogen or an optionally substituted $C_{1-6}$ aliphatic group.

In certain embodiments, M is a main group metal. In certain embodiments, M is a transition metal selected from the periodic table groups 5-12, inclusive, boron, or aluminum. In certain embodiments, M is a transition metal selected from the periodic table groups 4-11, inclusive. In certain embodiments, M is selected from the lanthanides. In certain embodiments, M is a transition metal selected from the periodic table groups 5-10, inclusive. In certain embodiments, M is a transition metal selected from the periodic table groups 7-9, inclusive. In some embodiments, M is selected from the group consisting of Cr, Mn, V, Fe, Co, Mo, W, Ru, Ti, Al, Zr, Hf, and Ni.

In certain embodiments, the bimetallic complex employed is a zinc, cobalt, chromium, aluminum, titanium, ruthenium or manganese complex. In certain embodiments, the bimetallic complex is an aluminum complex. In certain embodiments, the bimetallic complex is a chromium complex. In certain embodiments, the bimetallic complex is a zinc complex. In certain embodiments, the bimetallic complex is a titanium complex. In certain embodiments, the bimetallic complex is a ruthenium complex. In certain embodiments, the bimetallic complex is a manganese complex. In certain embodiments, the bimetallic complex is cobalt complex. In certain embodiments, wherein the bimetallic complex is a cobalt complex, the cobalt metal has a valency of +3 (i.e., Co(III)). In certain embodiments, the bimetallic complex comprises two tetradentate ligands. In certain embodiments the bimetallic complex comprises a Schiff base. In certain embodiments the bimetallic complex comprises a salen ligand, or a beta diimidate ligand.

As described above, X is a nucleophile or counterion. Consistent with our earlier disclosure of bimetallic catalysts in U.S. Provisional Patent Application Ser. No. 60/935,529, filed Aug. 17, 2007, we have now shown that X may be present in a variety of embodiments, the details of which are disclosed herein. In certain embodiments, when n is 0, X is absent. In certain embodiments, X is a nucleophilic ligand. Exemplary nucleophilic ligands include, but are not limited to, —$OR^2$, —$SR^x$, —$O(C\!=\!O)R^x$, —$O(C\!=\!O)OR^x$, —$O(C\!=\!O)N(R^x)_2$, —$N(R^x)(C\!=\!O)R^x$, —NC, —CN, halo (e.g., —Br, —I, —Cl), —$N_3$, —$O(SO_2)R^x$ and —$OPR^x_3$, wherein each $R^x$ is, independently, selected from hydrogen, optionally substituted aliphatic, optionally substituted heteroaliphatic, optionally substituted aryl and optionally substituted heteroaryl.

In certain embodiments, X is —$O(C\!=\!O)R^x$, wherein $R^x$ is selected from optionally substituted aliphatic, fluorinated aliphatic, optionally substituted heteroaliphatic, optionally substituted aryl, fluorinated aryl, and optionally substituted heteroaryl.

For example, in certain embodiments, X is —$O(C\!=\!O)R^x$, wherein $R^x$ is optionally substituted aliphatic. In certain embodiments, X is —$O(C\!=\!O)R^x$, wherein $R^x$ is optionally substituted alkyl and fluoroalkyl. In certain embodiments, X is —$O(C\!=\!O)CH_3$ or —$O(C\!=\!O)CF_3$.

Furthermore, in certain embodiments, X is —$O(C\!=\!O)R^x$, wherein $R^x$ is optionally substituted aryl, fluoroaryl, or heteroaryl. In certain embodiments, X is —$O(C\!=\!O)R^x$, wherein $R^x$ is optionally substituted aryl. In certain embodiments, X is —$O(C\!=\!O)R^x$, wherein $R^x$ is optionally substituted phenyl. In certain embodiments, X is —$O(C\!=\!O)C_6H_5$ or —$O(C\!=\!O)C_6F_5$.

In certain embodiments, X is —$OR^x$, wherein $R^x$ is selected from optionally substituted aliphatic, optionally substituted heteroaliphatic, optionally substituted aryl, and optionally substituted heteroaryl.

For example, in certain embodiments, X is —$OR^x$, wherein $R^x$ is optionally substituted aryl. In certain embodiments, X is —$OR^x$, wherein $R^x$ is optionally substituted phenyl. In certain embodiments, X is —$OC_6H_5$ or —$OC_6H_2(2,4\text{-}NO_2)$.

In certain embodiments, X is halo. In certain embodiments, X is —Br. In certain embodiments, X is —Cl. In certain embodiments, X is —I.

In certain embodiments, X is —$O(SO_2)R^x$. In certain embodiments X is —OTs. In certain embodiments X is —$OSO_2Me$. In certain embodiments X is —$OSO_2CF_3$. In some embodiments, X is a 2,4-dinitrophenolate anion.

In some embodiments, n is 0. In some embodiments, n is 1. In some embodiments, n is 2.

In some embodiments, each occurrence of $L^1$ is independently —O— or —NR'—. In some embodiments, each occurrence of $L^2$ is independently —O— or —NR'—. In some embodiments, each occurrence of $Y^1$ is independently —O— or —NR'—. In some embodiments, each occurrence of $Y^2$ is independently —O— or —NR'—. In certain embodiments, $L^1$ and $Y^1$ are both —NR'—. In certain embodiments, $L^2$ and $Y^2$ are both —O—.

In some embodiments, each occurrence of R' is independently an optionally substituted group selected from $C_{1-12}$ aliphatic or $C_{1-12}$ heteroaliphatic having 1-4 heteroatoms independently selected from the group consisting of nitrogen, oxygen, and sulfur. In certain embodiments, each occurrence of R' is independently an optionally substituted $C_{1-12}$ aliphatic group. In certain embodiments, each occurrence of R' is independently an optionally substituted $C_{1-12}$ heteroaliphatic group having 1-4 heteroatoms independently selected from the group consisting of nitrogen, oxygen, and sulfur.

In some embodiments, two R' are taken together with their intervening atoms to form a monocyclic or bicyclic 5-12-membered ring. In some embodiments, two R' are taken together with their intervening atoms to form an optionally substituted bicyclic 5-10-membered ring. In some embodiments, two R' are taken together with their intervening atoms to form:

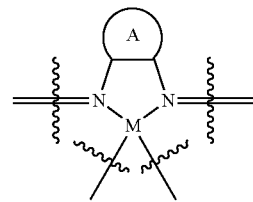

wherein Ring A is optionally substituted with one or more halogen or R° groups. In some embodiments, two R' are taken together with their intervening atoms to form:

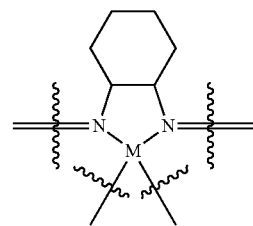

In some embodiments, each occurrence of

is independently an optionally substituted $C_{7-12}$ arylalkyl group. In some embodiments, each occurrence of

is independently an optionally substituted 6-10-membered aryl group. In some embodiments, each occurrence of

is independently an optionally substituted 5-10-membered heteroaryl group having 1-4 heteroatoms independently selected from nitrogen, oxygen, or sulfur. In some embodiments, each occurrence of

is independently an optionally substituted 4-7-membered heterocyclic group having 1-2 heteroatoms independently selected from the group consisting of nitrogen, oxygen, and sulfur group. In some embodiments,

is an optionally substituted $C_7$ arylalkyl group. In some embodiments,

comprises a salen ligand.

In some embodiments, each occurrence of

is independently an optionally substituted $C_{7-12}$ arylalkyl group. In some embodiments, each occurrence of

is independently an optionally substituted 6-10-membered aryl group. In some embodiments, each occurrence of

is independently an optionally substituted 5-10-membered heteroaryl group having 1-4 heteroatoms independently selected from nitrogen, oxygen, or sulfur. In some embodiments, each occurrence of

is independently an optionally substituted 4-7-membered heterocyclic group having 1-2 heteroatoms independently selected from the group consisting of nitrogen, oxygen, and sulfur group. In some embodiments,

is an optionally substituted $C_7$ arylalkyl group. In some embodiments,

comprises a salen ligand.

In certain embodiments, the $L^1, Y^2, Y^1, Y^2$ and

moieties are such that the bimetallic complex is non-symmetric. In certain embodiments, the $L^1, L^2, Y^1, Y^2$ and

moieties are such that the bimetallic complex is non-racemic. In certain embodiments, the $L^1, L^2, Y^1, Y^2$ and

moieties are such that the bimetallic complex has an axial symmetry.

In certain embodiments, provided bimetallic complexes are tetradentate with respect to the number of atoms forming covalent bonds with each M. Such tetracoordinate metal centers may further form bonding interactions with one or more X moieties or solvent molecules.

In certain embodiments, provided bimetallic complexes contain an element having axial chirality. In some embodiments, the element having axial chirality is contained in the portion of formula I having the formula:

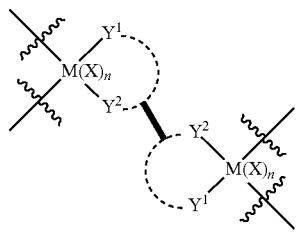

wherein each of

, n, X, $Y^1$, $Y^2$, and M is as defined in formula I and described in classes and subclasses above and herein.

In some embodiments, the axial chirality of a bimetallic complex of formula I results from the hindered rotation of the molecule about bond B1 indicated in the formula:

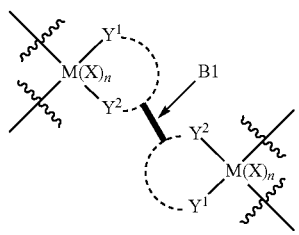

wherein each of

$\diagdown$, n, X, $Y^1$, $Y^2$, and M is as defined in formula I and described in classes and subclasses above and herein.

In certain embodiments, the present invention provides an optically enriched bimetallic complex of formula I. In some embodiments, the bimetallic complex has an enantiomeric excess greater than 90%. In some embodiments, the bimetallic complex has an enantiomeric excess greater than 95%. In some embodiments, the bimetallic complex has an enantiomeric excess greater than 97%. In some embodiments, the bimetallic complex has an enantiomeric excess greater than 98%. In some embodiments, the bimetallic complex has an enantiomeric excess greater than 99%. In certain embodiments, the bimetallic complex is optically pure.

As described above, each occurrence of $L^1$, $L^2$, $Y^1$, and $Y^2$ is independently —O—, —P(R')$_2$—, =NR'—, or —N(R')$_2$—. In certain embodiments, an R' group of $L^1$ may be taken together with a R' group of $Y^1$ to form a monocyclic or bicyclic 3-12-membered ring. In certain embodiments, an R' group of $L^2$ may be taken together with a R' group of $Y^2$ to form a monocyclic or bicyclic 3-12-membered ring. In certain embodiments, the two R' groups are taken together with their intervening atoms to form an optionally substituted moiety selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—; wherein each occurrence of R$^y$ is independently hydrogen or an optionally substituted $C_{1-6}$ aliphatic group.

As shown in formula I, $L^1$, $L^2$, $Y^1$, $Y^2$, and optionally X form shared-electron bonding interactions with M. It will be appreciated by one of ordinary skill in the art that for the —O—, —P(R')$_2$—, =NR'—, or —N(R')$_2$— groups of $L^1$, $L^2$, $Y^1$, and $Y^2$, the atoms interacting with the metal center are O, P, and/or N. It will further be appreciated that the number and identity of R' groups on the O, P, and N atoms of $L^1$, $L^2$, $Y^1$, $Y^2$ will be such that valency rules are satisfied when a metal atom is present. In certain embodiments, each occurrence of $L^1$, $L^2$, $Y^1$, and $Y^2$ is independently —O—, —PR'—, =N—, or —NR'—.

In some embodiments, two M moieties of the same bimetallic complex are not directly connected via an —O— linkage. In some embodiments, two M moieties of the same bimetallic complex are not directly connected via one or more X groups.

In certain embodiments, provided bimetallic complexes are of formula I-a:

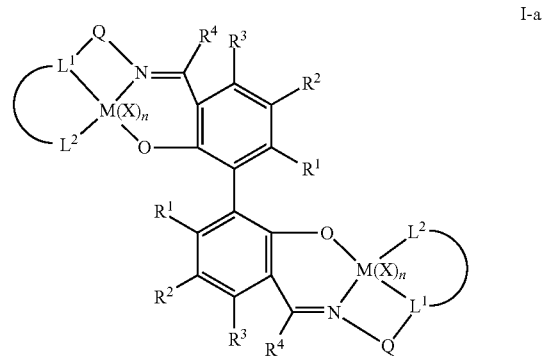

I-a wherein:
each of

n, X, M, $L^1$, and $L^2$ is as defined in formula I and described in classes and subclasses above and herein;
each occurrence of Q is an optionally substituted moiety selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—;
each occurrence of R$^y$ is independently hydrogen or an optionally substituted $C_{1-6}$ aliphatic group;
each occurrence of $R^1$ and $R^2$ is independently hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; or
$R^1$ and $R^2$ are taken together with their intervening atoms to form an optionally substituted 4-14-membered carbocycle, an optionally substituted 4-14-membered heterocycle, an optionally substituted 6-10-membered aryl group or an optionally substituted 5-10-membered heteroaryl group having 1-4 heteroatoms independently selected from nitrogen, oxygen, or sulfur ring; and
each occurrence of $R^3$ and $R^4$ is independently hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

Consistent with our earlier disclosure, Q may be present in a variety of embodiments, the details of which are disclosed herein. In certain embodiments, each occurrence of Q is independently is an optionally substituted moiety selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—. In certain embodiments, Q is an optionally substituted C$_3$-C$_{14}$ heterocyclic group. In some embodiments, Q is an optionally substituted C$_5$-C$_{10}$ heteroaryl group.

In certain embodiments, each occurrence of Q is independently an optionally substituted C$_3$-C$_{14}$ carbocycle aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—. In some embodiments, Q is 1,2-cyclohexyl. In some embodiments, Q is (R,R)-1,2-cyclohexyl. In some embodiments, Q is (S,S)-1,2-cyclohexyl. In some embodiments, Q is (R,R)-1,2-cyclohexyl when the bond between the biaryl linkage is of S chirality. In some embodiments, Q is (S,S)-1,2-cyclohexyl when the bond between the biaryl linkage is of R chirality.

In some embodiments, each occurrence of Q is independently an optionally substituted C$_6$-C$_{10}$ aryl group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—. In some embodiments, Q is 1,2-phenyl.

In some embodiments, Q optionally substituted C$_{5-10}$ aliphatic. In some embodiments, Q optionally substituted C$_{6-8}$ aliphatic.

Consistent with our earlier disclosure, the R groups of bimetallic complexes of the present invention may be selected from a variety of suitable substituents. Exemplary substituents are disclosed herein. In certain embodiments, an R group may comprise a polymer backbone such that the bimetallic complex is immobilized on a solid support.

In some embodiments, each occurrence of R$^1$ and R$^2$ is independently hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, or —NR$^y$C(O)OR$^y$. In some embodiments, each occurrence of R$^1$ and R$^2$ is independently an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In some embodiments, R$^1$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, or —NR$^y$C(O)OR$^y$. In some embodiments, each occurrence of R$^1$ and R$^2$ is independently an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In some embodiments, R$^2$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, or —NR$^y$C(O)OR$^y$. In some embodiments, each occurrence of R$^1$ and R$^2$ is independently an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In some embodiments, R$^1$ and R$^2$ are taken together with their intervening atoms to form an optionally substituted 4-14-membered carbocycle, an optionally substituted 4-14-membered heterocycle, an optionally substituted 6-10-membered aryl group or an optionally substituted 5-10-membered heteroaryl group having 1-4 heteroatoms independently selected from nitrogen, oxygen, or sulfur ring. In certain embodiments, R$^1$ and R$^2$ are taken together with their intervening atoms to form an optionally substituted 6-10-membered aryl ring. In certain embodiments, R$^1$ and R$^2$ are taken together with their intervening atoms to form a 6-membered aryl ring. In some embodiments, R$^1$ and R$^2$ are taken together with their intervening atoms to form:

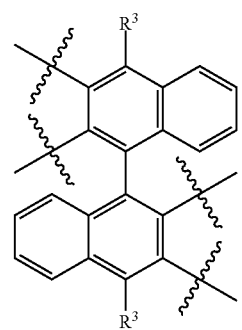

In other embodiments, R$^1$ and R$^2$ are taken together with their intervening atoms to form an optionally substituted 4-14-membered carbocycle. In some embodiments, R$^1$ and R$^2$ are taken together with their intervening atoms to form an optionally substituted 6-12-membered carbocycle. In certain embodiments, $R^1$ and $R^2$ are taken together with their intervening atoms to form:

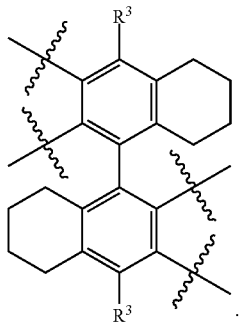

In some embodiments, each occurrence of $R^3$ and $R^4$ is independently independently hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N($R^y$)$_2$, —$NR^yC(O)R$, —$NR^yC(O)OR^y$. In some embodiments, each occurrence of $R^3$ and $R^4$ is independently an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur. In some embodiments, $R^3$ and $R^4$ are both hydrogen. In certain embodiments, $R^3$ and $R^4$ are independently a $C_{1-12}$ aliphatic group substituted with one or more organic cations, wherein each cation is complexed with an X, as defined herein. It will be appreciated that any X of an [organic cation][X] substituent is separate and in addition to any X moieties complexed with M. In some embodiments, the organic cation is a quaternary ammonium.

In certain embodiments, $R^3$ is hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N($R^y$)$_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, $R^4$ is hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N($R^y$)$_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, provided bimetallic complexes are of formula I-b:

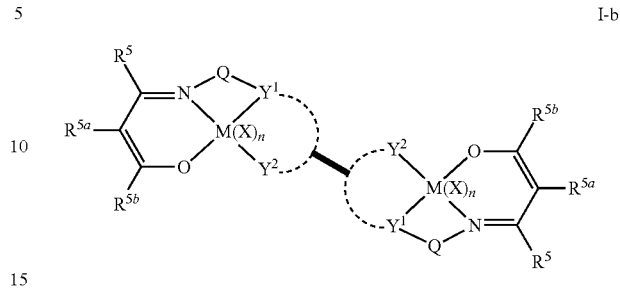

I-b wherein:
each of $\smile$, n, X, M, Q, $Y^1$, and $Y^2$ is as defined in formulae I and I-a and described in classes and subclasses above and herein;
each occurrence of $R^5$, $R^{5a}$, and $R^{5b}$ is independently hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N($R^y$)$_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; wherein adjacent $R^5$, $R^{5a}$, or $R^{5b}$ groups can be taken together to form an optionally substituted saturated, partially unsaturated, or aromatic 5- to 12-membered ring containing 0 to 4 heteroatoms; and
each occurrence of $R^y$ is independently hydrogen or an optionally substituted $C_{1-6}$ aliphatic group.

In certain embodiments, $R^5$ is hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N($R^y$)$_2$, —$NR^yC(O)R$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur. In certain embodiments, $R^5$ is hydrogen. In certain embodiments, $R^5$ is a $C_{1-12}$ aliphatic group substituted with one or more organic cations, wherein each cation is complexed with an X, as defined herein. It will be appreciated that any X of an [organic cation] [X] substituent is separate and in addition to any X moieties complexed with M. In some embodiments, the organic cation is a quaternary ammonium.

In certain embodiments, $R^{5a}$ is hydrogen, halogen, —$NO_2$, —CN, —$SR^y$, —S(O)$R^y$, —S(O)$_2R^y$, —$NR^yC(O)R^y$, —OC(O)$R^y$, —CO$_2R^y$, —NCO, —$N_3$, —O$R^y$, —OC(O)N($R^y$)$_2$, —N(R$^y$)$_2$, —NR$^y$C(O)R, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur. In certain embodiments, R$^{5a}$ and R$^{5b}$ are taken together to form an optionally substituted aromatic 6-10-membered ring. In certain embodiments, R$^{5a}$ and R$^{5b}$ are taken together to form an optionally substituted phenyl ring.

In certain embodiments, R$^{5b}$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, provided bimetallix complexes are of formula I-c:

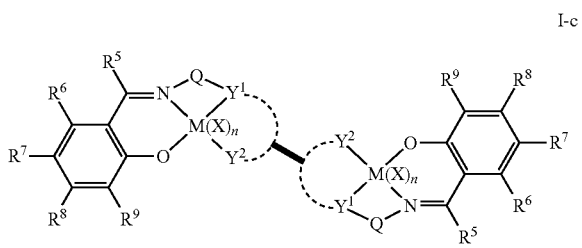

I-c wherein:

each of

, n, M, X, Q, Y$^1$, and Y$^2$ is as defined in formulae I and I-a and described in classes and subclasses above and herein; and each occurrence of R$^5$, R$^6$, R$^7$, R$^8$, and R$^9$ is independently hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; wherein adjacent R$^6$, R$^7$, R$^8$, or R$^9$ groups can be taken together to form an optionally substituted saturated, partially unsaturated, or aromatic 5- to 12-membered ring containing 0 to 4 heteroatoms.

In some embodiments, each occurrence of R$^5$, R$^6$, R$^7$, R$^8$, and R$^9$ is independently hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$. In some embodiments, each occurrence of R$^5$, R$^6$, R$^7$, R$^8$, and R$^9$ is hydrogen. In some embodiments, each occurrence of R$^5$, R$^6$, R$^7$, R$^8$, and R$^9$ is independently an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur. In certain embodiments, R$^5$, R$^6$, and R$^8$ are independently a C$_{1-12}$ aliphatic group substituted with one or more organic cations, wherein each cation is complexed with an X, as defined herein. It will be appreciated that any X of an [organic cation] [X] substituent is separate and in addition to any X moieties complexed with M. In some embodiments, the organic cation is a quaternary ammonium.

In certain embodiments, adjacent R$^6$, R$^7$, R$^8$, or R$^9$ groups can be taken together to form an optionally substituted saturated, partially unsaturated, or aromatic 5- to 12-membered ring containing 0 to 4 heteroatoms. In some embodiments, adjacent R$^6$, R$^7$, R$^8$, or R$^9$ groups are taken together to form an optionally substituted 5-6-membered cycloalkyl group. In some embodiments, adjacent R$^6$, R$^7$, R$^8$, or R$^9$ groups are taken together to form an optionally substituted 6-membered aryl group. In some embodiments, adjacent R$^6$, R$^7$, R$^8$, or R$^9$ groups are taken together to form an optionally substituted 5-7-membered heteroaryl group.

In certain embodiments, R$^5$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, R$^6$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, $R^7$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, $R^8$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, $R^9$ is hydrogen, halogen, —NO$_2$, —CN, —SR$^y$, —S(O)R$^y$, —S(O)$_2$R$^y$, —NR$^y$C(O)R$^y$, —OC(O)R$^y$, —CO$_2$R$^y$, —NCO, —N$_3$, —OR$^y$, —OC(O)N(R$^y$)$_2$, —N(R$^y$)$_2$, —NR$^y$C(O)R$^y$, —NR$^y$C(O)OR$^y$; or an optionally substituted group selected from the group consisting of C$_{1-12}$ aliphatic; C$_{1-2}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur.

In certain embodiments, each occurrence of $R^5$, $R^6$, $R^7$, $R^8$, and $R^9$ is hydrogen. In certain embodiments, each occurrence of $R^3$, $R^4$, $R^5$, $R^6$, $R^7$, $R^8$ and $R^9$ is hydrogen. In some embodiments, each of $R^3$, $R^4$, $R^5$, $R^6$, and $R^8$ is hydrogen In certain embodiments, each occurrence of $R^7$ and $R^9$ is an independently optionally substituted group selected from the group consisting of C$_{1-12}$ aliphatic and C$_{1-12}$ heteroaliphatic having 1-4 heteroatoms independently selected from the group consisting of nitrogen, oxygen, and sulfur. In some embodiments, $R^7$ and $R^9$ are optionally substituted C$_{1-12}$ aliphatic. In some embodiments, $R^7$ and $R^9$ are optionally substituted C$_{1-6}$ aliphatic. In some embodiments, $R^7$ and $R^9$ are t-butyl.

In certain embodiments, $R^7$ and $R^9$ are independently a C$_{1-12}$ aliphatic group substituted with one or more organic cations, wherein each cation is complexed with an X, as defined herein. It will be appreciated that any X of an [organic cation] [X] substituent is separate and in addition to any X moieties complexed with M. In some embodiments, the organic cation is a quaternary ammonium. In some embodiments, an organic cation substituent of a C$_{1-12}$ aliphatic group of $R^7$ and $R^9$ is selected from

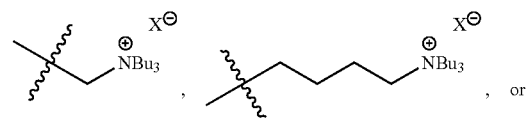

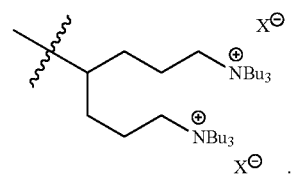

In certain embodiments, X is 2,4-dinitrophenolate anion.

In certain embodiments, provided bimetallic complexes are of formula II:

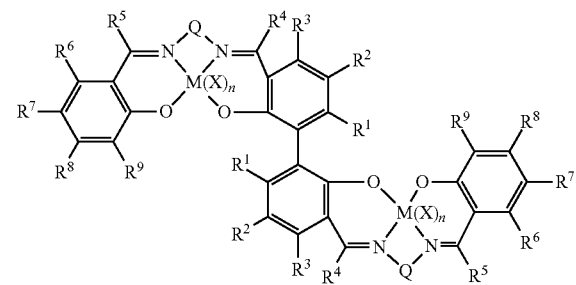

wherein:
each of M, X, Q, $R^1$, $R^2$, $R^3$, $R^4$, $R^5$, $R^6$, $R^7$, $R^8$, $R^9$ and n is as defined in formulae I, I-a, and I-b, and described in classes and subclasses above and herein;

In some embodiments, the bond between the biaryl linkage for a bimetallic complex of formula I, I-a, I-b, or II is of S chirality. In some embodiments, the bond between the biaryl linkage for a bimetallic complex of formula I, I-a, I-b, or II is of R chirality. In some embodiments, the bimetallic complex of formula I, I-a, I-b, or II is non-racemic. In some embodiments, the bimetallic complex of formula I, I-a, I-b, or II possesses axial chirality. In some embodiments, the bimetallic complex of formula I, I-a, I-b, or II possesses axial symmetry. In some embodiments, the bimetallic complex of formula I, I-a, I-b, or II is enantiomerically pure. In other embodiments, the bimetallic complex of formula I, I-a, I-b, or II is racemic.

In some embodiments, the bimetallic complex of formula I, I-a, I-b, or II is a catalyst. In certain embodiments, the catalyst is useful for isoselective polymerization of epoxides, as described herein. In certain embodiments, the catalyst is useful for kinetic resolution of epoxides, as described herein.

In certain embodiments, provided bimetallic metal complexes are of formula II-a:

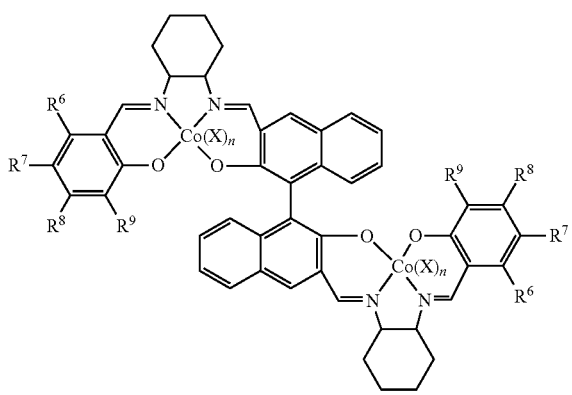

II-a wherein each of n, X, $R^6$, $R^7$, $R^8$, and $R^9$ is as defined above and described in classes and subclasses above and herein.

In certain embodiments, provided bimetallic metal complexes are of formula II-b:

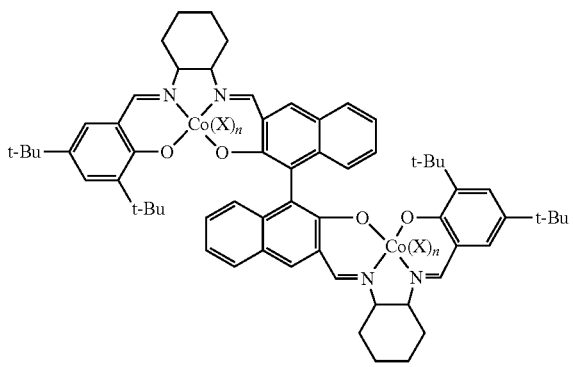

II-b wherein n and X are as defined above and described in classes and subclasses above and herein.

In certain embodiments, provided bimetallic metal complexes are of formula II-c:

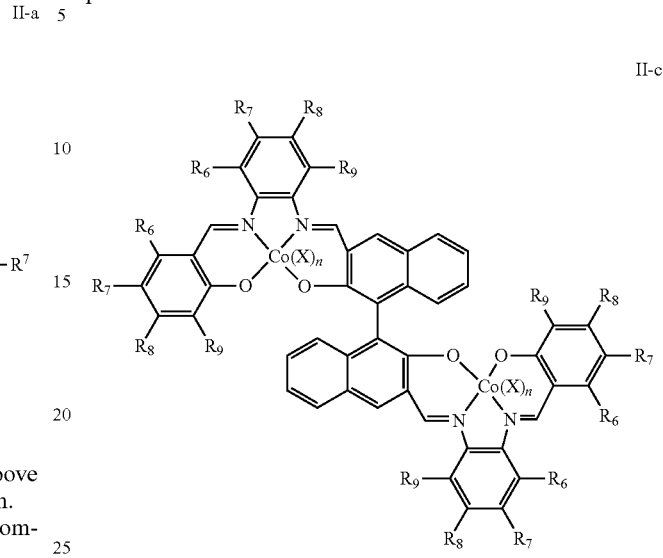

II-c wherein each of n, X, $R^6$, $R^7$, $R^8$, and $R^9$ is as defined above and described in classes and subclasses above and herein.

In some embodiments, the $k_{rel}$ of a provided bimetallic complex is greater than 7. In some embodiments, the $k_{rel}$ of a bimetallic complex is greater than 10. In some embodiments, the $k_{rel}$ of a bimetallic complex is greater than 20. In some embodiments, the $k_{rel}$ of a bimetallic complex is greater than 50. In some embodiments, the $k_{rel}$ of a bimetallic complex is greater than 100. In some embodiments, the $k_{rel}$ of a bimetallic complex is greater than 150. In some embodiments, the $k_{rel}$ of a bimetallic complex is greater than 200. In some embodiments, the $k_{rel}$ of a bimetallic complex is greater than 250. In some embodiments, the $k_{rel}$ of a bimetallic complex is greater than 300.

Exemplary Bimetallic Complexes

In certain embodiments, the bimetallic complex is selected from any one of following:

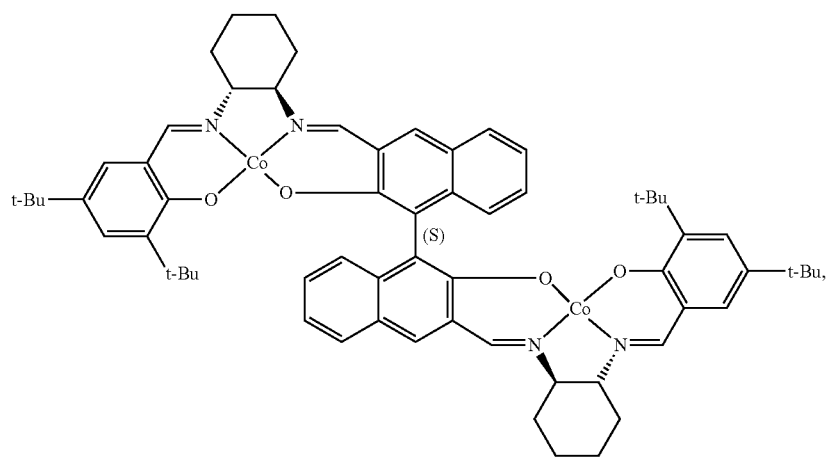

-continued
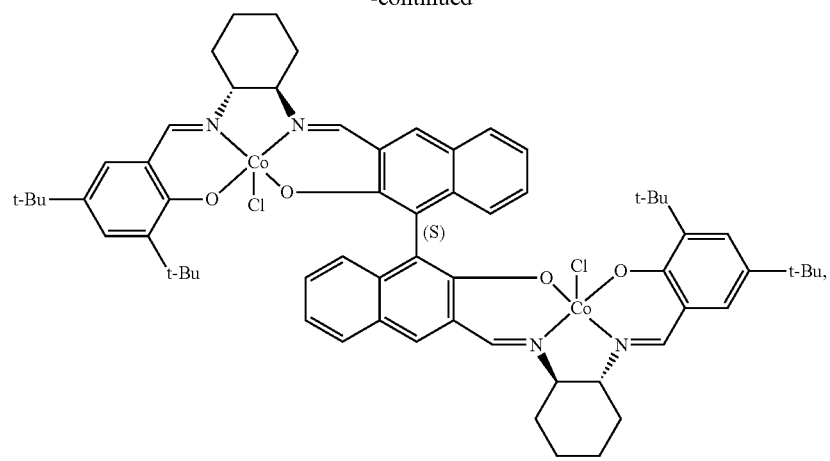
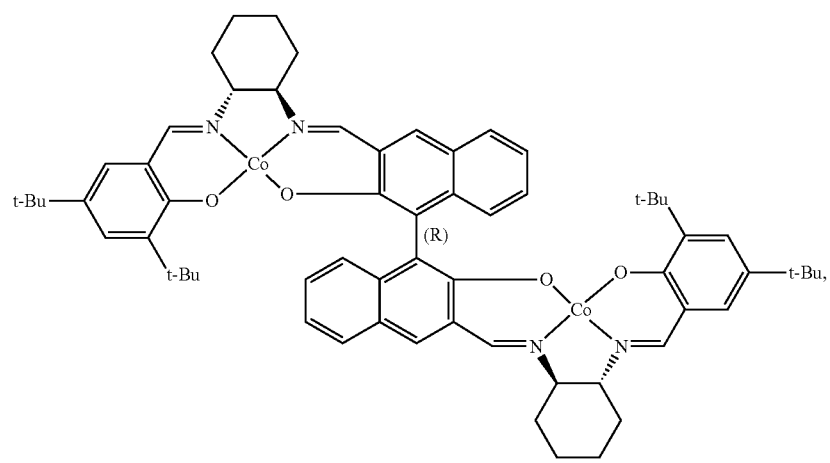
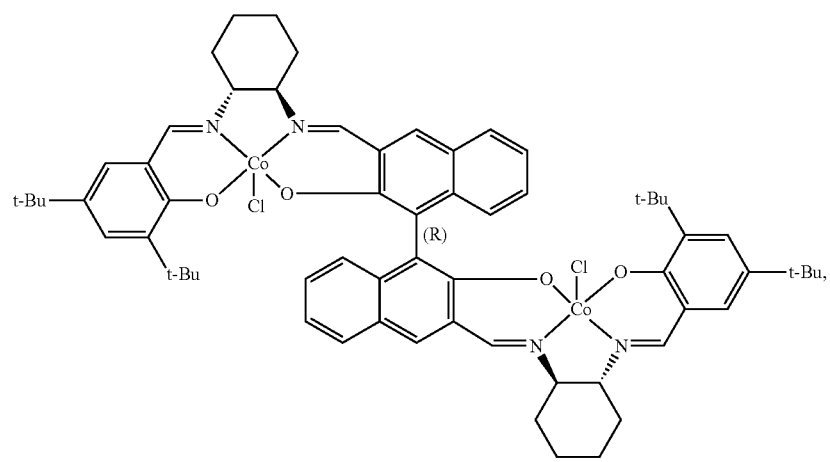

-continued
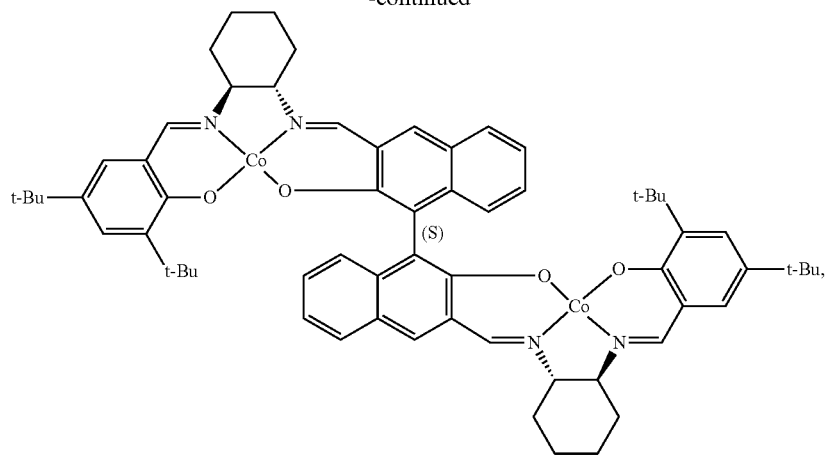
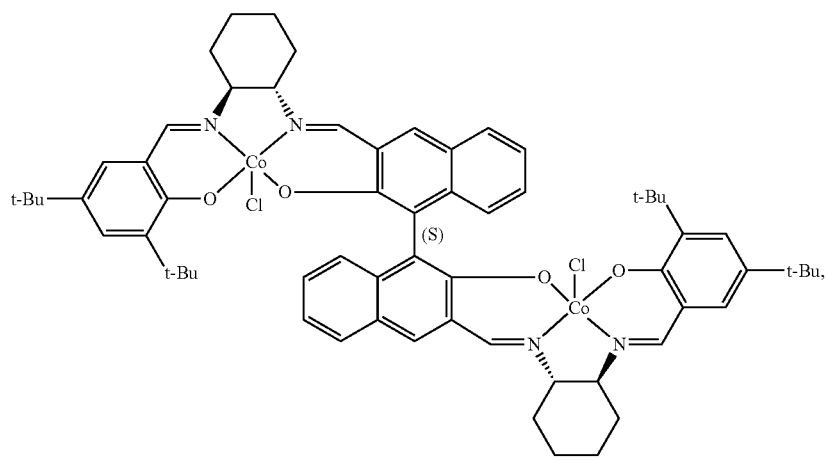
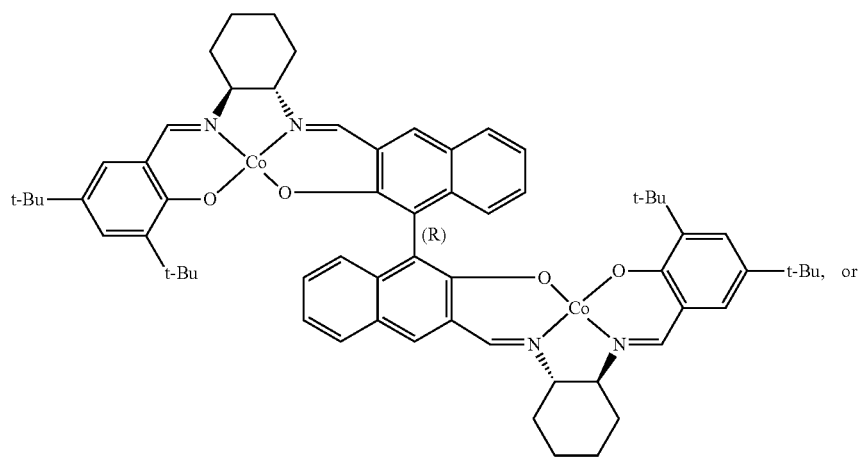
or

-continued

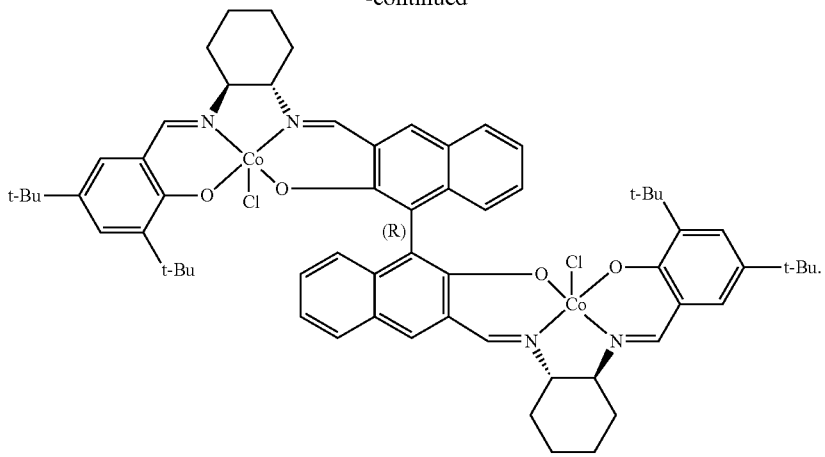

II. Polymers

According to one aspect, the present invention provides methods of making polymers. In certain embodiments, polymers are provided via polymerization of an epoxide in the presence of a bimetallic complex, and encompass racemic polyethers, optically enriched polyethers, and optically pure polyethers. In some embodiments, the polymer is a polyether. In certain embodiments, the polyether is highly isotactic. In certain embodiments, the polyether is perfectly isotactic. In some embodiments, the polyether is tapered. In some embodiments, the polyether is a co-polymer. It will be appreciated that the term "compound", as used herein, includes polymers described by the present disclosure.

In one aspect, the present invention provides a method of synthesizing a polyether polymer, the method comprising the step of reacting an epoxide in the presence of any of the above described bimetallic complexes.

In certain embodiments, provided polymers are of the formula:

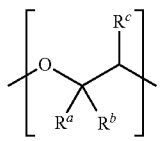

wherein:
  $R^a$ is an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and
  each of $R^b$ and $R^c$ is independently hydrogen or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;
  wherein any of ($R^a$ and $R^c$), ($R^b$ and $R^c$), and ($R^a$ and $R^b$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

Consistent with our earlier disclosure, $R^a$ of provided polymers may comprise a variety of organic substituents, the details of which are disclosed herein. Provided polymers may also have $R^b$ and $R^c$ substituents.

In certain embodiments, the polymer comprises a copolymer of two different repeating units where $R^a$, $R^b$, and $R^c$ of the two different repeating units are not all the same. In some embodiments, the polymer comprises a copolymer of three or more different repeating units wherein $R^a$, $R^b$, and $R^c$ of each of the different repeating units are not all the same as $R^a$, $R^b$, and $R^c$ of any of the other different repeating units. In some embodiments, the polymer is a random copolymer. In some embodiments, the polymer is a tapered copolymer.

In some embodiments, the polymer contains a bimetallic complex of formula I. In some embodiments, the polymer comprises residue of a bimetallic complex of formula I. In some embodiments, the polymer comprises a salt of an organic cation and X, wherein X is a nucleophile or counterion. In some embodiments, the organic cation is quaternary ammonium. In some embodiments, X is 2,4-dinitrophenolate anion.

In some embodiments, $R^a$ is optionally substituted $C_{1-12}$ aliphatic. In some embodiments, $R^a$ is optionally substituted $C_{1-12}$ heteroaliphatic having 1-4 heteroatoms independently selected from the group consisting of nitrogen, oxygen, and sulfur. In some embodiments, $R^a$ is optionally substituted 6-10-membered aryl. In some embodiments, $R^a$ is optionally substituted 5-10-membered heteroaryl having 1-4 heteroatoms independently selected from nitrogen, oxygen, or sulfur. In some embodiments, $R^a$ is optionally substituted 4-7-membered heterocyclic having 1-2 heteroatoms independently selected from the group consisting of nitrogen, oxygen, and sulfur.

In certain embodiments, $R^a$ is selected from methyl, ethyl, propyl, butyl, vinyl, allyl, phenyl, trifluoromethyl,

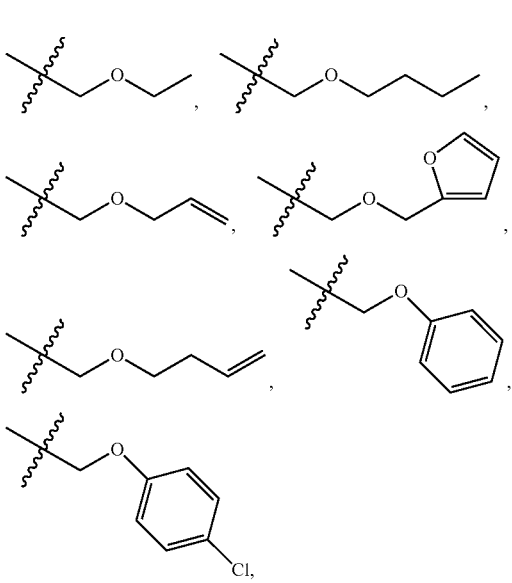

or any two or more of the above. In certain embodiments, $R^a$ is methyl. In certain embodiments, $R^a$ is ethyl. In certain embodiments, $R^a$ is propyl. In certain embodiments, $R^a$ is butyl. In certain embodiments, $R^a$ is vinyl. In certain embodiments, $R^a$ is allyl. In certain embodiments, $R^a$ is phenyl. In certain embodiments, $R^a$ is trifluoromethyl. In certain embodiments, $R^a$ is

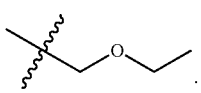 [SMILES: *COCC]

In certain embodiments, $R^a$ is

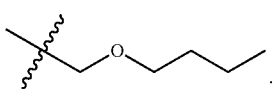 [SMILES: *COCCCC]

In certain embodiments, $R^a$ is

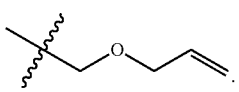 [SMILES: *COCC=C]

In certain embodiments, $R^a$ is

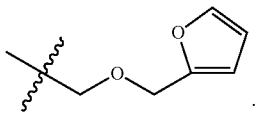

In certain embodiments, $R^a$ is

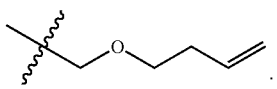 [SMILES: *COCCC=C]

In certain embodiments, $R^a$ is

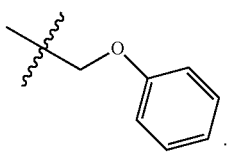 [SMILES: *COc1ccccc1]

In certain embodiments, $R^a$ is

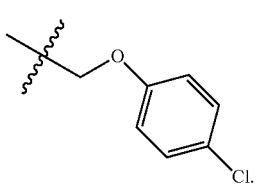 [SMILES: *COc1ccc(Cl)cc1]

In some embodiments, $R^a$ is other than

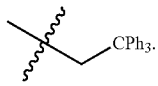

In some embodiments, $R^a$ is other than

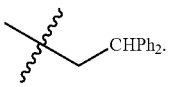

In some embodiments, $R^a$ is other than

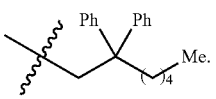

In some embodiments, $R^a$ is other than

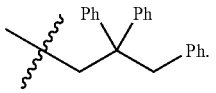 [SMILES: *CC(Cc1ccccc1)(c1ccccc1)c1ccccc1]

In some embodiments, $R^a$ is other than

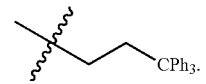

In some embodiments, $R^a$ is other than

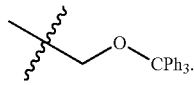

In some embodiments, $R^a$ is other than methyl. In some embodiments, $R^a$ is other than ethyl. In some embodiments, $R^a$ is other than propyl. In some embodiments, $R^a$ is other than

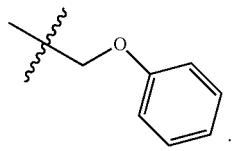

In some embodiments, $R^b$ is hydrogen. In some embodiments, $R^b$ is optionally substituted $C_{1-12}$ aliphatic. In some embodiments, $R^b$ is optionally substituted $C_{1-12}$ heteroaliphatic having 1-4 heteroatoms independently selected from the group consisting of nitrogen, oxygen, and sulfur. In some embodiments, $R^b$ is optionally substituted 6-10-membered aryl. In some embodiments, $R^b$ is optionally substituted 5-10-membered heteroaryl having 1-4 heteroatoms independently selected from nitrogen, oxygen, or sulfur. In some embodiments, $R^b$ is optionally substituted 4-7-membered heterocyclic having 1-2 heteroatoms independently selected from the group consisting of nitrogen, oxygen, and sulfur.

In some embodiments, $R^c$ is hydrogen. In some embodiments, $R^c$ is optionally substituted $C_{1-12}$ aliphatic. In some embodiments, $R^c$ is optionally substituted $C_{1-12}$ heteroaliphatic having 1-4 heteroatoms independently selected from the group consisting of nitrogen, oxygen, and sulfur. In some embodiments, $R^c$ is optionally substituted 6-10-membered aryl. In some embodiments, $R^c$ is optionally substituted 5-10-membered heteroaryl having 1-4 heteroatoms independently selected from nitrogen, oxygen, or sulfur. In some embodiments, $R^c$ is optionally substituted 4-7-membered heterocyclic having 1-2 heteroatoms independently selected from the group consisting of nitrogen, oxygen, and sulfur.

In some embodiments, $R^a$ and $R^c$ are taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

In some embodiments, $R^b$ and $R^c$ are taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

In some embodiments, $R^a$ and $R^b$ are taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl.

As described generally above, in certain embodiments, provided polymer are tapered. In certain embodiments, the enantiomeric excess of a polymer chain comprising the polymer decreases from one end of the polymer chain to the other end of the polymer chain. In some embodiments, the decrease in the enantiomeric excess from one end of the polymer to the second end of the polymer is gradual.

In some embodiments, the isotacticity of a polymer chain comprising the polymer is greater near one end of the polymer chain than near the other end of the polymer chain. In certain embodiments, the isotacticity of a polymer chain comprising the polymer decreases from one end of the polymer chain to the other end of the polymer chain.

In some embodiments, the isotacticity of the polymer is greater than 90%. In some embodiments, the isotacticity of the polymer is greater than 95%. In some embodiments, the isotacticity of the polymer is greater than 97%. In some embodiments, the isotacticity of the polymer is greater than 98%. In some embodiments, the isotacticity of the polymer is greater than 99%. It will be appreciated that the isotacticity is the overall isotacticity of the polymer.

In some embodiments, the %[mm] triad of the polymer is greater than 90%. In some embodiments, the %[mm] triad of the polymer is greater than 95%. In some embodiments, the %[mm] triad of the polymer is greater than 97%. In some embodiments, the %[mm] triad of the polymer is greater than 98%. In some embodiments, the %[mm] triad of the polymer is greater than 99%. It will be appreciated that the %[mm] triad is the overall %[mm] triad of the polymer.

In some embodiments, the Mn of the polymer is in the range of 10,000-25,000. In some embodiments, the Mn of the polymer is in the range of 25,000-50,000. In some embodiments, the Mn of the polymer is in the range of 50,000-100,000. In some embodiments, the Mn of the polymer is in the range of 100,000-200,000. In some embodiments, the Mn of the polymer is in the range of 200,000-400,000. In some embodiments, the Mn of the polymer less than 50,000. In some embodiments, the Mn of the polymer less than 25,000. In some embodiments, the Mn of the polymer greater than 200,000. In some embodiments, the Mn of the polymer greater than 300,000. In some embodiments, the Mn of the polymer greater than 500,000.

In some embodiments, the PDI of the polymer is less than 3. In some embodiments, the PDI of the polymer is less than 2.5. In some embodiments, the PDI of the polymer is less than 2.2. In some embodiments, the PDI of the polymer is less than 2. In some embodiments, the PDI of the polymer is less than 1.8. In some embodiments, the PDI of the polymer is less than 1.6. In some embodiments, the PDI of the polymer is less than 1.5. In some embodiments, the PDI of the polymer is less than 1.4. In some embodiments, the PDI of the polymer is less than 1.3. In some embodiments, the PDI of the polymer is less than 1.2. In some embodiments, the PDI of the polymer is less than 1.1.

In some embodiments, the $T_g$ of the polymer is in the range of −90 to −70° C. In some embodiments, the $T_g$ of the polymer is in the range of −70 to −50° C. In some embodiments, the $T_g$ of the polymer is in the range of −50 to −20° C. In some embodiments, the $T_g$ of the polymer is in the range of −20 to 20° C. In some embodiments, the $T_g$ of the polymer is in the range of 20 to 50° C. In some embodiments, the $T_g$ of the polymer is in the range of 50 to 70° C. In some embodiments, the $T_g$ of the polymer is in the range of 70 to 100° C. In some embodiments, the $T_g$ of the polymer is in the range of 100-120° C. In some embodiments, the $T_g$ of the polymer is in the range of 120-150° C. In some embodiments, the $T_g$ of the polymer is above 150° C.

In certain embodiments, the $T_n$ of the polymer is in the range of 20 to 50° C. In certain embodiments, the $T_n$ of the polymer is in the range of 50 to 70° C. In certain embodiments, the $T_n$ of the polymer is in the range of 70 to 100° C. In certain embodiments, the $T_n$ of the polymer is in the range of 100 to 120° C. In certain embodiments, the $T_n$ of the polymer is in the range of 120 to 150° C. In certain embodiments, the $T_n$ of the polymer is in the range of 150 to 190° C. In certain embodiments, the $T_n$ of the polymer is in the range of 190 to 210° C. In certain embodiments, the $T_n$ of the polymer is above 210° C.

In some embodiments, the polymer is optically inactive with m-dyad content greater than 80%. In some embodiments, the polymer is optically inactive with m-dyad content greater than 90%. In some embodiments, the polymer is optically inactive with m-dyad content greater than 95%. In some embodiments, the polymer is optically inactive with m-dyad content greater than 97%. In some embodiments, the polymer is optically inactive with m-dyad content greater than 98%. In some embodiments, the polymer is optically inactive with m-dyad content greater than 99%.

In certain embodiments, the polymer is crystalline. In certain embodiments, the polymer is semi-crytalline. In certain embodiments, the polymer is amorphous.

In addition to the epoxides described above, one of ordinary skill will appreciate that a variety of epoxides may be polymerized with a bimetallic complex of formula I. In certain embodiments, suitable epoxides are derived from naturally occurring materials such as epoxidized resins or oils. Examples of such epoxides include, but are not limited to: Epoxidized Soybean Oil; Epoxidized Linseed Oil; Epoxidized Octyl Soyate; Epoxidized PGDO; Methyl Epoxy Soyate; Butyl Epoxy Soyate; Epoxidized Octyl Soyate; Methyl Epoxy Linseedate; Butyl Epoxy Linseedate; and Octyl Epoxy Linseedate. These and similar materials are available commercially from Arkema Inc. under the trade name Vikoflex®. Examples of such commerically available Vikoflex® materials include Vikoflex 7170 Epoxidized Soybean Oil, Vikoflex 7190 Epoxidized Linseed, Vikoflex 4050 Epoxidized Octyl Soyate, Vikoflex 5075 Epoxidized PGDO, Vikoflex 7010 Methyl Epoxy Soyate, Vikoflex 7040 Butyl Epoxy Soyate, Vikoflex 7080 Epoxidized Octyl Soyate, Vikoflex 9010 Methyl Epoxy Linseedate, Vikoflex 9040 Butyl Epoxy Linseedate, and Vikoflex 9080 Octyl Epoxy Linseedate. In certain embodiments, provided polyethers derived from epoxidized resins or oils are heteropolymers incorporating other epoxide monomers including, but not limited to: ethylene oxide, propylene oxide, butylene oxide, hexene oxide, cyclopentene oxide and cyclohexene oxide. These heteropolymers can include random co-polymers, tapered copolymers and block copolymers.

In certain embodiments of the present invention, monomers include epoxides derived from alpha olefins. Examples of such epoxides include, but are not limited to those derived from $C_{10}$ alpha olefin, $C_{12}$ alpha olefin, $C_{14}$ alpha olefin, $C_{16}$ alpha olefin, $C_{18}$ alpha olefin, $C_{20}$-$C_{24}$ alpha olefin, $C_{24}$-$C_{28}$ alpha olefin and $C_{30+}$ alpha olefins. These and similar materials are commercially available from Arkema Inc. under the trade name Vikolox®. Commerically available Vikolox® materials include those depicted in Table A, below. In certain embodiments, provided polyethers derived from alpha olefins are heteropolymers incorporating other epoxide monomers. These heteropolymers can include random co-polymers, tapered copolymers and block copolymers.

TABLE A

| Trade Name | Formula | Minimum Oxirane |
|---|---|---|
| Vikolox 10 | $C_{10}H_{20}O$ | 9.0% |
| Vikolox 12 | $C_{12}H_{24}O$ | 7.8% |

TABLE A-continued

| Trade Name | Formula | Minimum Oxirane |
|---|---|---|
| Vikolox 14 | $C_{14}H_{28}O$ | 6.8% |
| Vikolox 16 | $C_{16}H_{32}O$ | 6.0% |
| Vikolox 18 | $C_{18}H_{36}O$ | 5.4% |
| Vikolox 20-24 | $C_{20\text{-}24}H_{40\text{-}48}O$ | 4.4% |
| Vikolox 24-28 | $C_{24\text{-}28}H_{48\text{-}56}O$ | 3.25% |
| Vikolox 30+ | $C_{30+}H_{60}O$ | 2.25% |

III. Methods of Polymerization

As generally described above, the present invention provides methods of synthesizing polymer compositions from monomers in the presence of a bimetallic complex. In some embodiments, polyethers of the present invention can be provided via polymerization of epoxides in the presence of a bimetallic complex. In some embodiments, the polymerization is isoselective.

In certain embodiments, the present invention provides a method for polymerization, the method comprising:
a) providing a prochiral epoxide of formula:

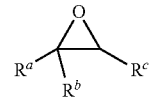

wherein:
$R^a$ is an optionally substituted group selected from the group consisting of $C_{1\text{-}12}$ aliphatic; $C_{1\text{-}12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and each of $R^b$ and $R^c$ is independently hydrogen or an optionally substituted group selected from the group consisting of $C_{1\text{-}12}$ aliphatic; $C_{1\text{-}12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

wherein any of ($R^a$ and $R^c$), ($R^b$ and $R^c$), and ($R^a$ and $R^b$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl;

and
b) treating the epoxide with a bimetallic catalyst under suitable conditions to form a polymer of formula:

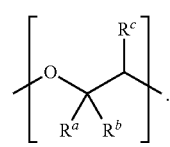

Consistent with our earlier disclosure, $R^a$ of epoxides may comprise a variety of organic substituents, the details of which are disclosed herein. Epoxides may also have $R^b$ and $R^c$ substituents to form 1,1- or 1,2-disubstituted epoxides. While initial experiments have not given good yields, provided bimetallic complexes may be used according to the invention to polymerize such 1,1- or 1,2-disubstituted epoxides.

In some embodiments, the bimetallic complex used in step b is a bimetallic complex of formula I or a subclass thereof. In some embodiments, the bimetallic complex used in step b is a bimetallic complex of formula II or a subclass thereof. In some embodiments, the bimetallic complex is a catalyst. In certain embodiments, the bimetallic complex used in step b is selected from:

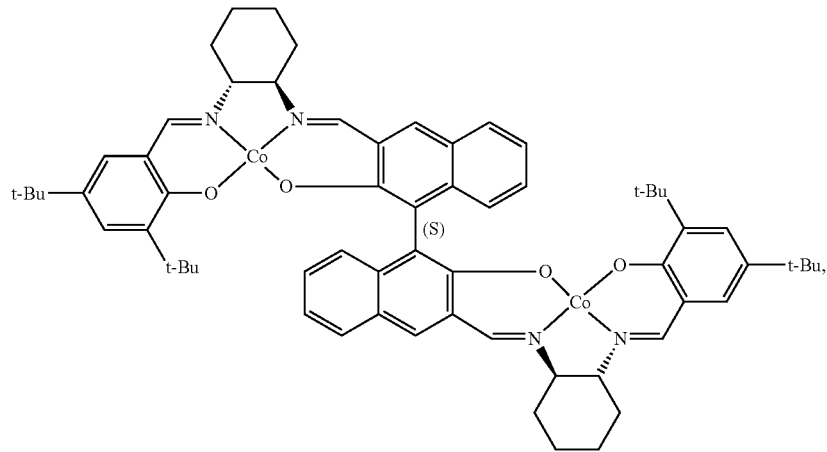

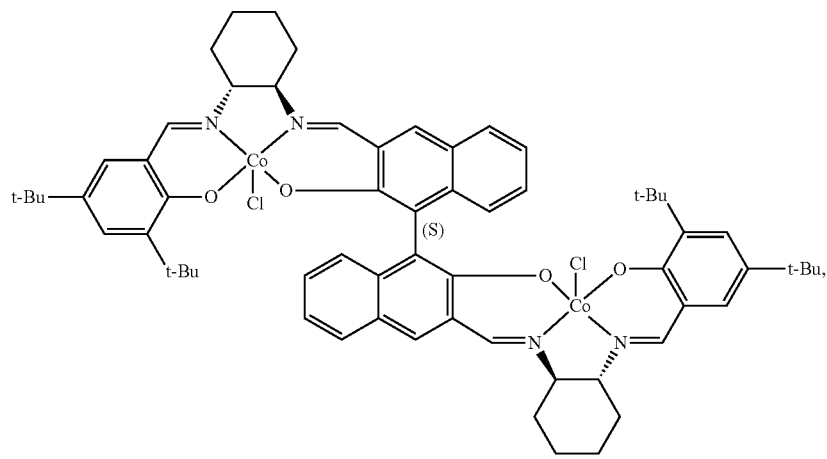

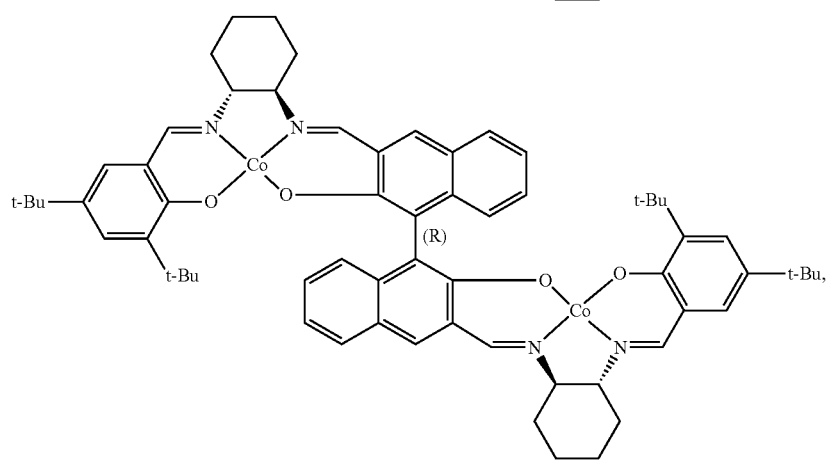

-continued
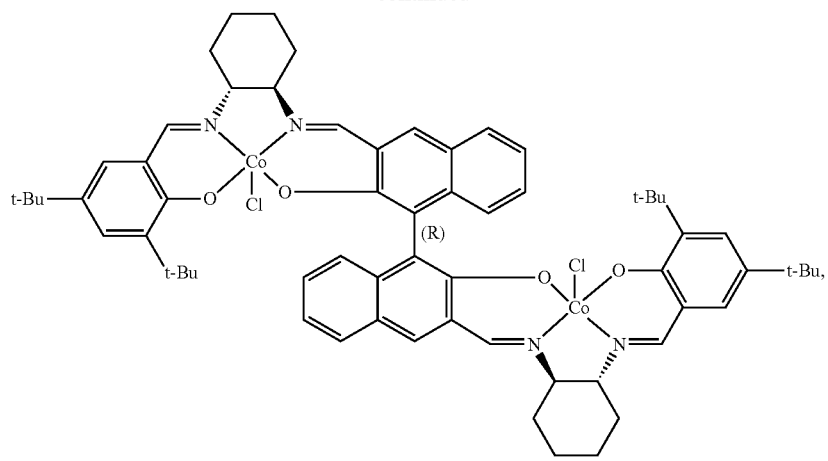
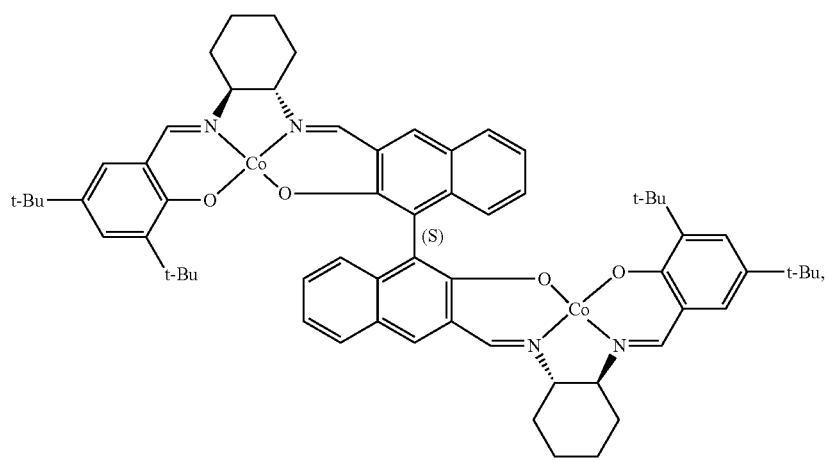
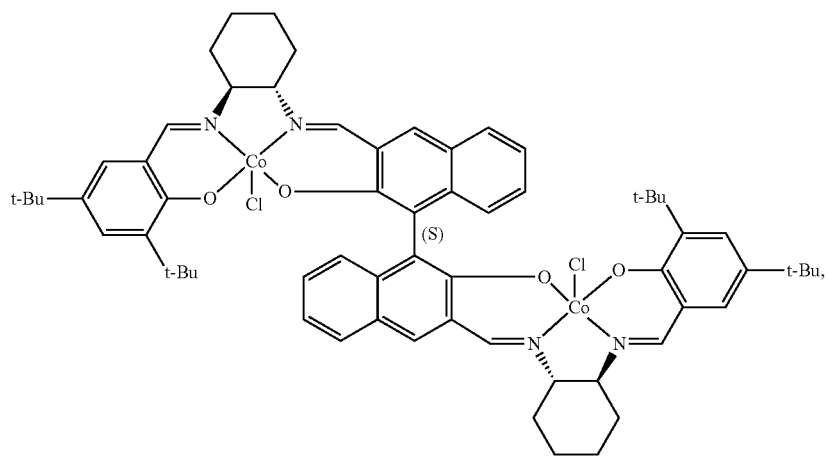

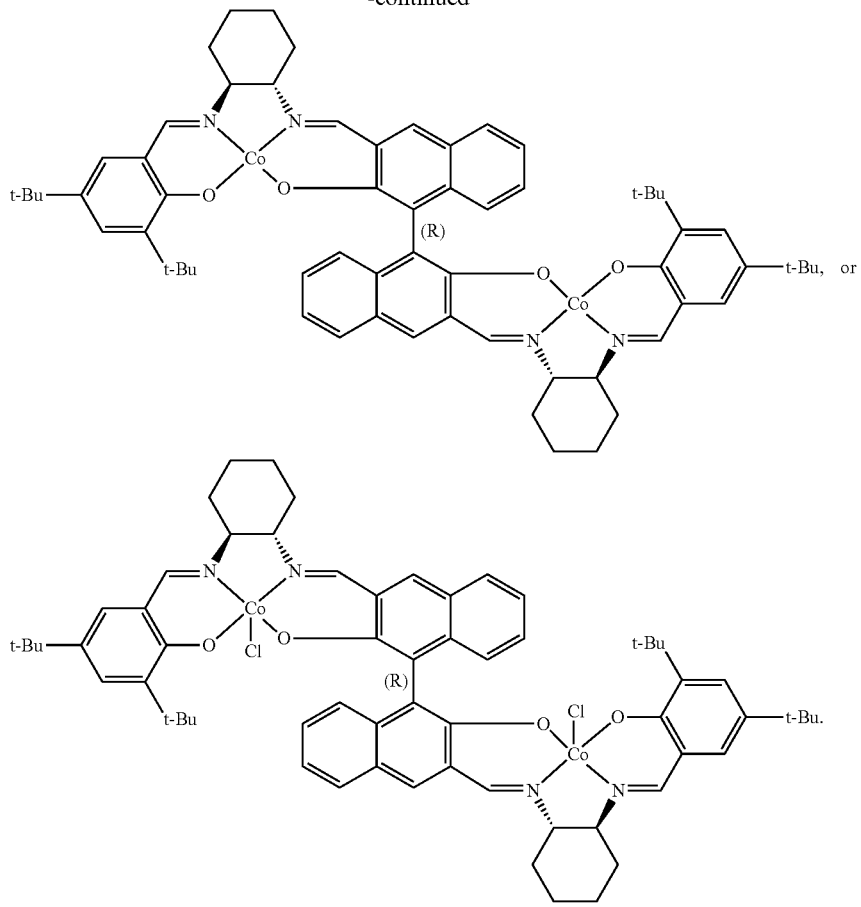

In certain embodiments, the method may further include, after step (a), adding at least one additional epoxide having the formula

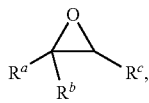

wherein each of the additional epoxide has a structure different from the structure of the epoxide provided in step (a) such that the polymer formed in step (b) is a co-polymer of two or more epoxides.

In certain embodiments, the polymerization is carried out with a 50:50 mixture of enantiomers of a bimetallic complex to form an optically inactive polyether. In other embodiments, the polymerization is carried out an enantiomerically enriched bimetallic complex to form optically active polyethers. In some embodiments, the polymerization is isoselective. In some embodiments, the bimetallic complex is enantiomerically pure. In some embodiments, the polyether is optically pure.

While not wishing to be bound by any particular theory, it is believed that the axial symmetry of provided bimetallic complexes is useful for providing enantioselective polymerization. In certain embodiments, additional chiral groups may be utilized in provided bimetallic complexes to modulate the enantioselectivity of the polymerization process.

While not wishing to be bound by any particular theory, it is believed that the axial symmetry of provided bimetallic complexes is useful for providing enantioselective kinetic resolution of epoxides. In certain embodiments, additional chiral groups may be utilized in provided bimetallic complexes to modulate the enantioselectivity of the kinetic resolution process.

In certain embodiments, when the bond between the biaryl linkage of provided bimetallic complexes is of S chirality, the provided products of the polymerization comprise polyethers with predominantly S chirality and epoxides with predominantly R chirality. In certain embodiments, when the bond between the biaryl linkage of provided bimetallic complexes is of R chirality, the provided products of the polymerization comprise polyethers with predominantly R chirality and epoxides with predominantly S chirality.

In certain embodiments, the polymer formed in step (b) has an enantiomeric excess greater than 90%. In certain embodiments, the polymer formed in step (b) has an enantiomeric excess greater than 95%. In certain embodiments, the polymer formed in step (b) has an enantiomeric excess greater than 97%. In certain embodiments, the polymer formed in step (b) has an enantiomeric excess greater than 98%. In certain embodiments, the polymer formed in step (b) has an enantiomeric excess greater than 99%.

In some embodiments, the %[mm] triad of the polymer formed in step (b) is greater than 90%. In some embodiments, the %[mm] triad of the polymer formed in step (b) is greater than 95%. In some embodiments, the %[mm] triad of the polymer formed in step (b) is greater than 97%. In some embodiments, the %[mm] triad of the polymer formed in step (b) is greater than 98%. In some embodiments, the %[mm] triad of the polymer formed in step (b) is greater than 99%.

In some embodiments, the $k_{rel}$ of the polymer formed in step (b) is greater than 7. In some embodiments, the $k_{rel}$ of the polymer formed in step (b) is greater than 10. In some embodiments, the $k_{rel}$ of the polymer formed in step (b) is greater than 20. In some embodiments, the $k_{rel}$ of the polymer formed in step (b) is greater than 50. In some embodiments, the $k_{rel}$ of the polymer formed in step (b) is greater than 100. In some embodiments, the $k_{rel}$ of the polymer formed in step (b) is greater than 150. In some embodiments, the $k_{rel}$ of the polymer formed in step (b) is greater than 200. In some embodiments, the $k_{rel}$ of the polymer formed in step (b) is greater than 250. In some embodiments, the $k_{rel}$ of the polymer is greater than 300.

In certain embodiments, the polymerization is enantioselective. In other embodiments, the polymerization is not enantioselective. In certain embodiments, the polymerization is living.

In some embodiments, the polymerization is a kinetic resolution. In certain embodiments, the present invention provides a method of steps (a) and (b) as described above, further comprising the step of recovering unreacted epoxide, wherein the recovered epoxide is enantiomerically enriched. In some embodiments, the enantiomeric excess of recovered epoxide is greater than 50%. In some embodiments, the enantiomeric excess of recovered epoxide is greater than 75%. In some embodiments, the enantiomeric excess of recovered epoxide is greater than 90%. In some embodiments, the enantiomeric excess of recovered epoxide is greater than 95%. In some embodiments, the enantiomeric excess of recovered epoxide is greater than 97%. In some embodiments, the enantiomeric excess of recovered epoxide is greater than 98%. In some embodiments, the enantiomeric excess of recovered epoxide is greater than 99%.

Reaction Conditions

In certain embodiments, any of the above methods further comprise use of an effective amount of one or more co-catalysts. In certain embodiments, the co-catalyst is an activating ionic substance. In some embodiments, the ionic substance is bis(triphenylphosphine)iminium.

In certain embodiments, a co-catalyst is a Lewis base. Exemplary Lewis bases include, but are not limited to: N-methylimidazole (N-MeIm), dimethylaminopyridine (DMAP), 1,4-diazabicyclo[2.2.2]octane (DABCO), triethyl amine, and diisopropyl ethyl amine.

In certain embodiments, a co-catalyst is a salt. In certain embodiments, a co-catalyst is an ammonium salt, a phosphonium salt or an arsonium salt. In certain embodiments, a co-catalyst is an ammonium salt. Exemplary ammonium salts include, but are not limited to: (n-Bu)$_4$NCl, (n-Bu)$_4$NBr, (n-Bu)$_4$NN$_3$, [PPN]Cl, [PPN]Br, and [PPN]N$_3$, Ph$_3$PCPh$_3$]Cl [PPN]O(C=O)R$^c$ (PPN=Bis(triphenylphosphoranylidene)ammonium)). In certain embodiments, a co-catalyst is a phosphonium salt. In certain embodiments, the co-catalyst is an arsonium salt.

In certain embodiments, a co-catalyst is the ammonium salt bis(triphenylphosphoranylidene)ammonium chloride ([PPN] Cl). In certain embodiments, a co-catalyst is PPNOAc. In certain embodiments, the co-catalyst is a tributylammonium salt.

In certain embodiments, the anion of a salt co-catalyst has the same structure as the ligand X of the above described bimetallic complexes of formula I or II, or subsets thereof, wherein X is a nucleophilic ligand. For example, in certain embodiments, the co-catalyst is ([PPN]X) or (n-Bu)$_4$NX.

In certain embodiments, one or more units of co-catalyst may be tethered to a bimetallic complex intramolecularly, forming an [organic cation][α] complex, wherein X is a suitable nucleophile or counterion. In certain embodiments, the co-catalyst is tethered as a substituent on a provided bimetallic complex, wherein the substituent is selected from

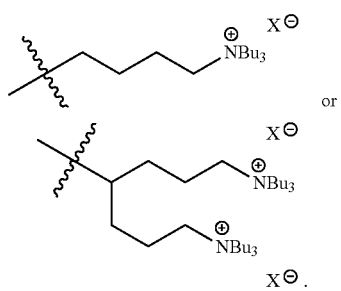

In certain embodiments, any of the above methods comprise a ratio of about 500:1 to about 500,000:1 of epoxide to bimetallic complex. In certain embodiments, any of the above methods comprise a ratio of about 500:1 to about 100,000:1 of epoxide to bimetallic complex. In certain embodiments, any of the above methods comprise a ratio of about 500:1 to about 50,000:1 of epoxide to bimetallic complex. In certain embodiments, any of the above methods comprise a ratio of about 500:1 to about 5,000:1 of epoxide to bimetallic complex. In certain embodiments, any of the above methods comprise a ratio of about 500:1 to about 1,000:1 of epoxide to bimetallic complex.

In certain embodiments, any of the above methods comprise epoxide present in amounts between about 0.5 M to about 20 M. In certain embodiments, epoxide is present in amounts between about 0.5 M to about 2 M. In certain embodiments, epoxide is present in amounts between about 2 M to about 5 M. In certain embodiments, epoxide is present in amounts between about 5 M to about 20 M. In certain embodiments, epoxide is present in an amount of about 20 M. In certain embodiments, liquid epoxide comprises the reaction solvent. In certain embodiments, one or more additional epoxides are present at any of the aforementioned concentrations.

In some embodiments, any of the above methods comprise a bimetallic complex present in amounts between about 0.001 M to about 1.0 mole %. In certain embodiments, a bimetallic complex is present in amounts between about 0.005 M to about 0.5 mole %. In certain embodiments, a bimetallic complex is present in amounts between about 0.01 M to about 0.1 mole %.

In certain embodiments, any of the above methods comprise the reaction to be conducted at a temperature of between about −78° C. to about 100° C. In certain embodiments, the reaction is conducted at a temperature of between about −10° C. to about 23° C. In certain embodiments, the reaction is conducted at a temperature of between about 23° C. to about 100° C. In certain embodiments, the reaction to be conducted at a temperature of between about 23° C. to about 80° C. In certain embodiments, the reaction to be conducted at a temperature of between about 23° C. to about 50° C. In certain embodiments, the reaction to be conducted at a temperature of about 23° C. In certain embodiments, the reaction to be conducted at a temperature of about 0° C.

In certain embodiments, the reaction step of any of the above methods does not further comprise a solvent.

In certain embodiments, the reaction step of any of the above methods does further comprise one or more solvents. In certain embodiments, the solvent is an organic solvent. In certain embodiments, the solvent is a hydrocarbon. In certain embodiments, the solvent is an aromatic hydrocarbon. In certain embodiments, the solvent is an aliphatic hydrocarbon. In certain embodiments, the solvent is a halogenated hydrocarbon.

In certain embodiments, the solvent is an organic ether. In certain embodiments the solvent is a ketone.

In certain embodiments suitable solvents include, but are not limited to: methylene chloride, chloroform, 1,2-dichloroethane, propylene carbonate, acetonitrile, dimethylformamide, N-methyl-2-pyrrolidone, dimethyl sulfoxide, nitromethane, caprolactone, 1,4-dioxane, and 1,3-dioxane.

In certain other embodiments, suitable solvents include, but are not limited to: methyl acetate, ethyl acetate, acetone, methyl ethyl ketone, propylene oxide, tetrahydrofuran, monoglyme, triglyme, propionitrile, 1-nitropropane, cyclohexanone. In some embodiments, the solvent is toluene.

IV. Applications

The present disclosure provides isotactic polyethers having a wide range of uses. It is well known in the art that isotactic and enantioselective polymers may be used in the manufacture of consumer goods such as materials for food packaging, electronics, packaging for consumer goods, chiral chromatographic media, polymeric reagents, and polymeric catalysts. In some embodiments, the material is oil resistant. In some embodiments, the material is a film. In some embodiments, the material is extruded. In some embodiments, the material is thermoformed. One of ordinary skill in the art will be knowledgeable of the techniques of manufacturing such materials and goods once provided with the bimetallic complexes, methods, and polymers of the present disclosure.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

I. General Considerations.

All manipulations of air or water sensitive compounds were carried out under dry nitrogen using a Braun Labmaster drybox or standard Schlenk line techniques. $^1$H NMR spectra were recorded on a Varian Mercury ($^1$H, 300 MHz), Varian INOVA 400 ($^1$H, 400 MHz), or Varian INOVA 500 ($^1$H, 500 MHz) spectrometer and referenced with residual non-deuterated solvent shifts (CHCl$_3$=7.26 ppm, benzene-d$_5$=7.16, acetone-d$_5$=2.05 ppm, DMSO-d$_5$=2.54 ppm, 1,1,2,2-tetrachloroethane-d$_1$=6.0 ppm). $^{13}$C NMR spectra were recorded on a Varian INOVA 500 ($^{13}$C, 125 MHz) spectrometer and were referenced by solvent shifts (CDCl$_3$=77.23 ppm, benzene-d$_6$=128.32 ppm, acetone-d$_6$=29.92 ppm, 1,1,2,2-tetrachloroethane-d$_2$=73.78 ppm).

II. Polymer Characterization.

Number average molecular weights ($M_n$) and polydispersity indexes (PDI) were measured by high temperature gel-permeation chromatography (GPC) using a Waters Alliance GPCV 2000 size exclusion chromatography equipped with a Waters DRI detector and viscometer. The set of five sequential columns (four Waters HT 6E and one Waters HT 2) was eluted with 1,2,4-trichlorobenzene containing approximately 0.01 wt % 2,6-di-tert-butylhydroxytoluene (BHT) at 1.0 mL/min. at 140° C. The Waters viscometer processing method was used for data analysis. The GPC chromatographs generated from the Waters viscometer were calibrated using polystyrene standards.

Polymer melting points ($T_m$) and glass transition temperatures ($T_g$) were measured by differential scanning calorimetry (DSC) using a TA Instruments Q1000 DSC equipped with a LNCS and an automated sampler. Polymer samples were heated under nitrogen from room temperature to 250° C. at a rate of 10° C. per minute and then cooled to −15° C. at 10° C. per minute, followed by heating to 250° C. at 10° C. per minute. The data from the second heating run was processed using the TA Q series software, and peak melting points and glass transition temperatures were reported.

III. Epoxide Enantiomeric Excess.

The enantiomeric excess (ee) of recovered epoxides was determined either by chiral gas chromatography (GC) or by $^1$H NMR spectroscopy using a chiral Schiff reagent to produce diastereomers with different NMR shifts. Gas chromatograms were obtained on a Hewlett-Packard 6890 series gas chromatograph using a flame ionization detector, He carrier gas, and one of two chiral columns, depending on the particular epoxide. An Alltech CHIRALDEX A-TA chiral capillary column (50 m×0.25 mm) was used for PO and styrene oxide separation, and a Supelco Lot#10711-03A chiral beta-DEX 225 fused silica capillary column (30 m×0.25 m) was used for all other epoxides. In each case pure racemic epoxide was run first on the GC to confirm separation of enantiomers and retention times. $^1$H NMR using a chiral Schiff reagent was used to obtain the ee of the few epoxides that would not resolve on either GC chiral column. Under nitrogen in a drybox, a solution was made of Europium tris [3-(trifluoromethylhydroxymethylene)-(+)-camphorate] as the chiral Schiff reagent in benzene-d$_6$ (83 mg in 1.5 g, respectively). 0.4 mL of this solution was added to an NMR tube, which was sealed with a septum cap. 20 µL of recovered epoxide was inserted via syringe through the septum cap (this volume was adjusted for recovered epoxides containing toluene), and the solution was mixed prior to performing NMR spectroscopy. Optical rotations were measured on a Perkin-Elmer 241 digital polarimeter using a sodium lamp.

IV. Polymer Enantiomeric Excess and Tacticity.

Derivation of the Relationship between Polymer Enantiomeric Excess and Isotacticity:

The $^{13}$C NMR spectrum of PPO shows [mr+rm]:[rr] peak ratios of 2:1, indicating that the catalyst controls stereochemistry through an enantiomorphic-site control mechanism. Since the catalyst polymerizes epoxides via enantiomorphic-site control, the fractional m-dyad content [m] of the polymer is represented by the following equation:

$$[m] = \alpha^2 + (1-\alpha)^2 \qquad \text{(eq. 1)}$$

where α is the fractional enantioselectivity parameter of the preferred enantiomer (for a perfect catalyst, α=1) (FIG. 1). For (R,R)(S)-1, α is the probability of incorporating (S) PO, and (1−α) is the probability of incorporating (R)PO. Since enantiomeric excess is defined as ee=(S−R)/(R+S), by inserting α for (S) and (1−α) for (R), an equation is derived for the ee of the polymer in terms of α.

$$ee_{(p)} = \frac{\alpha - (1-\alpha)}{\alpha + (1-\alpha)} \qquad \text{(eq. 2)}$$

Equation 2 can be simplified to equation 3, below.

$$ee_{(p)} = 2\alpha - 1 \qquad \text{(eq. 3)}$$

Expanding equation 1 gives equation 4.

$$[m] = 2\alpha^2 - 2\alpha + 1 \qquad \text{(eq. 4)}$$

Rearranging equation 3 gives equation 5, which now can be equated with equation 4.

$$ee_{(p)}^2/2 = 2\alpha^2 - 2\alpha + \frac{1}{2} \qquad \text{(eq. 5)}$$

Combing equations 4 and 5 gives $ee_{(p)}$ in terms of [m].

$$[m] - 1 = \frac{ee_{(p)}^2}{2} - \frac{1}{2}$$

Rearranging gives equation 6, below.

$$ee_{(p)} = \sqrt{2[m]-1} \qquad \text{(eq. 6)}$$

The m-dyad is calculated from triads [mm] and [mr+rm] (eq. 7).

$$[m] = [mm] + \frac{1}{2}[mr+rm] \qquad \text{(eq. 7)}$$

The ee of the polymer is therefore calculated from the following equation.

$$ee_{(p)} = \{2[mm]+[mr]+[rm]-1\}. \qquad \text{(eq. 8)}$$

Figure 2:
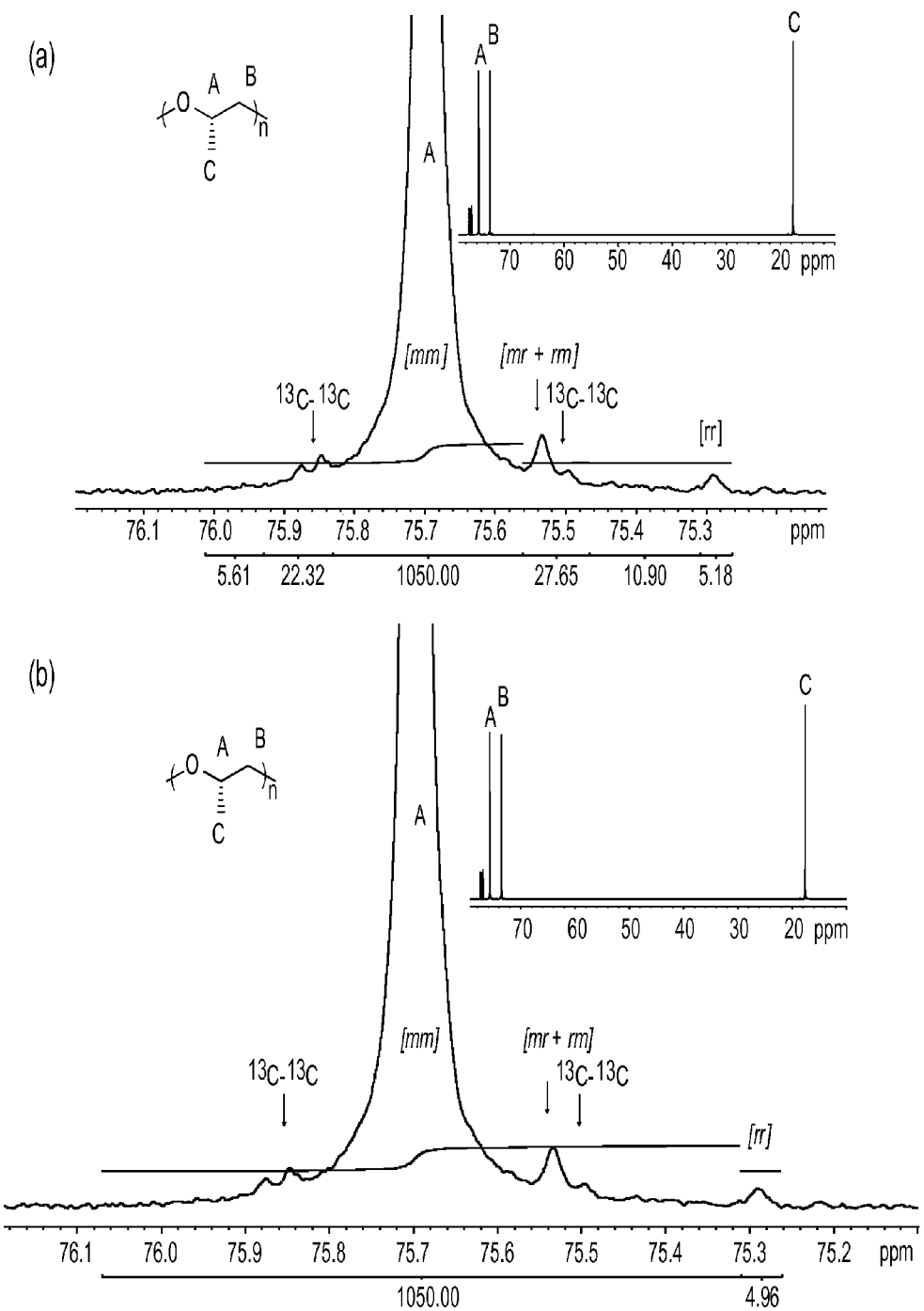
FIG. 2 depicts the calculation of $ee_{(p)}$ for PPO by $^{13}$C NMR Spectroscopy. (a) Separate integration of mr and rm peaks. (b) Integration using a triad peak.

NMR Quantification of Polymer Tacticity:

In this disclosure, the peaks in the $^{13}C$ NMR spectra of provided polyethers exhibit fine structure that result from stereochemical defects in the polymer chain. The $^{13}C$ NMR spectra of the aliphatic polyethers synthesized from PO, BO and HO show triad resolution of the methine resonance, which can be integrated and quantified to calculate $ee_{(p)}$. In some embodiments, provided polyethers exhibit triad resolution of the methine carbon. In certain embodiments, provided polyethers have significant overlap between the [mm], [mr+rm], and [rr] peaks of the methine resonance. In these cases, the methylene resonance was used to quantify the triad resolution and calculate $ee_{(p)}$. Since the mr and rm triads occur in the same region as the $^{13}C$-$^{13}C$ satellite peaks of the mm triad, the distinct rr triad peak is useful in accurately calculating $ee_{(p)}$ for highly isotactic samples, especially when the mr and rm triads are smaller than the satellite peaks. The integration of the rr triad is multiplied by two (to equal the value of the mr and rm triads), and this value is subtracted from the integration of the mm, mr, and rm triads to give the value of the mm triad. For example, the ee of PPO can be calculated by separate integrations of the triads, in which the $^{13}C$-$^{13}C$ satellite peaks need to be subtracted out of the mr+rm peaks (method A), or by integration of the rr triad, from which the value of mr and rm triads can be calculated and subtracted from the total integration of mm, mr, and rm (method B) (FIG. 2). In certain embodiments, this second method is used due to $^{13}C$ NMR baseline separation of the rr triad peak from the other triad peaks.

Mathematical calculations for methods A and B (below) give the same value for the $ee_{(p)}$ of PPO. In some embodiments, Method B was used to calculate the $ee_{(p)}$ for other polyethers in this disclosure.

Method A: [From $^{13}C$ NMR integrations of the methine resonances, FIG. 2 (a)]

[rr]=5.18/1121.66=0.0046

[mr+rm]=[(27.65+10.9)−(22.32+5.61)]/1121.66=10.62/1121.66=0.0095

[mm]=1105.86/1121.66=0.986

[m]=[mm]+½[mr+rm]=0.991

$ee_{(p)} = \sqrt{2[m]-1} = 0.991$

Method B: [From $^{13}C$ NMR integrations of the methine resonances, FIG. 2 (b)]

[rr]=4.96/1054.96=0.0047

[mr+rm]=9.92/1054.96=0.0094

[mm]=1040.08/1054.96=0.986

[m]=[mm]+½[mr+rm]=0.991

$ee_{(p)} = \sqrt{2[m]-1} = 0.991$

As described above, in certain embodiments, provided polyethers are tapered, wherein the enantiomeric excess decreases from one end of the polymer chain to the other. One of ordinary skill will appreciate that such tapering can be observed by removing samples of polymer during the polymerization reaction, and using NMR techniques known in the art and described herein to show that the defect content increases with conversion.

Further references and techniques for using carbon-13 NMR to characterize polymer structures include: Schilling, F C; Tonelli, A E; *Macromolecules* 1986, 19, 1337-1343; Le Borgne, A; Spassky, N; Jun, C L; Momtaz, A; *Makromol. Chem.* 1988, 189 637-650; Ugur, M; Alyuruk, K; *J Poly Sci A: Polym Chem.* 1989, 27, 1749-1761.

V. Materials.

HPLC grade tetrahydrofuran, methylene chloride, and toluene were purchased from Fisher Scientific and purified over solvent columns. Reagent grade acetone, n-pentane, chloroform, and methanol were used as purchased. Absolute ethanol was degassed by sparging with dry nitrogen. All epoxides were either purchased from commercial sources or synthesized following known procedures. Prior to use, the epoxides were dried over calcium hydride, degassed through several freeze-pump-thaw cycles, then vacuum transferred and stored under nitrogen in a drybox. Catalysts (R,R)(S)-1 and (S,S)(R)-1 were synthesized similar to that previously reported. (1R,2R)-Diaminocyclohexane (99% ee) and (1S,2S)-Diaminocyclohexane (99% ee) were purchased from Aldrich, and (S)-1,1'-bi-2-naphthol was purchased from TCI. (S)- and (R)-3,3'-diformyl-1,1'-bi-2-napthol, (1R,2R)- and (1S,2S)-2-(3,5-di-tert-butyl-2-hydroxybenzylideneamino) cyclohexanammonium chloride, and bis(triphenyl-phosphine)iminium acetate ([PPN][OAc]) were prepared according to literature procedure. All other reagents were purchased from commercial sources and used as received.

VI. Catalyst Synthesis.

Scheme 1. Catalyst Synthesis.
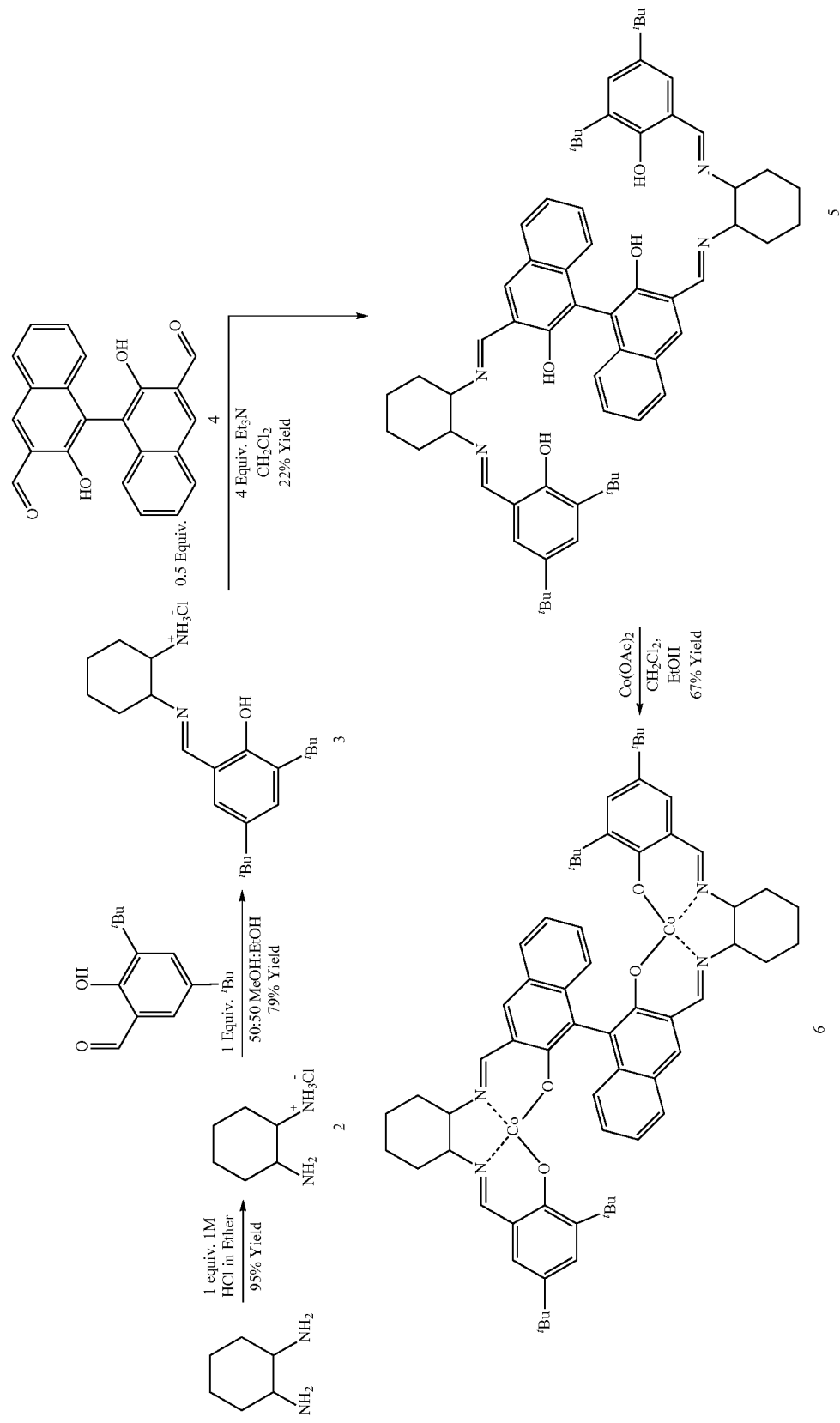

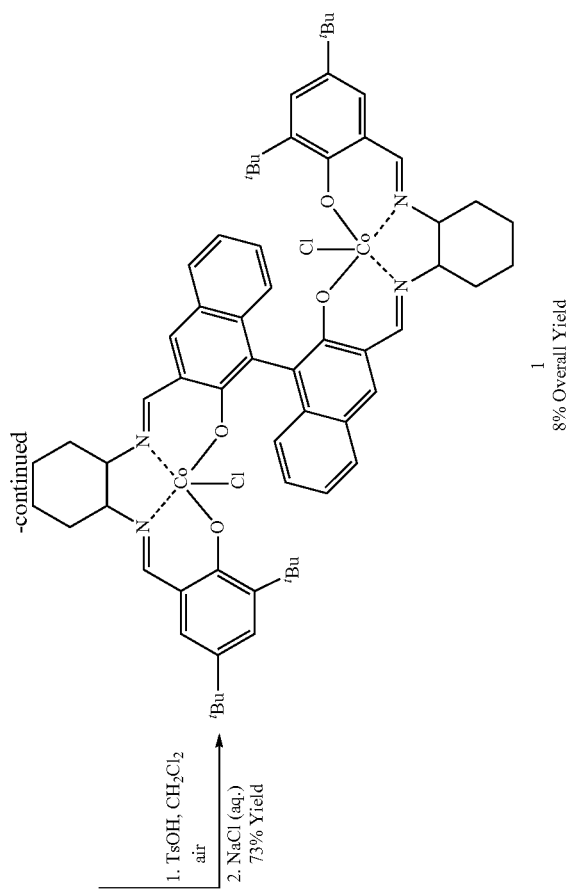

Synthesis of (R,R)(S)—5.

Under a nitrogen atmosphere, 4 Å molecular sieves, (S)-3,3'-diformyl-1,1'-bi-2-napthol (Scheme S1, 4) (3 g, 8.8 mmol), and (1R,2R)-2-(3,5-di-tert-butyl-2-hydroxybenzylideneamino)cyclohexanammonium chloride (Scheme 1, 3) (6.5 g, 17.7 mmol) were added to a 100 mL round bottom flask. Dry dichloromethane (60 mL) was added via canula, and triethylamine (3.6 g, 35.6 mmol) was added via syringe to the round bottom flask. The solution was stirred under a dry nitrogen atmosphere at room temperature for 3 days. The molecular sieves were then filtered off, and the orange filtrate was washed with concentrated $NH_4Cl$ (aq). The organic layer was dried over $MgSO_4$, filtered, and concentrated under partial vacuum, yielding an orange oil. The ligand was purified by column chromatography, using 10% ethyl acetate in hexanes with 1% triethylamine as the eluting solvent. The ligand decomposes under the acidic conditions of the column, so triethylamine was used to reduce ligand degradation. The $R_f$ of the desired product was 0.24 using 10% ethyl acetate in hexanes with 1% triethylamine as the TLC solvent. Isolated 1.9 g of pure target ligand as a yellow solid (22% yield).

$^1$H NMR ($CDCl_3$, 500 MHz) δ 13.81 (s, 2H), 12.95 (s, 2H), 8.59 (s, 2H), 8.23 (s, 2H), 7.82 (s, 2H), 7.73 (m, 2H), 7.32 (d, J=2.5 Hz, 2H), 7.21 (m, 4H), 6.99 (m, 2H), 6.98 (d, J=2.4 Hz, 2H), 3.44 (m, 2H), 3.17 (m, 2H), 1.98-2.04 (m, 2H), 1.78-1.92 (m, 6H), 1.6-1.74 (m, 4H), 1.49 (s, 18H), 1.36-1.47 (m, 4H), 1.25 (s, 18H).

$^{13}$C NMR ($CDCl_3$, 125 MHz) δ 166.13, 165.33, 157.92, 154.50, 139.89, 136.22, 135.01, 133.65, 128.77, 128.07, 127.48, 126.85, 126.20, 124.64, 123.11, 120.82, 117.66, 116.14, 72.94, 71.35, 34.98, 34.05, 33.46, 32.44, 31.46, 29.46, 24.19, 24.01.

Elemental Analysis: Anal. Calcd for $C_{64}H_{78}N_4O_4$: C, 79.46; H, 8.13; N, 5.79; O, 6.62. Found: C, 79.05; H, 8.37; N, 5.55.

Synthesis of (S,S)(R)-5.

Under a nitrogen atmosphere, 5 Å molecular sieves, (R)-3,3'-diformyl-1,1'-bi-2-napthol (Scheme 1, 4) (0.485 g, 1.4 mmol), and (1S,2S)-2-(3,5-di-tert-butyl-2-hydroxybenzylideneamino)cyclohexanammonium chloride (Scheme 1, 3) (1 g, 2.7 mmol) were added to a 100 mL round bottom flask. Dry dichloromethane (60 mL) was added via canula, and triethylamine (0.574 g, 5.7 mmol) was added via syringe to the round bottom flask. The solution was stirred under a dry nitrogen atmosphere at room temperature for 4 days. The solution was then filtered through celite, after which the orange filtrate was washed with concentrated $NH_4Cl$ (aq). The organic layer was dried over $Na_2SO_4$, filtered, and concentrated under partial vacuum, yielding a red-orange oil. The ligand was purified by column chromatography, using 10% ethyl acetate in hexanes with 1% triethylamine as the eluting solvent. The $R_f$ of the desired product was 0.25 using 10% ethyl acetate in hexanes with 1% triethylamine as the TLC solvent. Isolated 0.44 g of pure target ligand as a yellow solid (32% yield).

$^1$H NMR ($CDCl_3$, 500 MHz) δ 13.81 (s, 2H), 12.95 (s, 2H), 8.59 (s, 2H), 8.23 (s, 2H), 7.82 (s, 2H), 7.73 (m, 2H), 7.31 (d, J=2.5 Hz, 2H), 7.21 (m, 4H), 7.08 (m, 2H), 6.98 (d, J=2.4 Hz, 2H), 3.44 (m, 2H), 3.17 (m, 2H), 1.96-2.06 (m, 2H), 1.78-1.92 (m, 6H), 1.6-1.74 (m, 4H), 1.49 (s, 18H), 1.36-1.47 (m, 4H), 1.25 (s, 18H).

$^{13}$C NMR ($CDCl_3$, 125 MHz) δ 166.13, 165.33, 157.92, 154.50, 139.89, 136.22, 135.01, 133.65, 128.77, 128.07, 127.48, 126.85, 126.20, 124.64, 123.11, 120.82, 117.66, 116.14, 72.94, 71.35, 34.98, 34.05, 33.46, 32.44, 31.46, 29.46, 24.19, 24.01.

Synthesis of (R,R)(S)-6.

Under vacuum using the Schlenk line, $Co(OAc)_2 \cdot 4H_2O$ (0.96 g, 3.9 mmol) was heated in a Schlenk tube until the complex turned color from pink to purple. Absolute ethanol was stirred over 4 Å molecular sieves under a nitrogen atmosphere, sparged with nitrogen to degas, and then added (25 mL) to the Schlenk tube containing $Co(OAc)_2$ under nitrogen atmosphere. The solution was bright purple. In a separate round bottom flask under a dry nitrogen atmosphere, (R,R)(S)-5 (1.75 g, 1.8 mmol) was dissolved in 20 mL of dry methylene chloride. This ligand solution was canulated into the Schlenk tube containing $Co(OAc)_2$. The solution instantly turned dark red-brown. The solution was heated to 60° C. under nitrogen for two hours, after which the Schlenk tube was opened to vacuum, and the solvent was removed under reduced pressure. The dark solids obtained were filtered and washed with n-pentane, which removes unreacted ligand as well as acetic acid that formed during the reaction. The red brick solids were washed with ethanol, then again with pentane, after which the powder was dried under vacuum to give 1.31 g of (R,R)(S)-6 (67% yield). Complex (R,R)(S)-6 was generally recrystallized by layering with methylene chloride and ethanol. An X-ray crystal structure was previously reported for complex (R,R)(S)-6. MALDI-TOF mass spectrum: m/z=1080.59, calc.=1080.44.

Synthesis of (S,S)(R)-6.

The same procedure was followed as for (R,R)(S)-6, except ligand (S,S)(R)-5 was used.

Synthesis of (R,R)(S)-1.

Complex (R,R)(S)-6 (1.3 g, 1.2 mmol) was dissolved in 40 mL of methylene chloride in a beaker, and para-toluene sulfonic acid monohydrate (0.487 g, 2.6 mmol) was added. The dark brown solution was stirred open to air for 48 hours, during which all the methylene chloride evaporated. The dark shiny solids were redissolved in methylene chloride and washed with concentrated aqueous sodium chloride to exchange the tosylate initiator for a chlorine initiator as reported by Jacobsen and coworkers (Nielsen et al., J. Am. Chem. Soc.; 2004; 126(5) pp 1360-1362). This exchange was confirmed by elemental analysis. The organic layer was washed three times with aqueous sodium chloride, and then dried over $MgSO_4$ and filtered. The solution was concentrated under partial pressure and the dark brown solids were washed with pentane to yield 1.02 g of (R,R)(S)-1 (73% yield).

$^1$H NMR (DMSO-$d_6$, 400 MHz) δ=8.0-8.6 (m, 4H), 7.8-7.9 (m, 2H), 6.8-7.4 (m, 12H), 2.8-3.0 (m, 4H), 1.8-2.0 (m, 6H), 1.7 (m, 2H), 1.5 (m, 4H), 1.4 (m, 2H), 1.3 (m, 2H), 1.2 (s, 18H), 0.9 (s, 18H).

Elemental Analysis: Anal. Calcd for $C_{64}H_{74}Cl_2Co_2N_4O_4$: C, 66.72; H, 6.47; Cl, 6.15; Co, 10.23; N, 4.86; O, 5.56. Found: C, 65.43; H, 6.83; Cl, 6.62; Co, 9.77; N, 4.6.

Synthesis of (S,S)(R)-1.

The same procedure was followed as for (R,R)(S)-1, except complex (S,S)(R)-6 was used. $^1$H NMR (DMSO-$d_6$, 400 MHz) δ=8.0-8.5 (m, 4H), 7.8 (m, 2H), 6.8-7.4 (m, 12H), 2.9 (m, 4H), 1.8-2.0 (m, 6H), 1.7 (m, 2H), 1.5 (m, 4H), 1.35 (m, 2H), 1.2 (m, 2H), 1.15 (s, 18H), 0.8 (s, 18H).

VII. Enantioselective Polymerization of Epoxides.

Representative Procedure for the Enantioselective Polymerization of Epoxides.

Polymerization of Racemic Propylene Oxide (Table 1, Entry 1).

Figure 3:
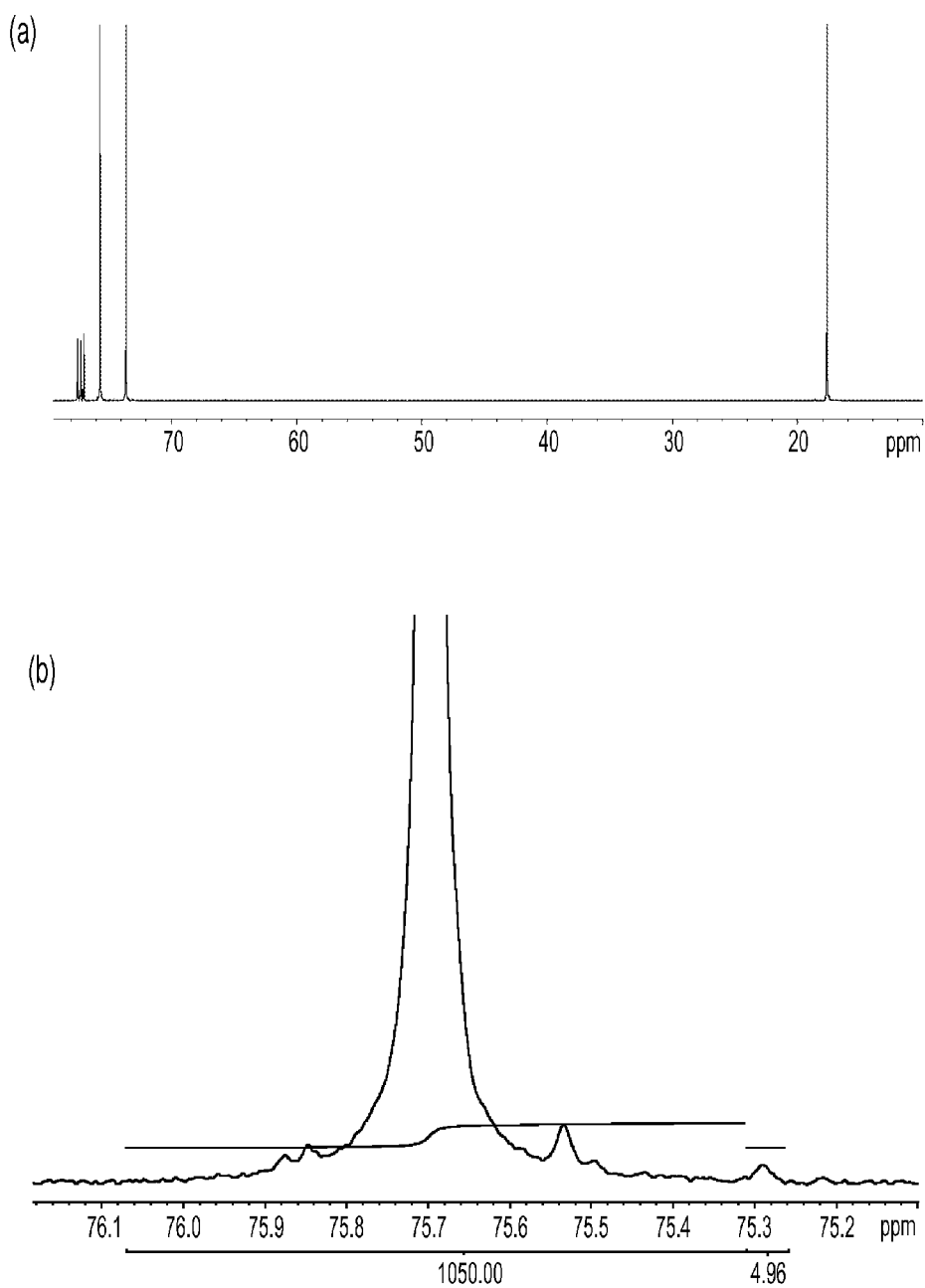
FIG. 3 depicts the $^{13}$C NMR spectra of PPO. a) Full spectrum. b) Methine carbon.

In a drybox under nitrogen atmosphere, (R,R)(S)-1 (8.2 mg, 0.0071 mmol) and [PPN][OAc] (8.5 mg, 0.0142 mmol) were added to a Schlenk tube containing a stir bar. A vacuum adaptor was attached to the Schlenk tube, and the Schlenk tube was sealed under nitrogen. A glass gas-tight syringe was used to draw up 2 mL (28.6 mmol) of racemic PO. The syringe was sealed under nitrogen by inserting the needle into a rubber septum. The Schlenk tube and the syringe containing PO were subsequently both brought out of the dry box. The Schlenk tube was placed under dry nitrogen on the Schlenk line, and subsequently cooled in an ice bath. Dry toluene (12 mL) was added to the Schlenk tube via syringe, and the resulting solution was stirred for 10 minutes at 0° C. The syringe containing PO was placed into a beaker, and the beaker and syringe were tared on a balance. PO was then added to the Schlenk tube, after which the syringe needle was immediately reinserted into the rubber septum. The syringe was placed into the beaker on the balance, and the difference in weight equaled the weight of the epoxide added to the Schlenk tube. The polymerization was kept at 0° C. during the course of the reaction. After 15 minutes unreacted PO was vacuum transferred to another Schlenk tube cooled in liquid nitrogen. The remaining polymer solution was transferred to a pre-weighed round bottom flask and dried overnight under vacuum. Conversion was determined by polymer mass (0.556 g PPO) to be 34%. The ee of recovered PO was measured by chiral gas chromatography to be 51% (R), with $t_R$=14.7 min and $t_S$=15.4 min. The absolute stereoconfiguration was confirmed by running commercially available (R)PO on the chiral GC. The conditions for separation were: flow, 1.4 mL/min; velocity, 34 cm/sec; pressure, 7 psi; isothermal at 40° C. A concentrated sample of PPO in $CDCl_3$ was made for $^{13}C$ NMR spectroscopy to determine polymer tacticity. 50 mg of polymer was dissolved in 0.5 mL of $CDCl_3$. An INOVA 500 Varian spectrometer was used to obtain the $^{13}C$ NMR spectrum (taken over 2 hrs, with 2000+ scans), as well as a $^1H$ NMR spectrum of the dried polymer. Polymer tacticity (FIG. 3): [mm]:[mr+rm]:[rr]=[0.986]:[0.0094]:[0.0047]. [m]=0.991, and $ee_{(p)}$=99.1%. $k_{rel(p)}$=370.

$^{13}C$ NMR ($CDCl_3$, 125 MHz): δ 75.70, 73.61, 17.64.
$^1H$ NMR ($CDCl_3$, 500 MHz): δ 3.52 (m, 2H), 3.39 (m, 1H), 1.11 (m, 3H).
$M_n$=26,400
PDI=1.8
$T_m$=64° C.
A $T_g$ was not detected.

TABLE 1

Enantioselective Polymerization of Epoxides.

| Entry | Epoxide | Time (min.) | Catalyst (mol %) | Conv. (%) | $ee_{(SM)}$ | % [mm] triad | $ee_{(p)}$ | $k_{rel(p)}$ | Mn | PDI | Tg (° C.) | Tm (° C.) |
|---|---|---|---|---|---|---|---|---|---|---|---|---|
| 1 | | 15 | 0.025 | 34 | 51% | 98.6 | 99.1% | 370 | 26,400 | 1.8 | ND | 64 |
| 2 | | 14 | 0.1 | 22 | 29% | 98.8 | 99.2% | 330 | 61,400 | 2.0 | −76 | — |
| 3 | | 20 | 0.15 | 19 | 24% | 98.6 | 99.1% | 260 | 76,800 | 2.1 | ND | 53 |
| 4 | | 50 | 0.05 | 24 | 31% | 93.4 | 95.5% | 59 | 7,600 | 1.5 | −62 | — |
| 5 | | 64 | 0.05 | 46 | 77% | 86.4 | 90.5% | 47 | 32,700 | 2.0 | −74 | 18 |
| 6 | | 11 | 0.025 | 36 | 57% | 98.3 | 98.9% | 310 | 106,200 | 1.5 | ND | — |
| 7 | | 7 | 0.025 | 41 | 80% | 97.9 | 98.6% | 280 | 68,900 | 1.2 | −27 | — |
| 8 | | 32 | 0.1 | 45 | 73% | 58.1 | 66.4% | 8 | 79,300 | 1.8 | −50 | 62 |
| 9 | | 11 | 0.15 | 35 | 53% | 98.6 | 99.0% | 340 | 45,700 | 1.9 | −69 | — |
| 10 | | 17 hrs | 0.1 | 20 | 26% | 94.4 | 96.1% | 63 | 98,800 | 1.9 | 50 | — |

TABLE 1-continued

Enantioselective Polymerization of Epoxides.

| Entry | Epoxide | Time (min.) | Catalyst (mol %) | Conv. (%) | ee$_{(SM)}$ | % [mm] triad | ee$_{(p)}$ | k$_{rel(p)}$ | Mn | PDI | Tg (° C.) | Tm (° C.) |
|---|---|---|---|---|---|---|---|---|---|---|---|---|
| 11 | 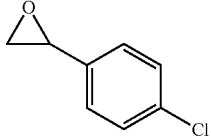 | 210 | 0.15 | 21 | 26% | 97.1 | 97.9% | 120 | 44,500 | 2.5 | 63 | — |
| 12 |  | 2 | 0.1 | 37 | 53% | 98.7 | 99.2% | 430 | | | ND | 121 |

Polymerization of Racemic Butene Oxide (Table 1, Entry 2).

Figure 4:
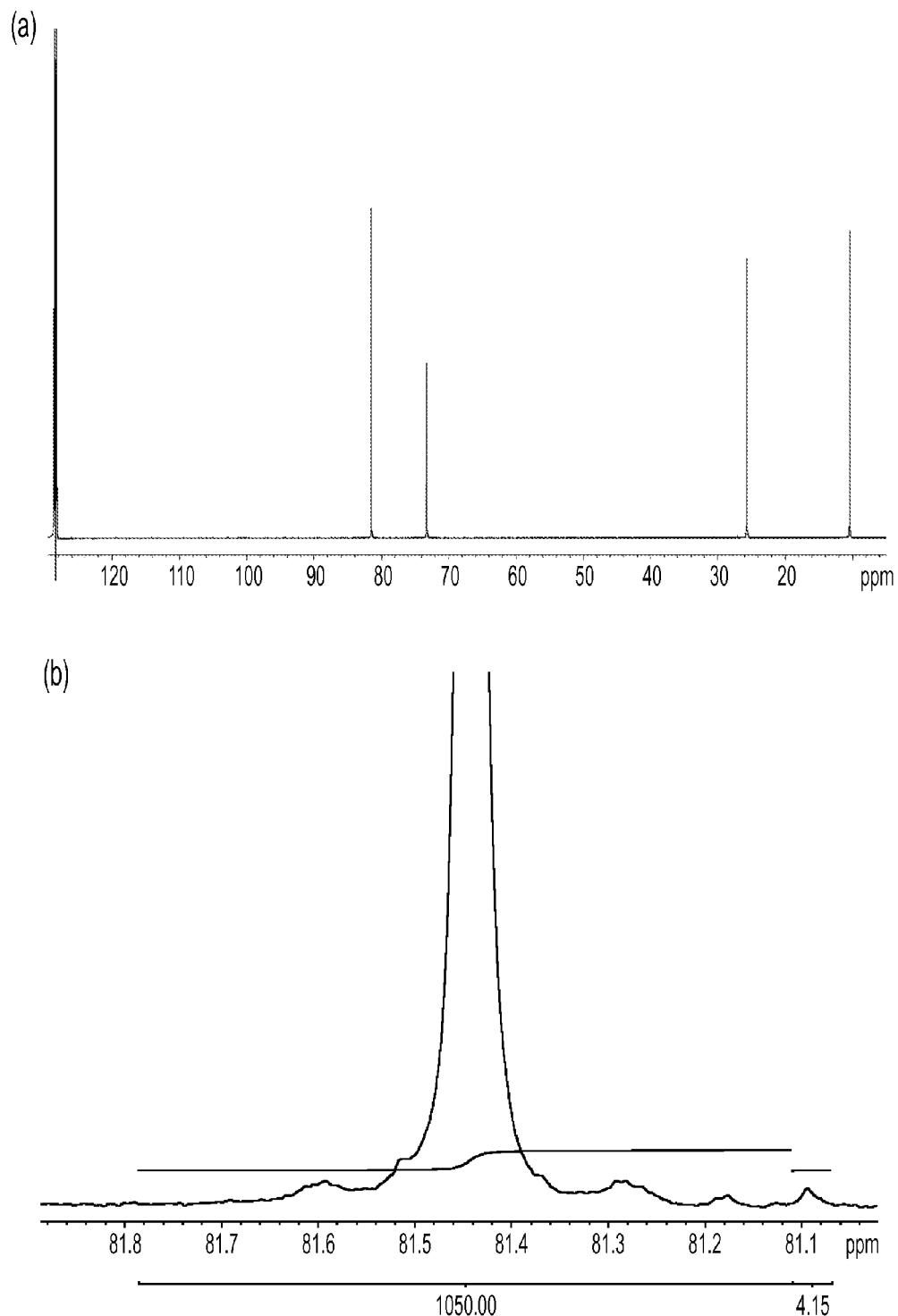
FIG. 4 depicts the $^{13}$C NMR spectra of PBO. a) Full spectrum. b) Methine carbon.

The polymerization procedure was the same as that for propylene oxide except that butene oxide was used. Butene oxide (0.5095 g, 7 mmol) was polymerized with (R,R)(S)-1 (8 mg, 0.0069 mmol) and [PPN][OAc] (8.3 mg, 0.0139 mmol) in dry toluene (2.9 mL). After 14 minutes reaction time, the unreacted butene oxide was vacuum transferred to a Schlenk tube cooled in liquid nitrogen. The ee of recovered BO was determined by $^1$H NMR spectroscopy using Europium tris[3-(trifluoromethylhydroxymethylene)-(+)-camphorate] as the chiral Schiff reagent in benzene-d$_6$. The NMR peaks were assigned and the absolute stereochemistry was confirmed by obtaining $^1$H NMR spectra of racemic and commercially available (R) butene oxide using the same Europium tris[3-(trifluoromethylhydroxymethylene)-(+)-camphorate]/benzene-d$_6$ solution. The ee of recovered BO was determined to be 29% (R). Conversion was determined by polymer mass (0.1097 g) to be 22%. A concentrated sample of PBO was made in benzene-d$_6$ for $^{13}$C NMR analysis. Polymer tacticity (FIG. 4): [mm]:[mr+rm]:[rr]=[0.988]:[0.0079]:[0.0039]. [m]=0.992. ee$_{(p)}$=99.2%. k$_{rel(p)}$=330.

$^{13}$C NMR (C$_6$D$_6$, 125 MHz): δ 81.44, 73.24, 25.69, 10.39.
$^1$H NMR (C$_6$D$_6$, 500 MHz): δ 3.68 (dd, J=10, 5 Hz, 1H), 3.58 (dd, J=10, 6 Hz, 1H), 3.41 (quintet, J=6 Hz, 1H), 1.63 (m, 2H), 1.02 (t, J=7.5 Hz, 3H).
M$_n$: 61,400
PDI: 2.0
T$_g$: −76° C.

Polymerization of Racemic Hexene Oxide (Table 1, Entry 3).

Figure 5:
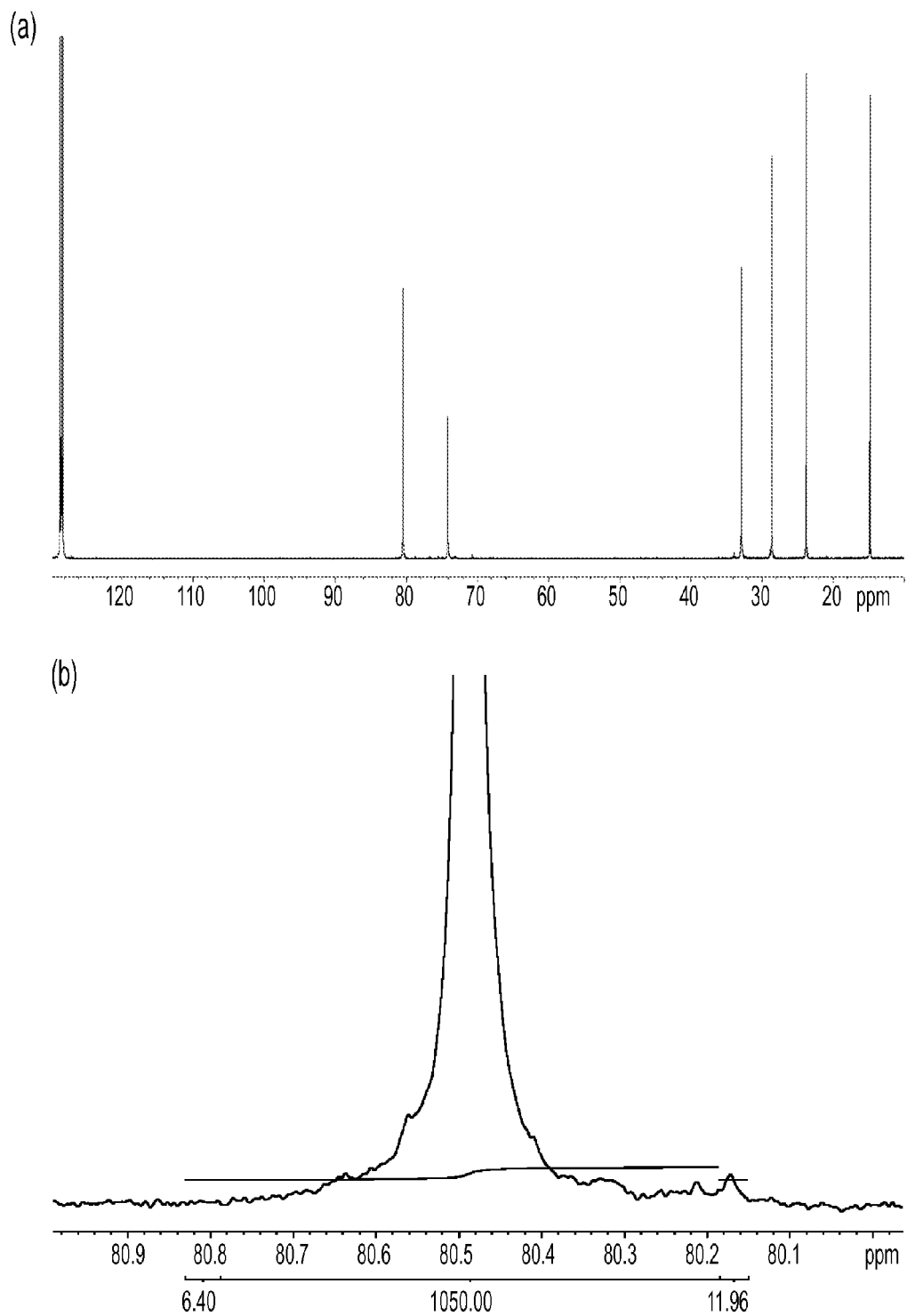
FIG. 5 depicts the $^{13}$C NMR spectra of PHO. a) Full spectrum. b) Methine carbon.

The polymerization procedure was the same as that for propylene oxide except hexene oxide was used. Hexene oxide (0.5325 g, 5.3 mmol) was polymerized with (R,R)(S)-1 (8.6 mg, 0.0075 mmol) and [PPN][OAc] (8.9 mg, 0.0149 mmol) in dry toluene (1.9 mL). After 20 minutes reaction time unreacted hexene oxide was vacuum transferred to a Schlenk tube cooled in liquid nitrogen. The ee of recovered HO was determined by $^1$H NMR spectroscopy using Europium tris[3-(trifluoromethylhydroxymethylene)-(+)-camphorate] as the chiral Schiff reagent in benzene-d$_6$. The NMR peaks were assigned and the absolute stereochemistry was confirmed by obtaining $^1$H NMR spectra of racemic and commercially available (R) hexene oxide using the same Europium tris[3-(trifluoromethylhydroxymethylene)-(+)-camphorate]/benzene-d$_6$ solution. The ee of recovered HO was determined to be 24% (R). Conversion was determined by polymer mass (0.1016 g) to be 19%. A concentrated sample of PHO was made in benzene-d$_6$ for $^{13}$C NMR analysis. Polymer tacticity (FIG. 5): [mm]:[mr+rm]:[rr]=[0.986]:[0.009]:[0.0045]. [m]=0.991. ee$_{(p)}$=99.1%. k$_{rel(p)}$=260.

$^{13}$C NMR (C$_6$D$_6$, 125 MHz): δ 80.49, 74.13, 32.89, 28.60, 23.75, 14.81.
$^1$H NMR (C$_6$D$_6$, 500 MHz): δ 3.79 (dd, J=9.5, 4.5 Hz, 1H), 3.64 (dd, J=9.5, 5 Hz, 1H), 3.53 (quintet, J=5.5 Hz, 1H), 1.52-1.7 (m, 2H), 1.3-1.5 (m, 4H), 0.97 (t, J=7 Hz, 3H).
M$_n$: 76,800
PDI: 2.1
T$_m$: 53° C.
A T$_g$ was not detected.

Polymerization of Racemic Ethyl Glycidyl Ether (Table 1, Entry 4).

Figure 6:
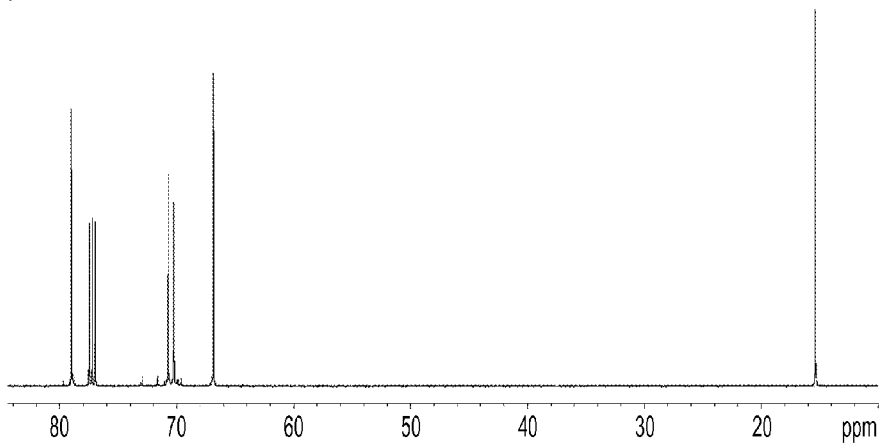
FIG. 6 depicts the $^{13}$C NMR spectra of Poly(Ethyl Glycidyl Ether). a) Full spectrum. b) Methine carbon.
Figure 6:
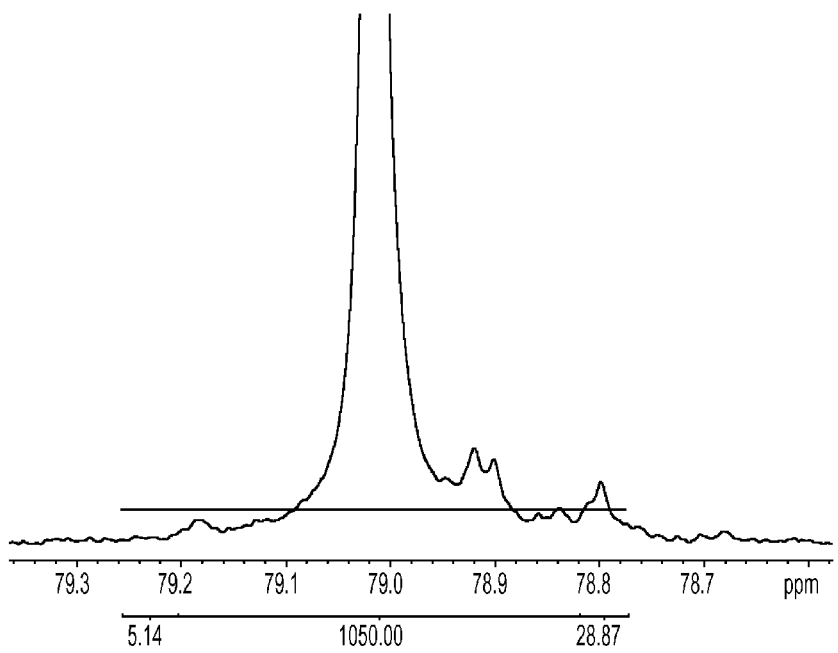

The polymerization procedure was the same as that for propylene oxide except ethyl glycidyl ether was used. Ethyl glycidyl ether (0.8806 g, 8.6 mmol) was polymerized with (R,R)(S)-1 (5.6 mg, 0.0049 mmol) and [PPN][OAc] (5.9 mg, 0.0099 mmol) in dry toluene (4 mL). After 50 minutes reaction time, chloroform (6 mL) was added to the Schlenk tube to stop the polymerization. Due to the relatively high boiling point of ethyl glycidyl ether, the conversion was determined by $^1$H NMR spectroscopy. An aliquot of the polymerization solution was taken and added to an NMR tube containing CDCl$_3$ to determine conversion. Another aliquot was added to a vial containing chloroform, and a sample of this solution was run on the chiral GC to determine the enantiomeric excess of unreacted ethyl glycidyl ether. About 0.2 mL of trace HCl in methanol was added to the remaining polymerization solution to deactivate the catalyst. The polymer solution was transferred to a round bottom flask and concentrated, followed by drying overnight under vacuum on the Schlenk line. Of note, control experiments demonstrated that certain polymerizations may not proceed in chloroform. Based on $^1$H NMR, the conversion to polymer was 24% (only polymer, monomer, and toluene were present in the spectrum). The ee of recovered ethyl glycidyl ether was determined by chiral gas chromatography to be 31%, with t$_R$ (major)' 7.99 min and t$_R$ (minor)' 8.63 min. The conditions for chiral GC separation were: flow, 2.0 mL/min; velocity, 34 cm/sec; pressure, 10 psi; isothermal at 65° C. A concentrated polymer sample was made in benzene-d$_6$ for $^{13}$C NMR analysis. Polymer tacticity (FIG. 6): [mm]:[mr+rm]:[rr]=[0.934]:[0.044]:[0.022]. [m]=0.956. ee$_{(p)}$=95.5%. k$_{rel(p)}$=59.

$^{13}$C NMR (C$_6$D$_6$, 125 MHz): δ 79.02, 70.74, 70.27, 66.84, 15.38.
$^1$H NMR (C$_6$D$_6$, 500 MHz): δ 3.30-3.54 (m, 7H), 1.05 (t, J=6.5 Hz, 3H).
M$_n$: 7,600
PDI: 1.5
T$_g$: −62° C.

Polymerization of Racemic n-Butyl Glycidyl Ether (Table 1, Entry 5).

Figure 7:
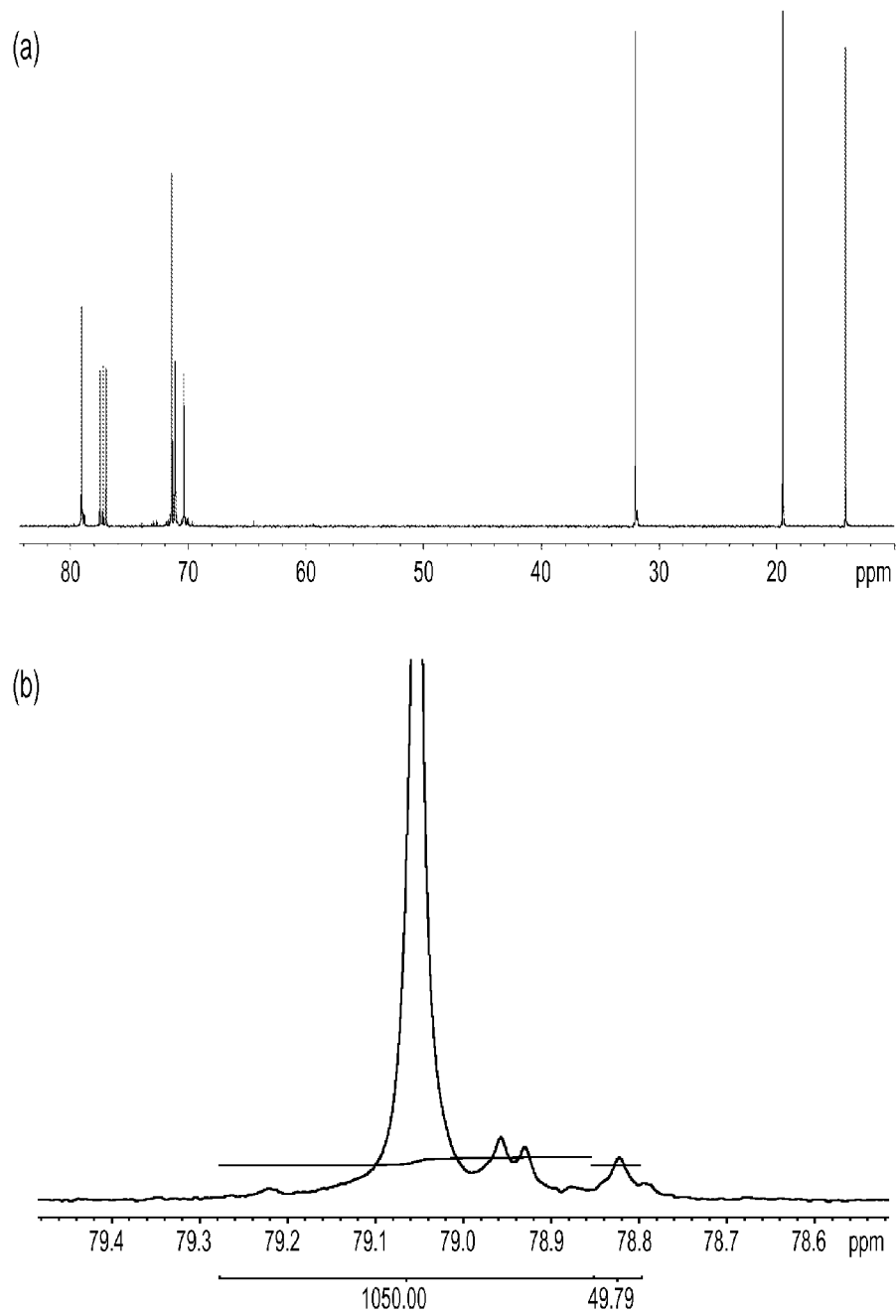
FIG. 7 depicts the $^{13}$C NMR spectra of Poly(n-Butyl Glycidyl Ether). a) Full spectrum. b) Methine carbon.

The polymerization procedure was the same as that for propylene oxide except n-butyl glycidyl ether was used. n-Butyl glycidyl ether (0.9342 g, 7.2 mmol) was polymerized with (R,R)(S)-1 (4.4 mg, 0.0038 mmol) and [PPN][OAc] (4.6 mg, 0.0077 mmol) in dry toluene (2.8 mL). After 64 minutes reaction time, chloroform (6 mL) was added to the Schlenk tube to stop the polymerization. Conversion was determined by $^1$H NMR spectroscopy to be 46% (only polymer, monomer, and toluene were present in the spectrum). The ee of unreacted n-butyl glycidyl ether was determined by chiral gas chromatography to be 77%, with $t_R$ (major)· 26.05 min and $t_R$ (minor)· 26.88 min. The conditions for chiral GC separation were: flow, 2.0 mL/min; velocity, 34 cm/sec; pressure, 10 psi; isothermal at 65° C. for 25 minutes, followed by an increase in temperature by 20° C./min to 140° C. A concentrated polymer sample was made in benzene-$d_6$ for $^{13}$C NMR analysis. Polymer tacticity (FIG. 7): [mm]:[mr+rm]:[rr]=[0.864]: [0.091]:[0.045]. [m]=0.910. ee$_{(p)}$=90.5%. k$_{rel(p)}$=47.

$^{13}$C NMR (CDCl$_3$, 125 MHz): δ 79.05, 71.42, 71.10, 70.37, 31.99, 19.50, 14.14.

$^1$H NMR (CDCl$_3$, 500 MHz): δ 3.38-3.55 (m, 3H), 3.26-3.35 (m, 2H), 1.42 (m, 2H), 1.23 (m, 2H), 0.79 (t, J=7.5 Hz, 3H).

M$_n$: 32,700 PDI: 2.0

T$_g$: −74° C. T$_m$: 18° C.

Polymerization of Racemic Allyl Glycidyl Ether (Table 1, Entry 6).

Figure 8:
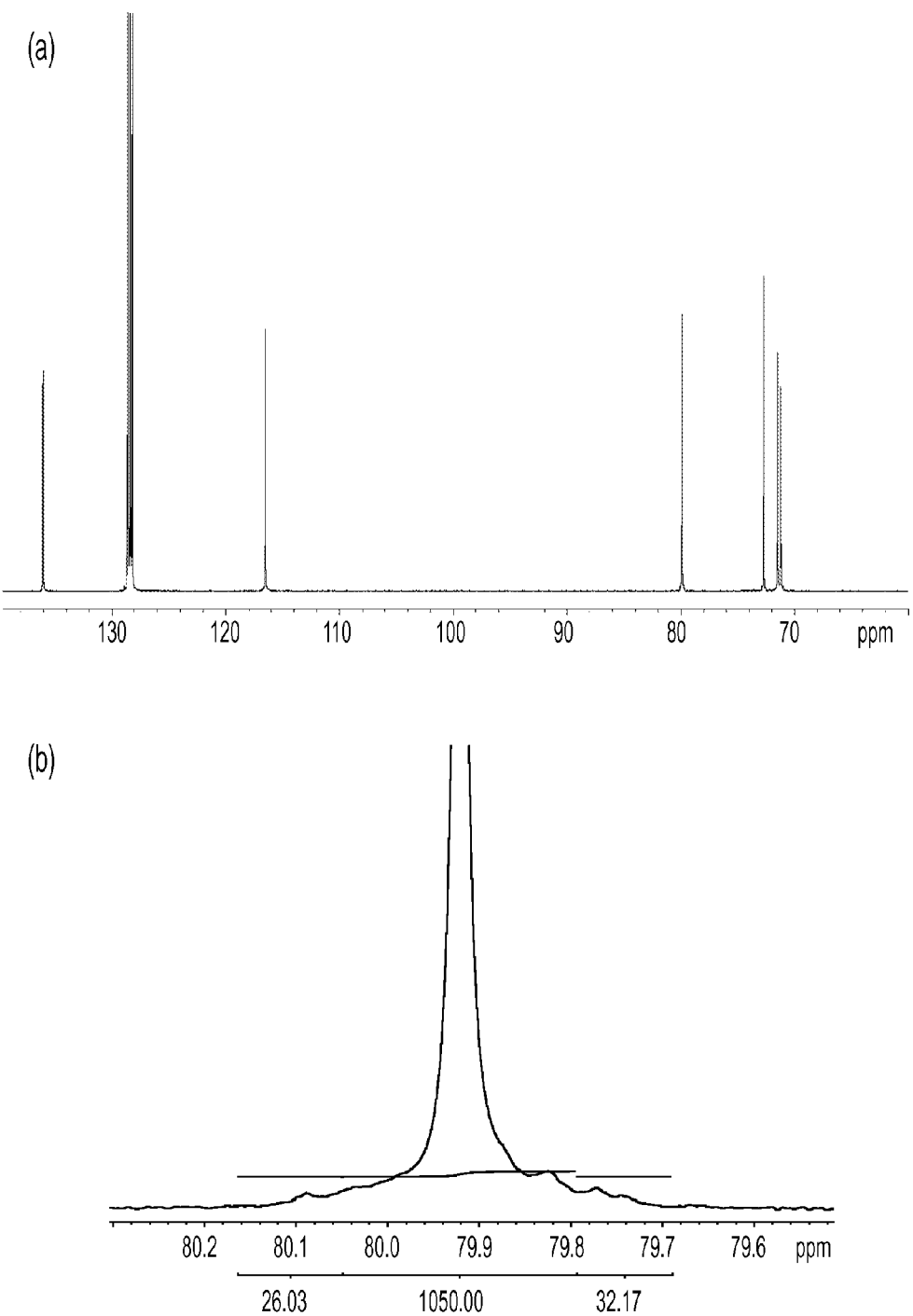
FIG. 8 depicts the $^{13}$C NMR spectra of Poly(Allyl Glycidyl Ether). a) Full spectrum. b) Methine carbon.

The polymerization procedure was the same as that for propylene oxide except allyl glycidyl ether was used. Allyl glycidyl ether (0.9855 g, 8.6 mmol) was polymerized with (R,R)(S)-1 (2.5 mg, 0.0022 mmol) and [PPN][OAc] (2.6 mg, 0.0044 mmol) in dry toluene (16.5 mL). Conversion was determined by $^1$H NMR spectroscopy to be 36% (only polymer, monomer, and toluene were present in the spectrum). The ee of unreacted allyl glycidyl ether was determined by chiral gas chromatography to be 57%, with $t_R$ (major)· 17.11 min and $t_R$ (minor)· 19.07 min. The conditions for chiral GC separation were: flow, 2.0 mL/min; velocity, 34 cm/sec; pressure, 10 psi; isothermal at 65° C. A concentrated polymer sample was made in benzene-$d_6$ for $^{13}$C NMR analysis. Polymer tacticity (FIG. 8): [mm]:[mr+rm]:[rr]=[0.983]:[0.011]: [0.006]. [m]=0.989. ee$_{(p)}$=98.9%. k$_{rel(p)}$=310.

$^{13}$C NMR (C$_6$D$_6$, 125 MHz): δ 136.06, 116.51, 79.92, 72.70, 71.51, 71.22.

$^1$H NMR (C$_6$D$_6$, 500 MHz): δ 5.88 (m, 1H), 5.27 (dd, J=17, 1 Hz, 1H), 5.08 (dd, J=10, 1.5 Hz, 1H), 3.91 (d, J=5 Hz, 2H), 3.80-3.84 (m, 2H), 3.74-3.79 (m, 1H), 3.64 (dd, J=10, 4 Hz, 1H), 3.57 (dd, J=10, 5.5 Hz, 1H).

M$_n$: 106,200 PDI: 1.5

A T$_g$ was not detected, and there was no T$_m$ in the temperature range scanned.

Polymerization of Racemic Furfuryl Glycidyl Ether (Table 1, Entry 7).

The polymerization procedure was the same as that for propylene oxide except furfuryl glycidyl ether was used. Furfuryl glycidyl ether (1.665 g, 10.8 mmol) was polymerized with (R,R)(S)-1 (2.8 mg, 0.0024 mmol) and [PPN][OAc] (2.9 mg, 0.0049 mmol) in dry toluene (18 mL). Conversion was determined by $^1$H NMR spectroscopy to be 41% (only polymer, monomer, and toluene were present in the spectrum).

Figure 9:
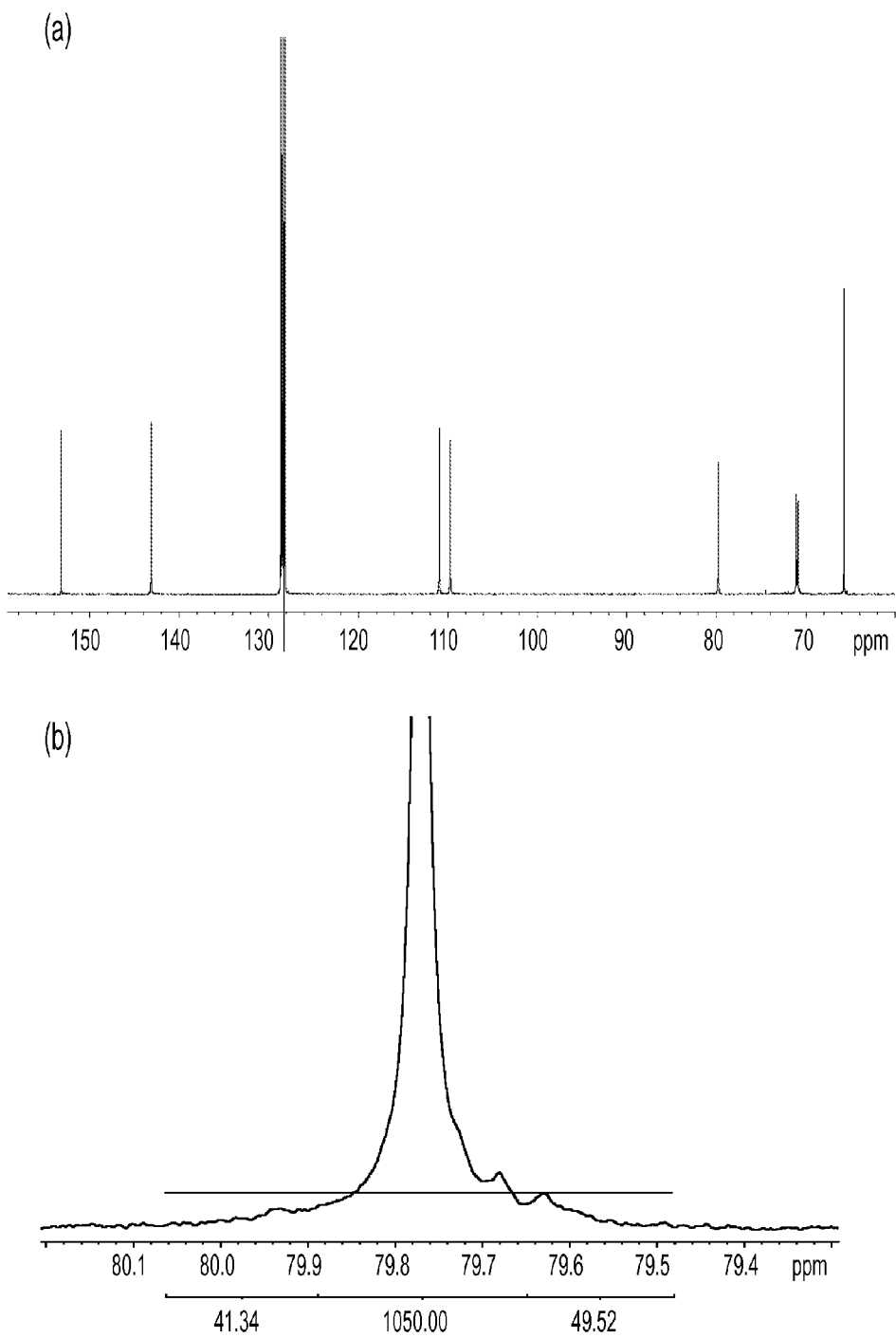
FIG. 9 depicts the $^{13}$C NMR spectra of Poly(Furfuryl Glycidyl Ether). a) Full spectrum. b) Methine carbon.

The ee of unreacted furfuryl glycidyl ether was determined by chiral gas chromatography to be 80%, with $t_R$ (major)=14.73 min and $t_R$ (minor)· 15.17 min. The conditions for chiral GC separation were: flow, 1.6 mL/min; velocity, 31 cm/sec; pressure, 10 psi; isothermal at 115° C. A concentrated polymer sample was made in benzene-$d_6$ for $^{13}$C NMR analysis. Polymer tacticity (FIG. 9): [mm]:[mr+rm]:[rr]=[0.979]:[0.014]: [0.007]. [m]=0.986. ee$_{(p)}$=98.6%.

$^{13}$C NMR (C$_6$D$_6$, 125 MHz): δ 152.76, 142.68, 110.47, 109.26, 79.32, 70.61, 70.41, 65.27.

$^1$H NMR (C$_6$D$_6$, 500 MHz): δ 7.18 (d, J=1 Hz, 1H), 6.19 (d, J=3 Hz, 1H), 6.12 (m, 1H), 4.38 (m, 2H), 3.62-3.76 (m, 4H), 3.54-3.60 (m, 1H). k$_{rel(p)}$=280.

M$_n$: 68,900

PDI: 1.2

T$_g$: −27° C.

Polymerization of Racemic 3,4-Epoxy-1-Butene (Table 1, Entry 8).

Figure 10:
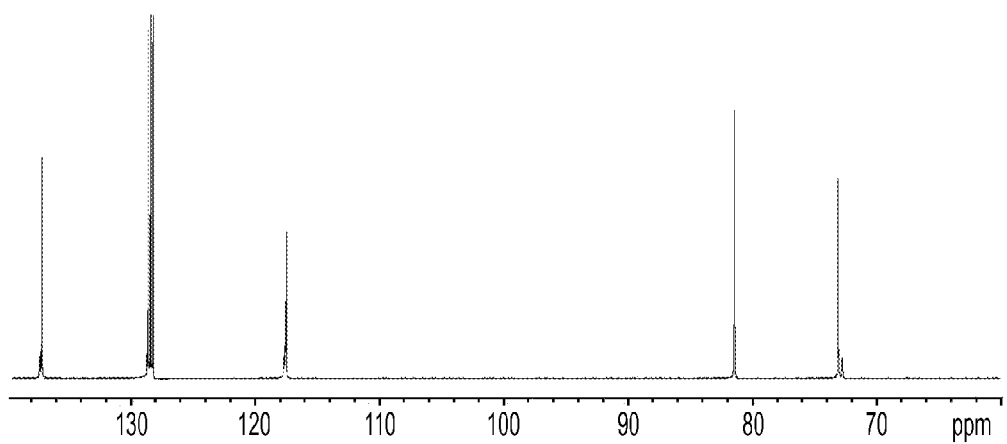
FIG. 10 depicts the $^{13}$C NMR spectra of Poly(3,4-Epoxy-1-Butene). a) Full Spectrum. b) Methylene carbon.
Figure 10:
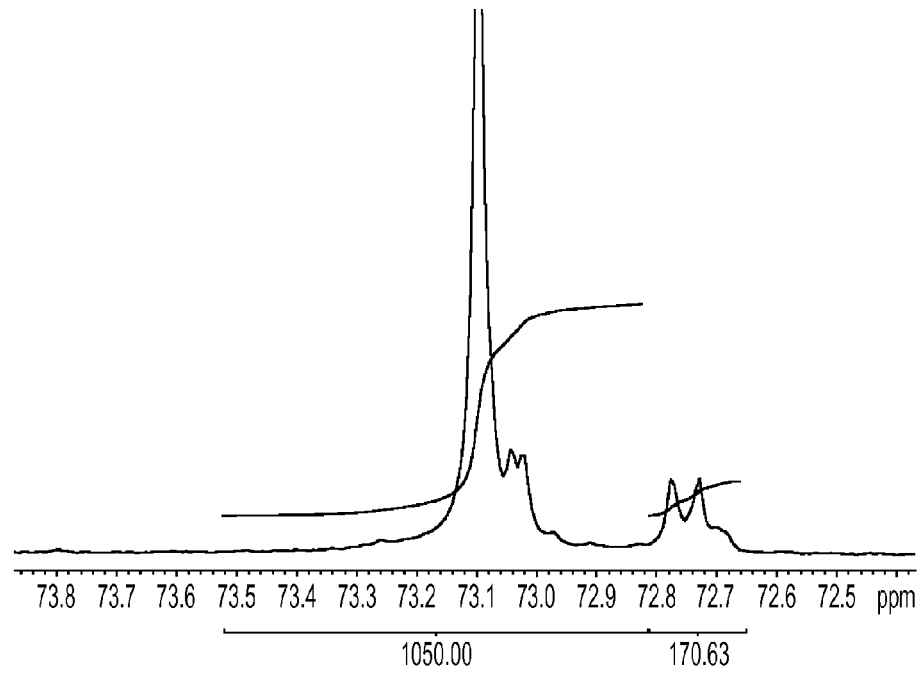

The polymerization procedure was the same as that for propylene oxide except 3,4-epoxy-1-butene was used. 3,4-Epoxy-1-butene (0.5650 g, 8.1 mmol) was polymerized with (R,R)(S)-1 (8.2 mg, 0.0071 mmol) and [PPN][OAc] (8.5 mg, 0.0142 mmol) in dry toluene (3.1 mL). Conversion was determined by $^1$H NMR spectroscopy to be 45% (only polymer, monomer, and toluene were present in the spectrum). The unreacted 3,4-epoxy-1-butene was vacuum transferred to a Schlenk tube cooled in liquid nitrogen. The ee of recovered 3,4-epoxy-1-butene was determined by $^1$H NMR spectroscopy using Europium tris[3-(trifluoromethylhydroxymethylene)-(+)-camphorate] as the chiral Schiff reagent in benzene-$d_6$. The NMR peaks were assigned and the absolute stereochemistry was confirmed by obtaining $^1$H NMR spectra of racemic and (R)-3,4-epoxy-1-butene using the same Europium tris[3-(trifluoromethylhydroxymethylene)-(+)-camphorate]/benzene-$d_6$ solution. (R)-3,4-Epoxy-1-butene was resolved by Jacobsen's hydrolytic kinetic resolution (Schaus et al., J. Am. Chem. Soc., 2002, 124(7), pp 1307). The ee of recovered 3,4-epoxy-1-butene was determined to be 73% (R). A concentrated polymer sample was made in benzene-$d_6$ for $^{13}$C NMR analysis. Polymer tacticity (FIG. 10): [mm]:[mr+rm]:[rr]=[0.581]:[0.280]10.1391. [m]=0.720. ee$_{(p)}$=66.4%. k$_{rel(p)}$=8.

$^{13}$C NMR (C$_6$D$_6$, 125 MHz): δ 137.11, 117.49, 81.41, 73.10.

$^1$H NMR (C$_6$D$_6$, 500 MHz): δ 5.78 (m, 1H), 5.32 (m, 1H), 5.11 (m, 1H), 3.97 (m, 1H), 3.58-3.74 (m, 1H), 3.40-3.50 (m, 1H).

M$_n$: 79,300

PDI: 1.8

T$_g$: −50° C. T$_m$: 62° C.

Polymerization of Racemic 5,6-Epoxy-1-Hexene (Table 1, Entry 9).

Figure 11:
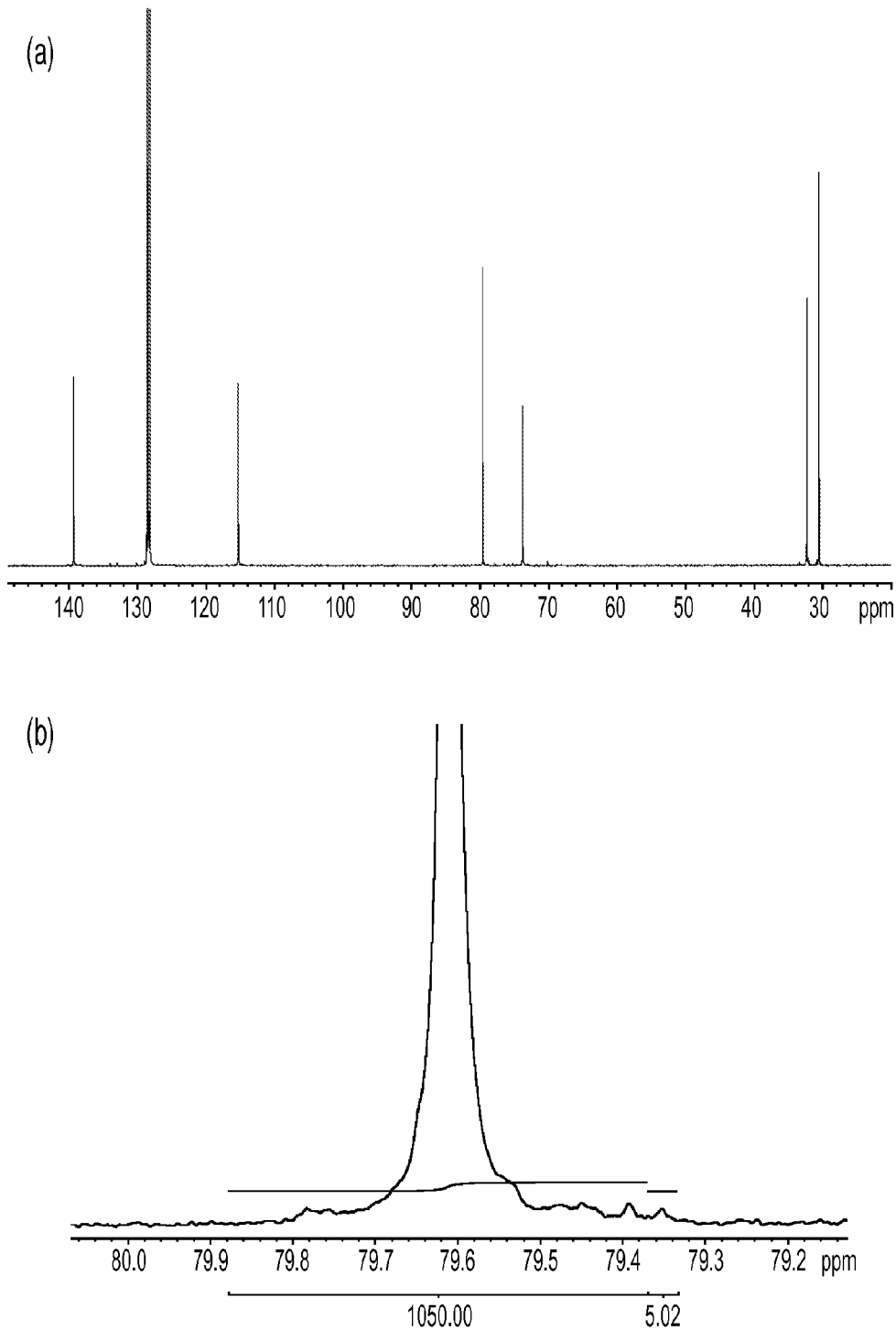
FIG. 11 depicts the $^{13}$C NMR spectra of Poly(5,6-Epoxy-1-Hexene). a) Full spectrum. b) Methine carbon.

The polymerization procedure was the same as that for propylene oxide except 5,6-epoxy-1-hexene was used. 5,6-Epoxy-1-hexene (0.5103 g, 5.4 mmol) was polymerized with (R,R)(S)-1 (8.8 mg, 0.0069 mmol) and [PPN][OAc] (9.1 mg, 0.0152 mmol) in dry toluene (2 mL). Conversion was determined by $^1$H NMR spectroscopy to be 35% (only polymer, monomer, and toluene were present in the spectrum). The ee of 5,6-epoxy-1-butene was determined by chiral gas chromatography to be 53% (R), with $t_R$=23.57 min and $t_S$=24.96 min. The conditions for separation were: flow, 2.6 mL/min; velocity, 36 cm/sec; pressure, 10 psi; isothermal at 35° C. A concentrated polymer sample was made in benzene-$d_6$ for $^{13}$C NMR analysis. Polymer tacticity (FIG. 11): [mm]:[mr+rm]: [rr]=[0.9857]:[0.0095]:[0.0048]. [m]=0.990 ee$_{(p)}$=99.0%. k$_{rel(p)}$=340.

$^{13}$C NMR (C$_6$D$_6$, 125 MHz): δ 138.84, 114.83, 79.15, 73.31, 31.81, 30.06.

$^1$H NMR (C$_6$D$_6$, 500 MHz): δ 5.87 (ddt, J=17, 10, 6.5 Hz, 1H), 5.13 (dd, J=17, 1.5 Hz, 1H), 5.03 (m, 1H), 3.70 (dd, J=9.5, 5 Hz, 1H), 3.56 (dd, J=9.5, 5.5 Hz, 1H), 3.49 (quintet, J=6 Hz, 1H), 2.27 (m, 2H), 1.70 (m, 2H).

M$_n$: 45,700

PDI: 1.9

T$_g$: −69° C.

Polymerization of Racemic Styrene Oxide (Table 1, Entry 10).

Figure 12:
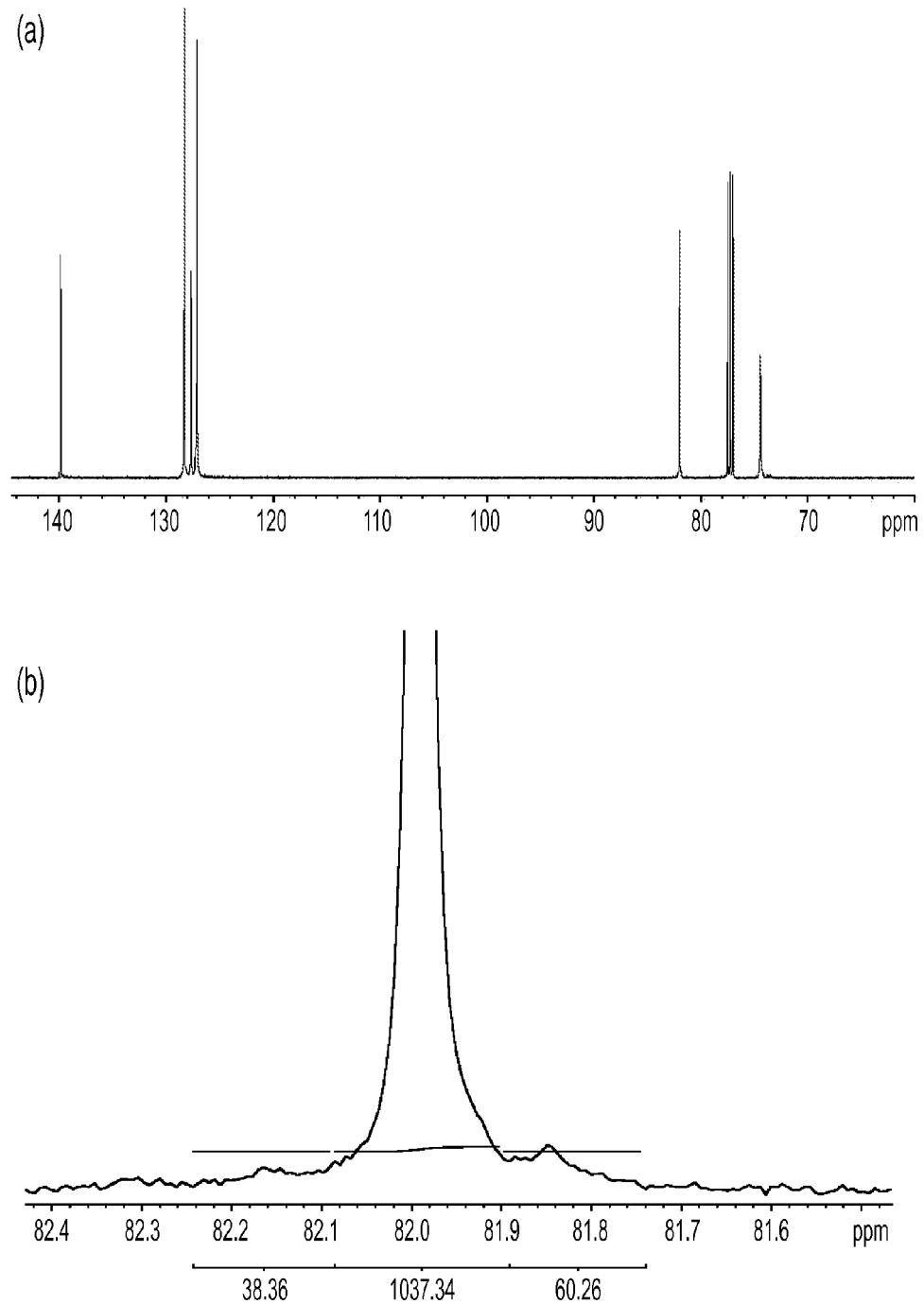
FIG. 12 depicts the $^{13}$C NMR spectra of Poly(Styrene Oxide). a) Full spectrum. b) Methine carbon.

The polymerization procedure was the same as that for propylene oxide except styrene oxide was used, and the polymerization was run neat. Styrene oxide (0.5295 g, 4.4 mmol) was polymerized with (R,R)(S)-1 (4.8 mg, 0.0042 mmol) and [PPN][OAc] (5.0 mg, 0.0084 mmol). Conversion was determined by polymer mass (0.1086 g) to be 20%. The ee of unreacted styrene oxide was determined by chiral gas chromatography to be 26% (R), with t$_S$=16.51 min and t$_R$=16.89 min. The absolute stereoconfiguration was confirmed by running commercially available (R) styrene oxide on the chiral GC. The conditions for separation were: flow, 1.7 mL/min; velocity, 32 cm/sec; pressure, 10 psi; isothermal at 90° C. A concentrated polymer sample was made in CDCl$_3$ for $^{13}$C NMR analysis. Polymer tacticity (FIG. 12): [mm]:[mr+rm]:[rr]=[0.944]:[0.038]:[0.019]. [m]=0.962 ee$_{(p)}$=96.1%. k$_{rel(p)}$=63.

$^{13}$C NMR (CDCl$_3$, 125 MHz): δ 139.84, 128.32, 127.67, 127.13, 81.99, 74.40.

$^1$H NMR (C$_6$D$_6$, 500 MHz): δ 7.26 (m, 2H), 7.14 (m, 2H), 7.07 (m, 1H), 4.51 (dd, J=7.5, 3.5 Hz, 1H), 3.69 (dd, J=10.5, 8 Hz, 1H), 3.47 (dd, J=10, 3.5 Hz, 1H).

M$_n$: 98,800

PDI: 1.9

T$_g$: 50° C.

Polymerization of Racemic 2-(4-Chlorophenyl)-Oxirane (Table 1, Entry 11).

Figure 13:
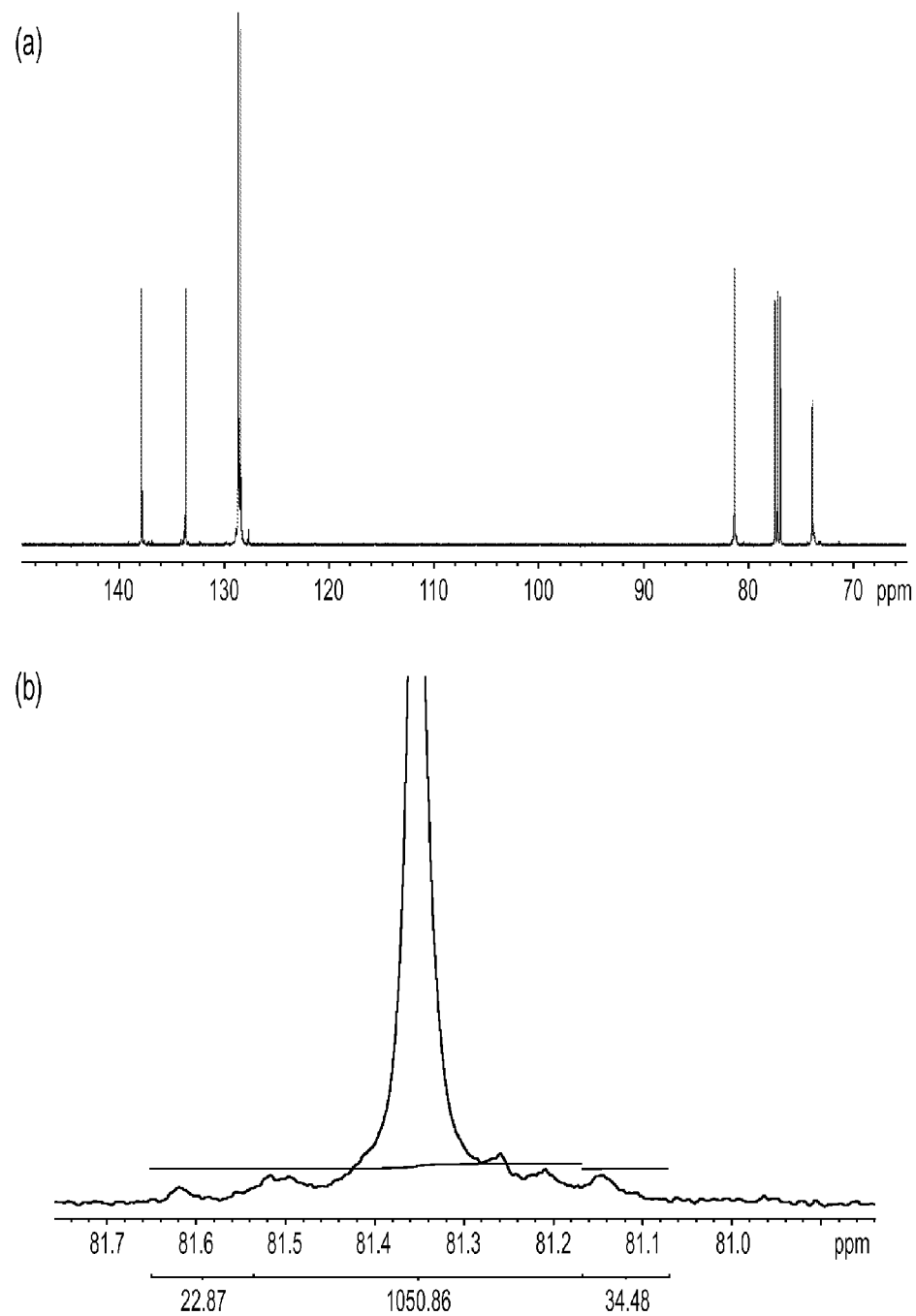
FIG. 13 depicts the $^{13}$C NMR spectra of Poly(2-(4-Chlorophenyl)-Oxirane). a) Full spectrum. b) Methine carbon.

The polymerization procedure was the same as that for propylene oxide except 2-(4-chlorophenyl)-oxirane was used, and the polymerization was run neat in the presence of air. 2-(4-chlorophenyl)-oxirane (0.7382 g, 4.8 mmol) was polymerized with (R,R)(S)-1 (8.9 mg, 0.0077 mmol) and [PPN][OAc] (9.3 mg, 0.0156 mmol). Conversion was determined by $^1$H NMR spectroscopy to be 21%. The ee of unreacted 2-(4-chlorophenyl)-oxirane was determined by chiral gas chromatography to be 26% (R), with t$_S$=31.81 min and t$_R$=31.99 min. The conditions for separation were: flow, 1.7 mL/min; velocity, 32 cm/sec; pressure, 10 psi; isothermal at 90° C. for 25 min, followed by increasing temperature by 20° C./min to 140° C. A concentrated polymer sample was made in CDCl$_3$ for $^{13}$C NMR analysis. Polymer tacticity (FIG. 13): [mm]:[mr+rm]:[rr]=[0.971]:[0.019]:[0.0095].

[m]=0.980 ee$_{(p)}$=97.9%. k$_{rel(p)}$=120.

$^{13}$C NMR (CDCl$_3$, 125 MHz): δ 137.85, 133.67, 128.64, 128.41, 81.35, 73.94.

$^1$H NMR (C$_6$D$_6$, 125 MHz): δ 7.14-7.18 (m, 2H), 6.96-7.0 (m, 2H), 4.27-4.33, (m, 1H), 3.44-3.50 (m, 1H), 3.26-3.32 (m, 1H).

M$_n$: 44,500

PDI: 2.5

T$_g$: 63° C.

Polymerization of Racemic 1,1,1-trifluoro-2,3-epoxypropane (Table 1, Entry 12).

Figure 14:
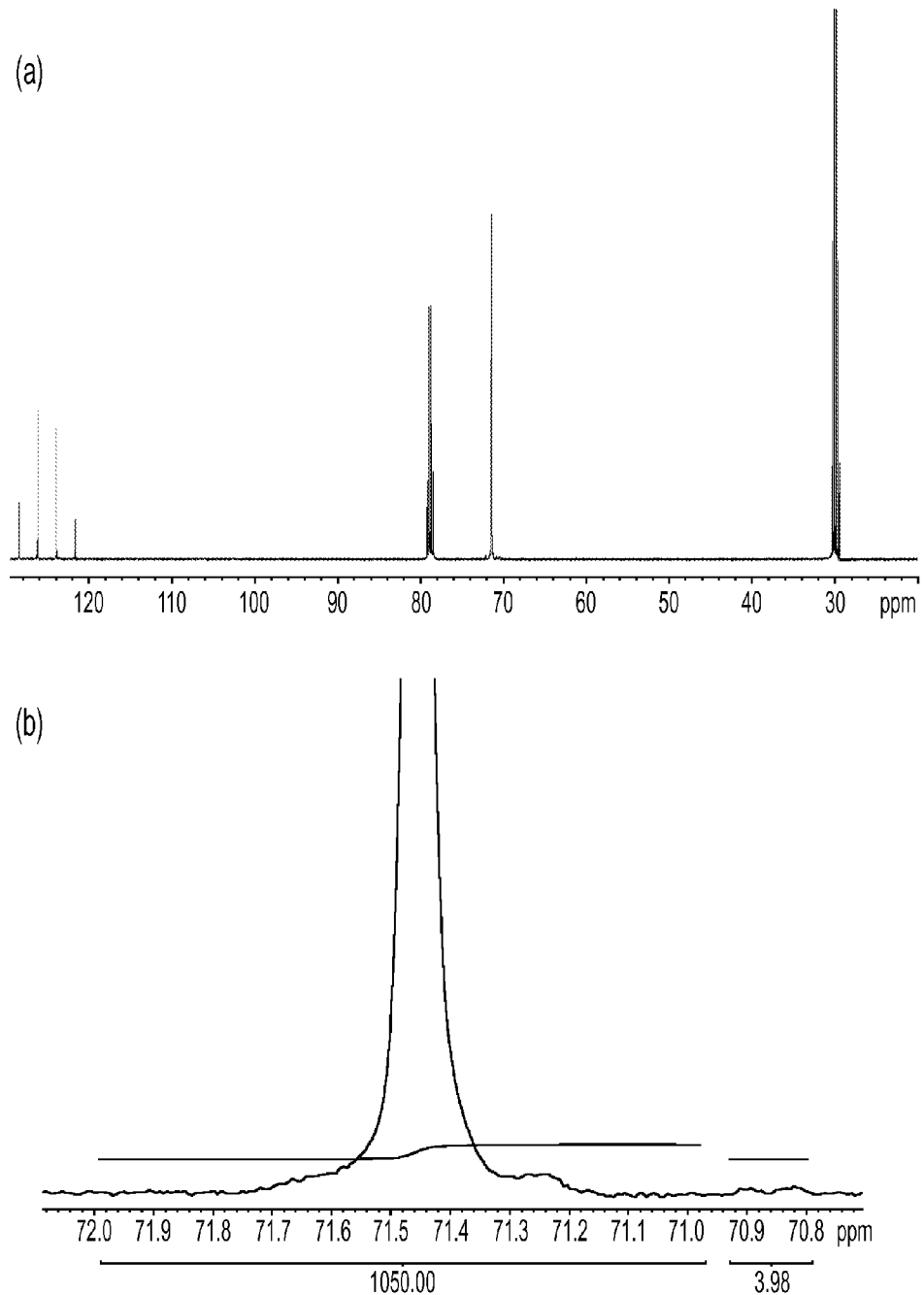
FIG. 14 depicts the $^{13}$C NMR spectra of Poly(1,1,1-Trifluoro-2,3-Epoxypropane). a) Full spectrum. b) Methylene carbon.

The polymerization procedure was the same as that for propylene oxide except 1,1,1-trifluoro-2,3-epoxypropane was used, and the polymerization was run neat. 1,1,1-Trifluoro-2,3-epoxypropane (1.790 g, 16.0 mmol) was polymerized with (R,R)(S)-1 (10.3 mg, 0.0089 mmol) and [PPN][OAc] (10.7 mg, 0.0179 mmol). After 2 minutes reaction time the unreacted 1,1,1-trifluoro-2,3-epoxypropane was vacuum transferred to a Schlenk tube cooled in liquid nitrogen. Conversion was determined by polymer mass (0.6657 g) to be 37%. The ee of unreacted 1,1,1-trifluoro-2,3-epoxypropane was determined by optical rotation to be 53% ee of the (S) enantiomer, with $[α]^{24}_D$=−6.463° (c=5.88, CHCl$_3$), by comparison with literature reports. [>99% ee (S), $[α]^{24}_D$=12.3° (c=8.4, CHCl$_3$)]. A concentrated polymer sample was made in acetone-d$_6$ for $^{13}$C NMR analysis. Polymer tacticity (FIG. 14): [mm]:[mr+rm]:[rr]=[0.987]:[0.0084]:[0.0042]. [m]=0.9916 ee$_{(p)}$=99.2%. k$_{rel(p)}$=430.

$^{13}$C NMR (Acetone-d$_6$, 125 MHz): δ 125.0 (quartet, J=2245, 1122 Hz, CF$_3$), 78.80 (quartet, J=237, 121 Hz, CHCF$_3$), 71.46.

$^1$H NMR (Acetone-d$_6$, 500 MHz): δ 4.35 (m, 1H), 4.21 (dd, J=10.5, 3 Hz, 1H), 4.05 (dd, J=10.5, 7.5 Hz, 1H).

T$_m$: 121° C.

VIII. Synthesis of Isotactic Polyethers using Racemic Catalyst.

Representative Procedure for the Synthesis of Isotactic Polyethers.

Synthesis of PPO (Table 2, Entry 1).

Figure 15:
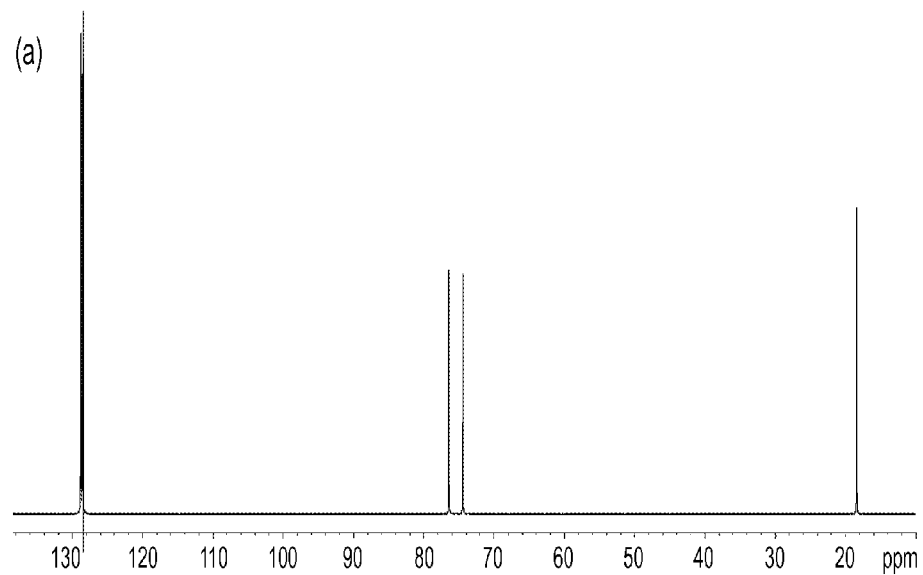
FIG. 15 depicts the $^{13}$C NMR spectra of PPO. a) Full spectrum. b) Methine carbon.
Figure 15:
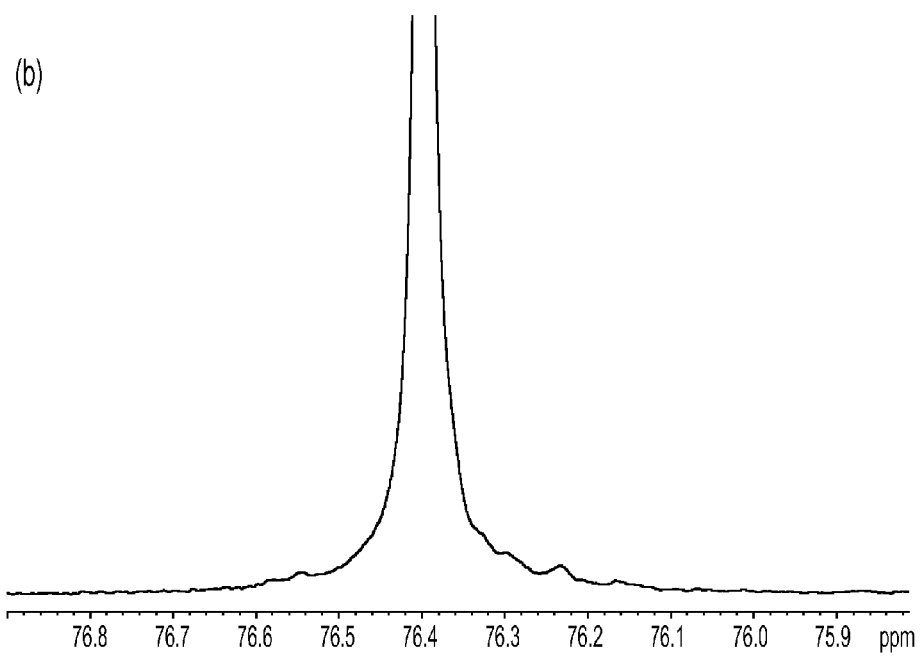

In a dry box under a nitrogen atmosphere, (R,R)(S)-1 and (S,S)(R)-1 were dissolved in a 50:50 ratio in dry toluene to make a stock solution of racemic catalyst (18.3 mg of (R,R)(S)-1 and 18.3 mg of (S,S)(R)-1 in 7.5 mL of toluene). The calculated amount of racemic catalyst solution (2 mg of racemic catalyst, 0.0017 mmol, 0.41 mL of the solution) and [PPN]OAc (2.1 mg, 0.0035 mmol) were added to a 4 mL vial containing a stir bar. PO was previously cooled to −24° C. in a freezer in the dry box. PO (0.1 g, 1.7 mmol) was added by syringe to the vial, and dry toluene (1.2 mL) was added to bring the concentration of PO to 1M in toluene. The 4 mL vial was sealed under nitrogen with a Teflon cap, and then brought out of the dry box to stir at 0° C. in an ice bath. After 3.5 hrs, conversion was determined to be >99% to PPO by $^1$H NMR analysis. The crude polymer solution was then concentrated under vacuum overnight. 50 mg of dried polymer was dissolved in 0.5 mL of benzene-d$_6$ for $^{13}$C NMR analysis. The $^{13}$C NMR spectrum was taken over 2 hours, with 2000+ scans. Polymer tacticity (FIG. 15): %[mm] triad=>99%. Peaks corresponding to error in polymer stereoconfiguration ([mr], [rm], [rr]) were not detected by $^{13}$C NMR.

$^{13}$C NMR (C$_6$D$_6$, 125 MHz): δ 76.40, 74.43, 18.41.

$^1$H NMR (C$_6$D$_6$, 500 MHz): δ 3.57 (m, 2H), 3.40 (m, 1H), 1.17 (d, J=5 Hz, 3H).

M$_n$: 86, 800 PDI: 1.6

T$_m$: 67° C.

A T$_g$ was not detected.

TABLE 2

Synthesis of Isotactic Polyethers.

| Entry | Epoxide | Time (hrs) | Conv. (%) | % [mm] triad | Mn | PDI | Tg (° C.) | Tm (° C.) |
|---|---|---|---|---|---|---|---|---|
| 1 | methyl oxirane | 3.5 | >99 | >99 | 86,800 | 1.6 | ND | 67 |
| 2 | ethyl oxirane | 38 | >99 | >99 | 183,000 | 1.6 | −70 | 22 |
| 3 | butyl oxirane | 15 | >99 | >99 | 282,000 | 1.5 | ND | 57 |
| 4 | vinyl oxirane | 21 | >99 | 73 | 200,000 | 1.6 | −46 | 66 |
| 5 | butoxymethyl oxirane | 84 | >99 | 94 | 105,000 | 1.9 | −77 | 21 |
| 6 | allyloxymethyl oxirane | 3.5 | >99 | 97 | 137,000 | 1.6 | −74 | — |
| 7 | (tBuMe2SiO)methyl oxirane | 13 | >99 | 91 | 406,000 | 1.5 | −36 | 30 |
| 8 | phenoxymethyl oxirane | 0.5 | >99 | >99 | 105,000 | 1.5 | 112 | 193 |
| 9 | benzoyloxymethyl oxirane | 12 | >99 | 93 | 69,200 | 1.5 | 16 | — |
| 10 | allyloxycarbonyloxymethyl oxirane | 2 | >99 | 90 | 65,000 | 1.6 | 17 | — |
| 11 | phenyl oxirane | 5 | >99 | 96 | 97,700 | 1.7 | 49 | — |
| 12 | 4-fluorophenyl oxirane | 12 | >99 | 98 | 120,500 | 1.6 | 50 | 196 |
| 13 | trifluoromethyl oxirane | 14.5 | >99 | 98 | | | ND | 119 |

Synthesis of PBO (Table 2, Entry 2).

The polymerization procedure was the same as that for propylene oxide, except butene oxide was used. Racemic catalyst solution (1.6 mg of racemic catalyst, 0.0014 mmol) and [PPN]OAc (1.7 mg, 0.0028 mmol) were added to a 4 mL vial containing a stir bar. BO was previously cooled to −24°

Figure 16:
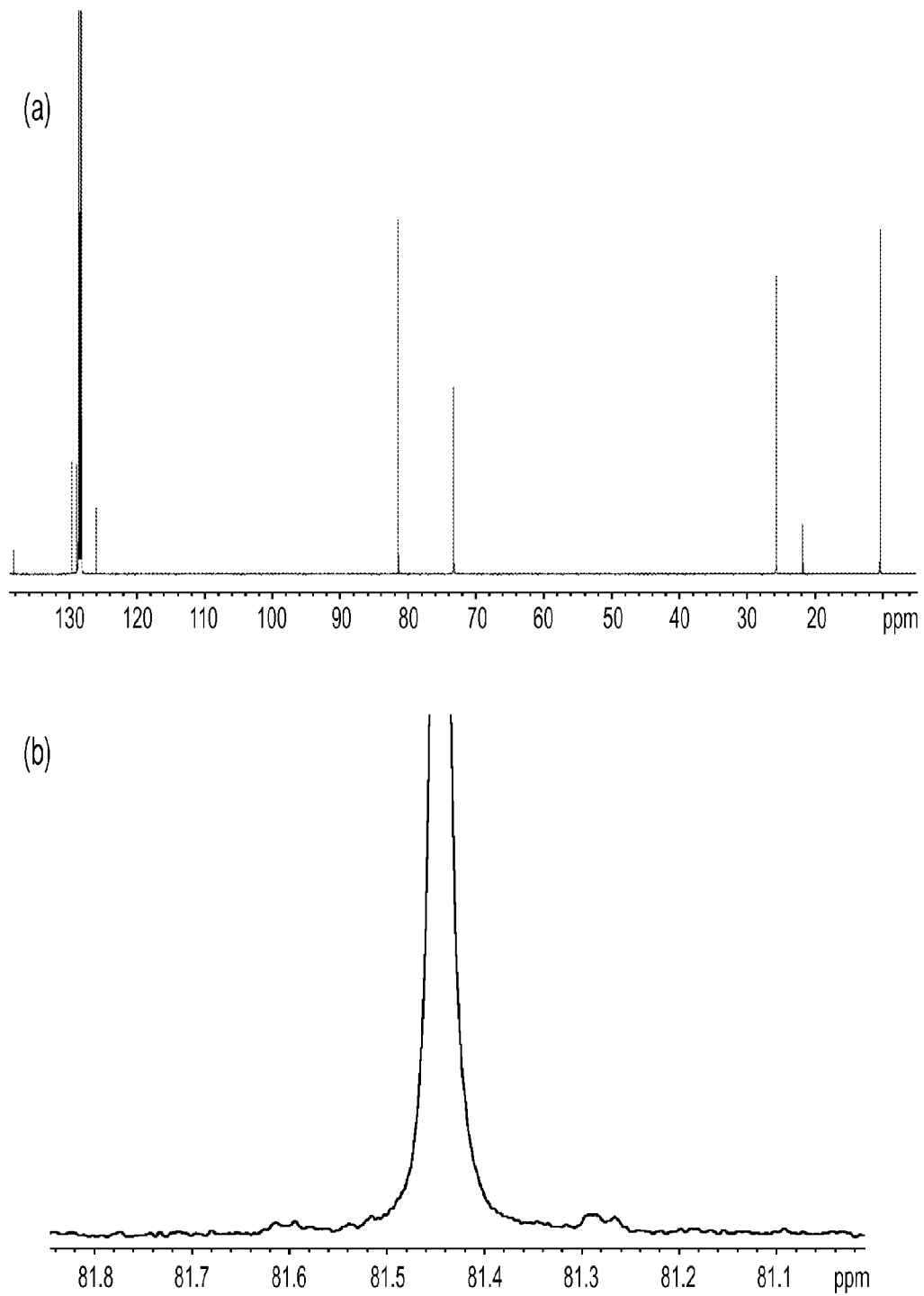
FIG. 16 depicts the $^{13}$C NMR spectra of PBO. a) Full spectrum. Note: residual toluene is present in the spectrum. b) Methine carbon.

C. in a freezer in the dry box. BO (0.1 g, 1.4 mmol) was added by syringe to the vial, and dry toluene (0.94 mL) was added to bring the concentration of BO to 1 M in toluene. Conversion was determined to be >99% to PBO by $^1$H NMR analysis. The crude polymer solution was then concentrated under vacuum overnight. Polymer tacticity (FIG. 16): %[mm] triad=>99%. Note: small peaks due to toluene are present in the spectrum. Peaks corresponding to error in polymer stereoconfiguration ([mr], [rm], [rr]) were not detected by $^{13}$C NMR.

$^{13}$C NMR (C$_6$D$_6$, 125 MHz): δ 81.45, 73.26, 25.70, 10.39. (toluene: δ 138.22, 129.66, 128.90, 126.03, 21.77.)

$^1$H NMR (C$_6$D$_6$, 500 MHz): δ 3.67 (dd, J=9.5, 4.5 Hz, 1H), 3.57 (dd, J=9.5, 6 Hz, 1H), 3.40 (quintet, J=5.5 Hz, 1H), 1.55-1.69 (m, 2H), 1.02 (t, J=7.5 Hz, 3H).

M$_n$: 183,000
PDI: 1.6
T$_g$: −70° C. T$_m$: 22° C.

Synthesis of PHO (Table 2, Entry 3).

Figure 17:
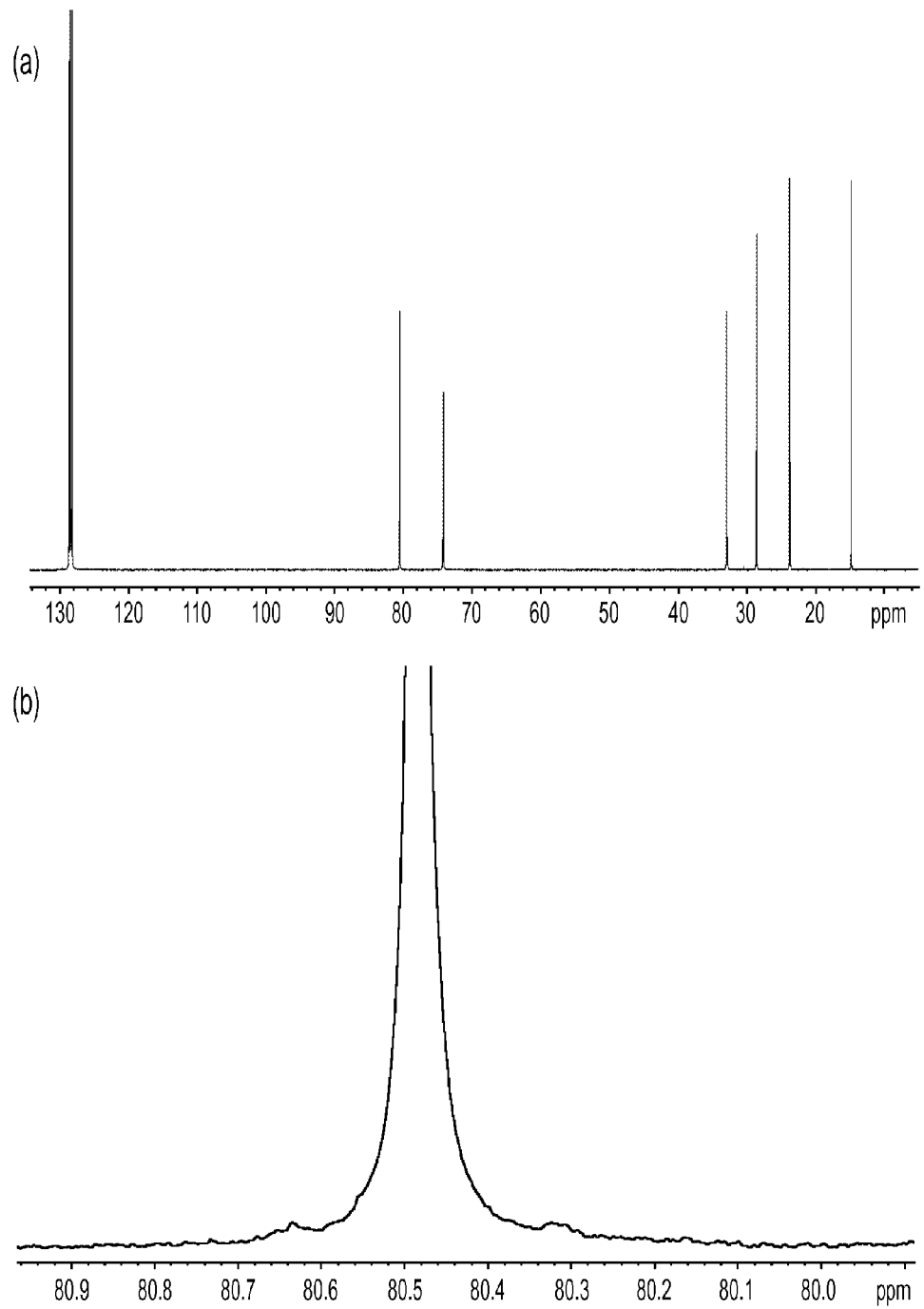
FIG. 17 depicts the $^{13}$C NMR spectra of PHO. a) Full spectrum. b) Methine carbon.

The polymerization procedure was the same as that for propylene oxide, except hexene oxide was used. Racemic catalyst solution (1.2 mg of racemic catalyst, 0.001 mmol) and [PPN]OAc (1.2 mg, 0.002 mmol) were added to a 4 mL vial containing a stir bar. HO was previously cooled to −24° C. in a freezer in the dry box. HO (0.1 g, 1.0 mmol) was added by syringe to the vial, and dry toluene (0.64 mL) was added to bring the concentration of HO to 1 M in toluene. Conversion was determined to be >99% to PHO by $^1$H NMR analysis. The crude polymer solution was then concentrated under vacuum overnight. Polymer tacticity (FIG. 17): %[mm] triad=>99%. Peaks corresponding to error in polymer stereoconfiguration [mr], [rm], [rr]) were not detected by $^{13}$C NMR.

$^{13}$C NMR (C$_6$D$_6$, 125 MHz): δ 80.49, 74.15, 32.91, 28.60, 23.75, 14.81.

$^1$H NMR (C$_6$D$_6$, 500 MHz): δ 3.79 (dd, J=9.5, 4 Hz, 1H), 3.65 (m, 1H), 3.54 (m, 1H), 1.52-1.70 (m, 4H), 1.34-1.50 (m, 2H), 0.97 (t, J=7.5 Hz, 3H).

M$_n$: 282,000
PDI: 1.5
T$_m$: 57° C.
A T$_g$ was not detected.

Synthesis of Poly(3,4-Epoxy-1-butene) (Table 2, Entry 4).

Figure 18:
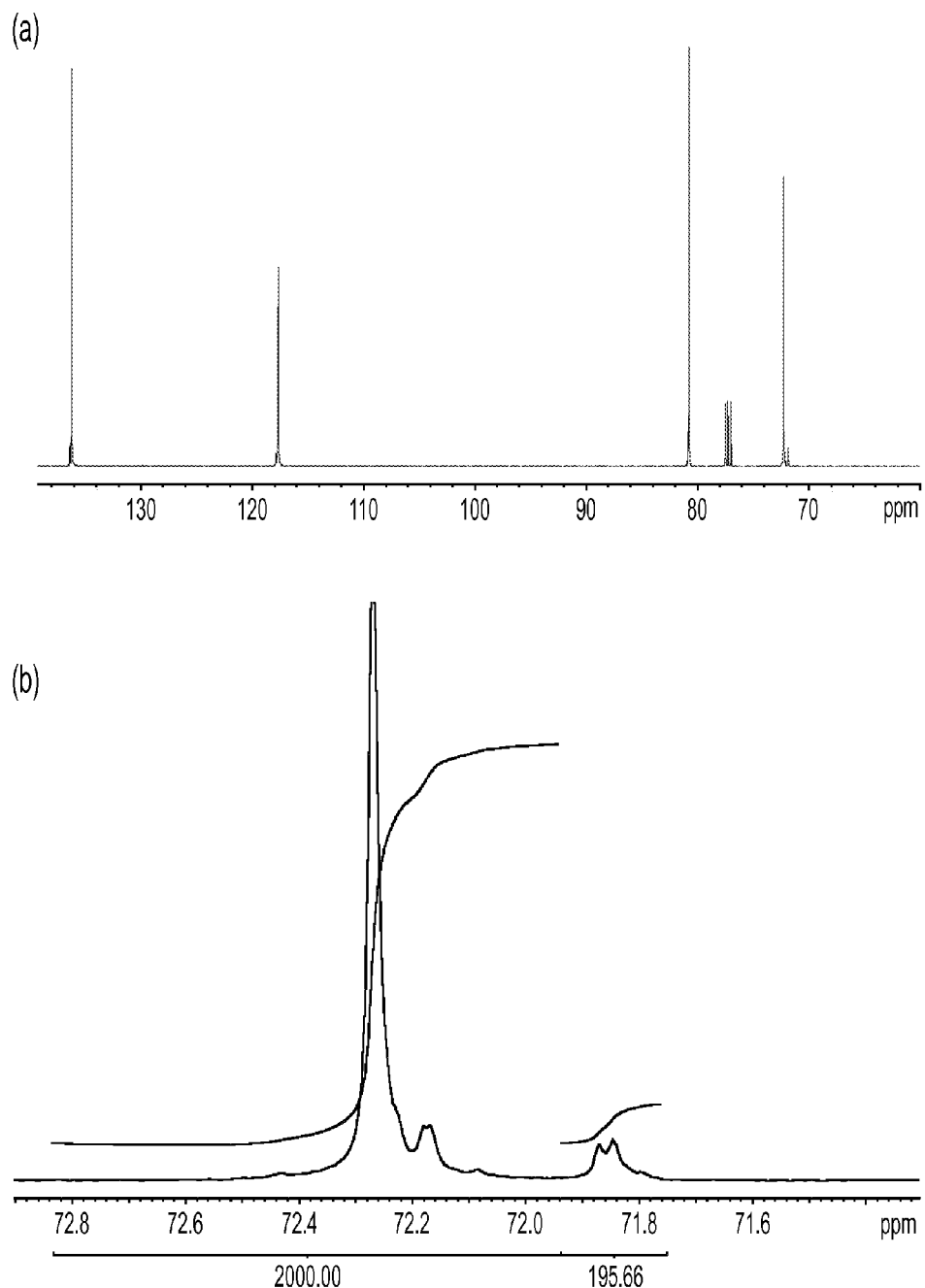
FIG. 18 depicts the $^{13}$C NMR spectra of Poly(3,4-Epoxy-1-Butene). a) Full spectrum. b) Methylene carbon.

The polymerization procedure was the same as that for propylene oxide, except 3,4-epoxy-1-butene was used. Racemic catalyst (8.2 mg, 0.0071 mmol) and [PPN]OAc (8.6 mg, 0.0144 mmol) were added to a 4 mL vial containing a stir bar. 4-Epoxy-1-butene (1 g, 14.3 mmol), previously cooled to −24° C. in a freezer in the dry box, was added by syringe to the vial. Dry toluene (1.7 mL) was added to bring the concentration of 3,4-epoxy-1-butene to 1M in toluene. Conversion was determined to be >99% to poly(3,4-epoxy-1-butene) by $^1$H NMR analysis. The crude polymer solution was then concentrated under vacuum overnight. Polymer tacticity (FIG. 18): [mm]:[mr+nn]:[n]=[0.733]:[0.178]:[0.089]. %[mm] triad=73.3%.

$^{13}$C NMR (CDCl$_3$, 125 MHz): δ 136.22, 117.64, 80.84, 72.27.

$^1$H NMR (CDCl$_3$, 500 MHz): δ 5.62 (ddt, J=13, 10, 7 Hz, 1H), 5.18 (m, 1H), 5.09 (m, 1H), 3.81 (m, 1H), 3.47 (dd, J=10.5, 6.5 Hz, 1H), 3.30 (dd, J=15.5, 4.5 Hz, 1H).

M$_n$: 200,000
PDI: 1.6
T$_g$: −46° C. T$_m$: 66° C.

Synthesis of Poly(n-Butyl Glycidyl Ether) (Table 2, Entry 5).

Figure 19:
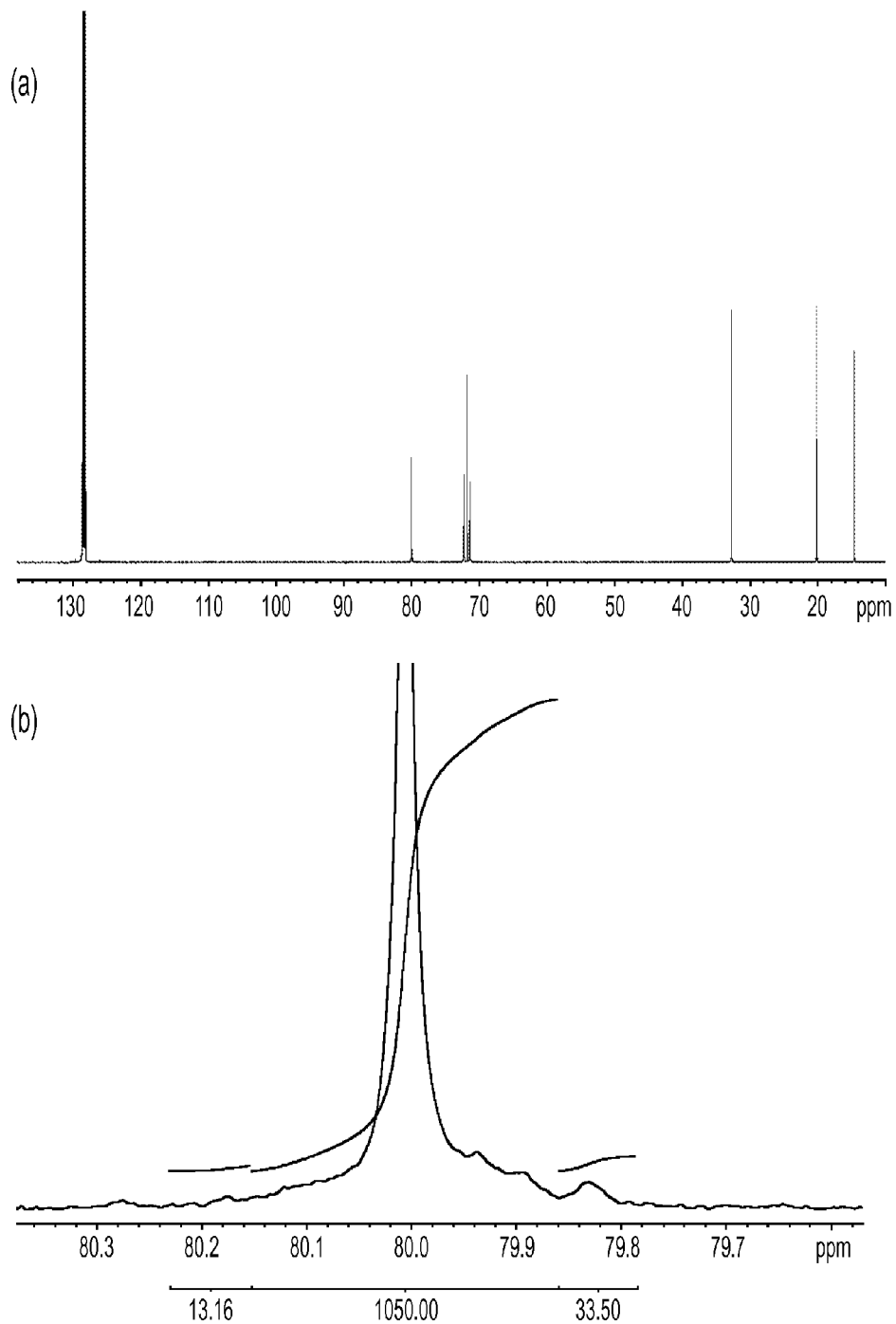
FIG. 19 depicts the $^{13}$C NMR spectra of Poly(n-Butyl Glycidyl Ether). a) Full spectrum. b) Methine carbon.

The polymerization procedure was the same as that for propylene oxide, except n-butyl glycidyl ether was used. Racemic catalyst solution (1.8 mg of racemic catalyst, 0.0016 mmol) and [PPN]OAc (1.8 mg, 0.003 mmol) were added to a 4 mL vial containing a stir bar. n-Butyl glycidyl ether (0.2 g, 1.5 mmol), previously cooled to −24° C. in a freezer in the dry box, was added by syringe to the vial. Dry toluene (0.96 mL) was added to bring the concentration of n-butyl glycidyl ether to 1 M in toluene. Conversion was determined to be >99% to poly(n-butyl glycidyl ether) by $^1$H NMR analysis. The crude polymer solution was then concentrated under vacuum overnight. Polymer tacticity (FIG. 19): [mm]:[mr+rm]:[rr]= [0.944]:[0.037]:[0.019]. %[mm] triad=94.4%.

$^{13}$C NMR (C$_6$D$_6$, 125 MHz): δ 80.01, 32.76, 20.18, 14.58.

$^1$H NMR (C$_6$D$_6$, 500 MHz): δ 3.78-3.90 (m, 3H), 3.68 (dd, J=10.5, 4.5 Hz, 1H), 3.60 (dd, J=9.5, 5.5 Hz, 1H), 3.41 (t, J=6.5 Hz, 2H), 1.58 (m, 2H), 1.41 (m, 2H), 0.93 (t, J=7 Hz, 3H).

M$_n$:105,000
PDI: 1.9
T$_g$: −77° C. T$_m$: 21° C.

Synthesis of Poly(Allyl Glycidyl Ether) (Table 2, Entry 6).

Figure 20:
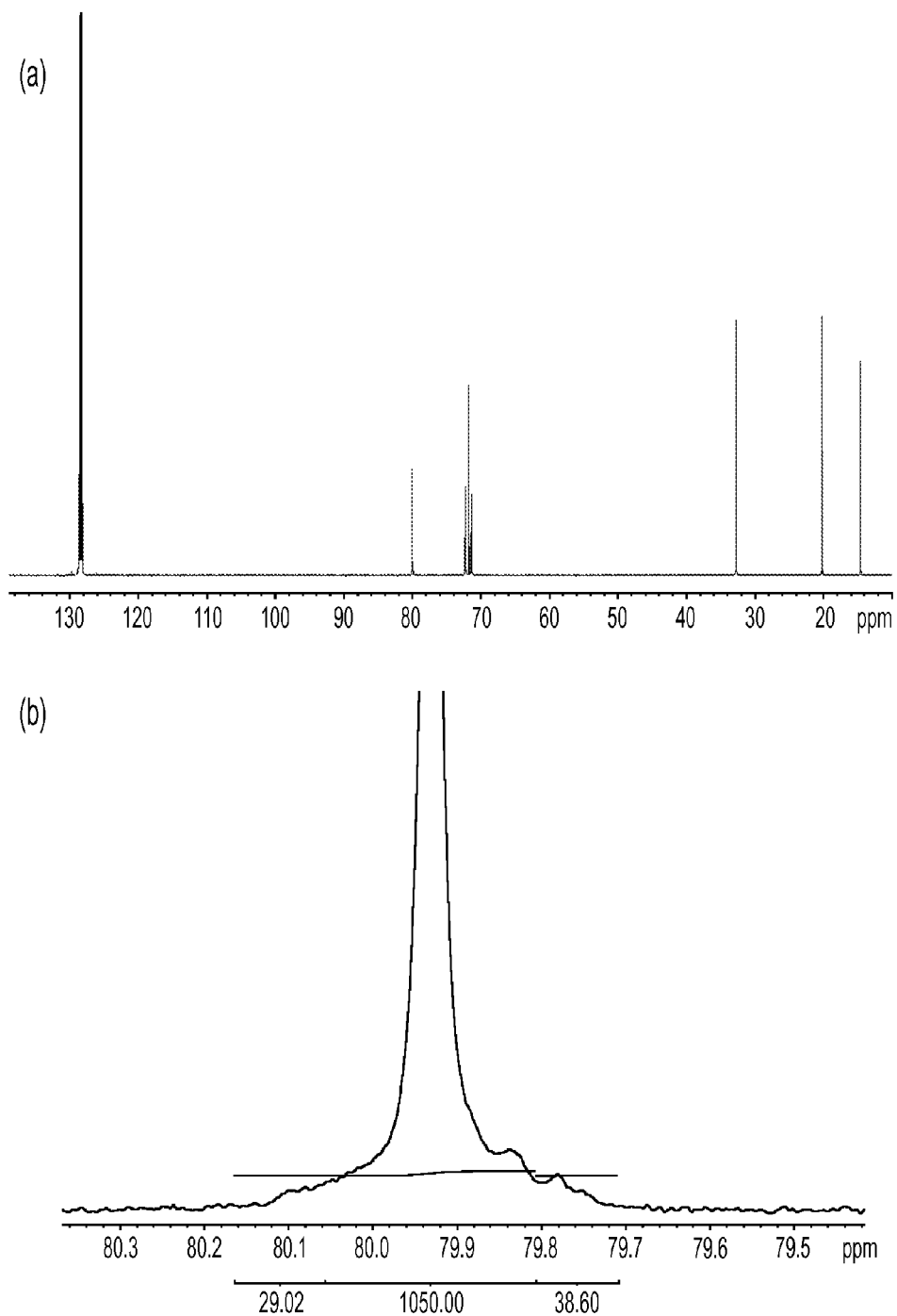
FIG. 20 depicts the $^{13}$C NMR spectra of Poly(Allyl Glycidyl Ether). a) Full spectrum. b) Methine carbon.

The polymerization procedure was the same as that for propylene oxide, except allyl glycidyl ether was used. Racemic catalyst solution (2.0 mg of racemic catalyst, 0.0017 mmol) and [PPN]OAc (2.1 mg, 0.0035 mmol) were added to a 4 mL vial containing a stir bar. Allyl glycidyl ether (0.2 g, 1.8 mmol), previously cooled to −24° C. in a freezer in the dry box, was added by syringe to the vial. Dry toluene (1.1 mL) was added to bring the concentration of allyl glycidyl ether to 1 M in toluene. Conversion was determined to be >99% to poly(allyl glycidyl ether) by $^1$H NMR analysis. The crude polymer solution was then concentrated under vacuum overnight. Polymer tacticity (FIG. 20): [mm]:[mr+rm]:[rr]= [0.974]:[0.017]:[0.009]. %[mm] triad=97.4%.

$^{13}$C NMR (C$_6$D$_6$, 125 MHz): δ 135.99, 116.43, 79.85, 72.62, 71.44, 71.15.

$^1$H NMR (C$_6$D$_6$, 500 MHz): δ 5.91 (m, 1H), 5.28 (m, 1H), 5.10 (m, 1H), 3.90-3.95 (m, 2H), 3.74-3.86 (m, 3H), 3.54-3.68 (m, 2H).

M$_n$:137,000
PDI: 1.6
T$_g$: −74° C.

Synthesis of Poly(tert-Butyl-dimethylsilyl Glycidyl Ether) (Table 2, Entry 7).

Figure 21:
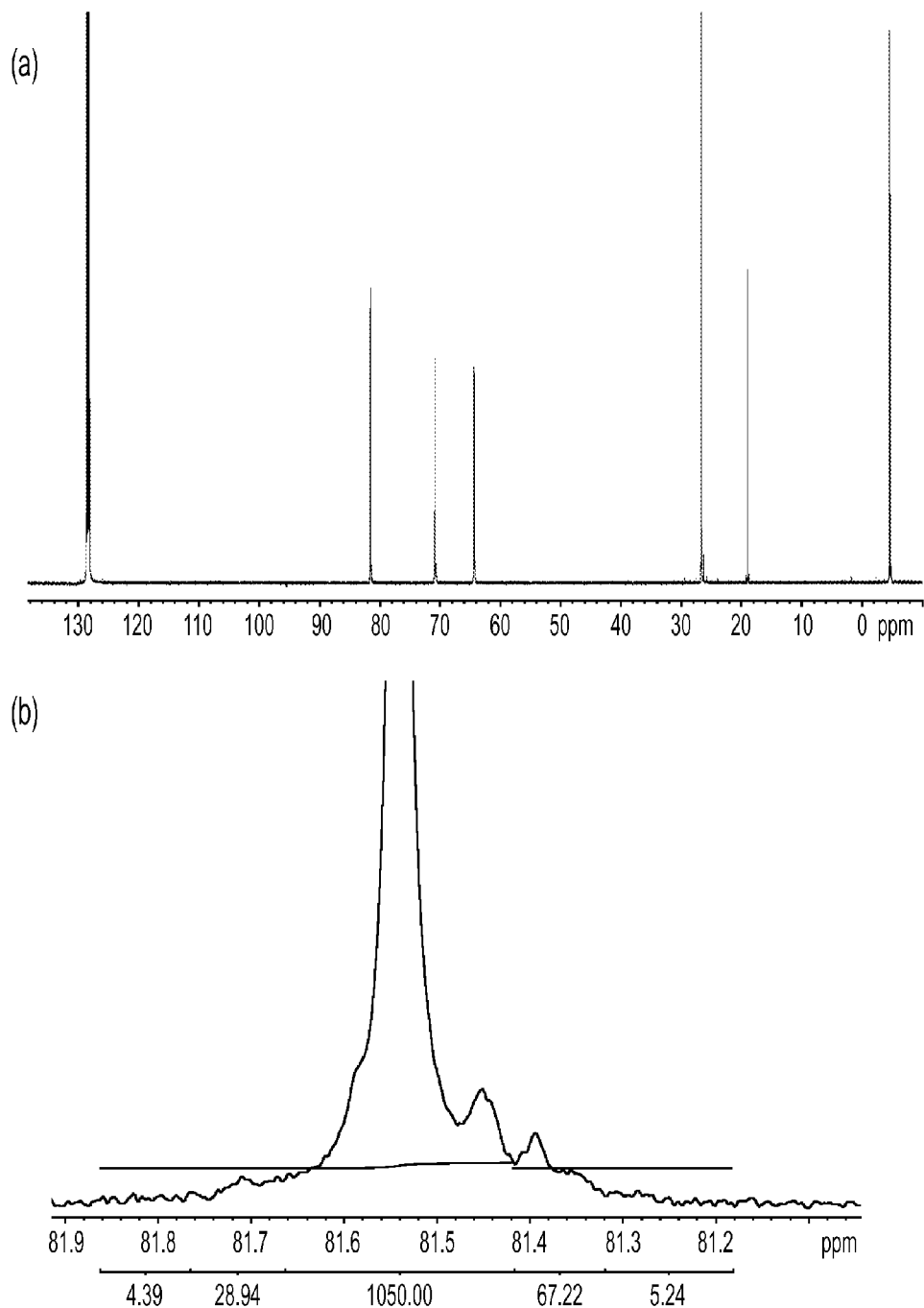
FIG. 21 depicts the $^{13}$C NMR spectra of Poly(tert-Butyldimethylsilyl Glycidyl Ether). a) Full spectrum. b) Methine carbon.

The polymerization procedure was the same as that for propylene oxide, except tert-butyl-dimethylsilyl glycidyl ether was used. Racemic catalyst solution (1.2 mg of racemic catalyst, 0.0011 mmol) and [PPN]OAc (1.3 mg, 0.0022 mmol) were added to a 4 mL vial containing a stir bar. tert-Butyl-dimethylsilyl glycidyl ether (0.2 g, 1.1 mmol), previously cooled to −24° C. in a freezer in the dry box, was added by syringe to the vial. Dry toluene (0.6 mL) was added to bring the concentration of tert-butyl-dimethylsilyl glycidyl ether to 1 M in toluene. Conversion was determined to be >99% to poly(tert-butyl-dimethylsilyl glycidyl ether) by $^1$H NMR analysis. The crude polymer solution was then concentrated under vacuum overnight. Polymer tacticity (FIG. 21): [mm]:[mr+nn]:[n]=[0.907]:[0.062]:[0.031]. %[mm] triad=90.7%.

$^{13}$C NMR (C$_6$D$_6$, 125 MHz): δ 81.54, 70.85, 64.37, 26.65, 18.98, −4.63.

$^1$H NMR (C$_6$D$_6$, 500 MHz): δ 3.92 (m, 1H), 3.85 (m, 3H), 3.68 (m, 1H), 1.07 (m, 9H), 0.19 (m, 6H).

M$_n$: 406,000
PDI: 1.5
T$_g$: −36° C. T$_m$: 30° C.

Synthesis of Poly(Phenyl Glycidyl Ether) (Table 2, Entry 8).

The polymerization procedure was the same as that for propylene oxide, except phenyl glycidyl ether was used.

Figure 22:
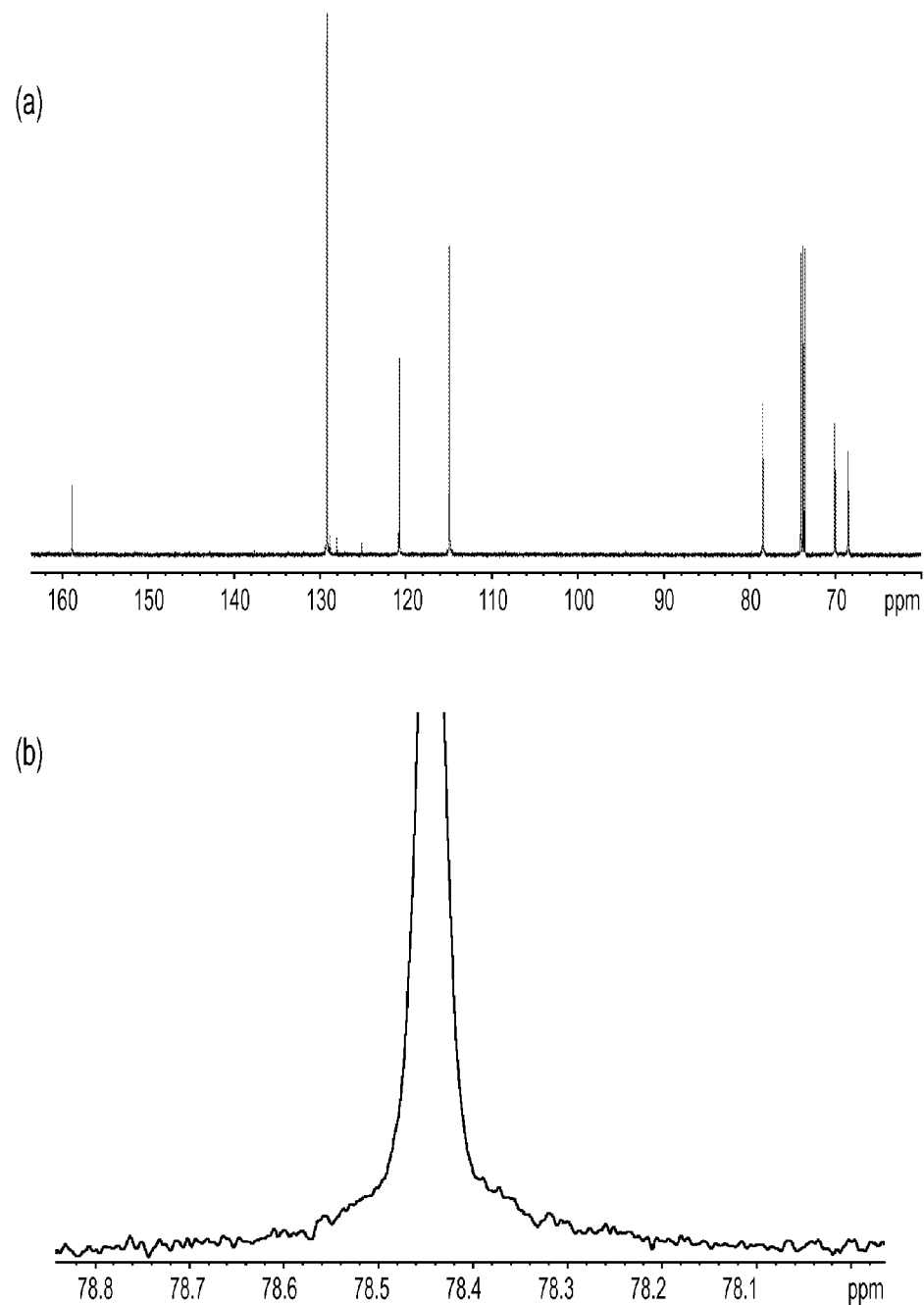
FIG. 22 depicts the $^{13}$C NMR spectra of Poly(Phenyl Glycidyl Ether). a) Full spectrum. b) Methine carbon.

Racemic catalyst solution (1.5 mg of racemic catalyst, 0.0013 mmol) and [PPN]OAc (1.6 mg, 0.0027 mmol) were added to a 4 mL vial containing a stir bar. Phenyl glycidyl ether was previously cooled to −24° C. in a freezer in the dry box. Phenyl glycidyl ether (0.2 g, 1.3 mmol) was added by syringe to the vial, and dry toluene (0.85 mL) was added to bring the concentration of phenyl glycidyl ether to 1M in toluene. Conversion was determined to be >99% to poly(phenyl glycidyl ether) by $^1$H NMR analysis. The crude polymer solution was then concentrated under vacuum overnight. Of note, the polymer was very insoluble in most solvents. NMR spectra were obtained in deuterated 1,1,2,2-tetrachloroethane at 120° C. Polymer tacticity (FIG. 22): % [mm] triad=>99%. Peaks corresponding to error in polymer stereoconfiguration ([mr], [rm], [rr]) were not detected by $^{13}$C NMR.

$^{13}$C NMR (1,1,2,2-tetrachloroethane-d$_2$, 125 MHz, 120° C.): δ 158.86, 129.19, 120.78, 114.94, 78.45, 70.05, 68.51.

$^1$H NMR (1,1,2,2-tetrachloroethane-d$_2$, 500 MHz, 120° C.): δ 7.19-7.26 (m, 2H), 6.86-6.96 (m, 3H), 4.09 (m, 1H), 4.03 (m, 1H), 3.74-3.88 (m, 3H).

M$_n$: 105,000
PDI: 1.5
T$_g$: 112° C. T$_m$: 193° C.

Synthesis of Poly(2,3-Epoxypropyl Benzoate) (Table 2, Entry 9).

Figure 23:
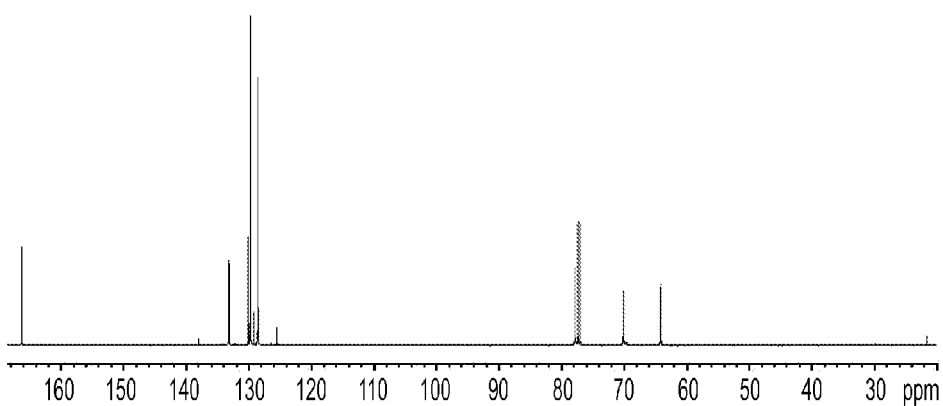
FIG. 23 depicts the $^{13}$C NMR spectra of Poly(2,3-epoxypropyl benzoate). a) Full spectrum. Note: peaks from residual toluene present in the spectrum. b) Methylene carbon.
Figure 23:
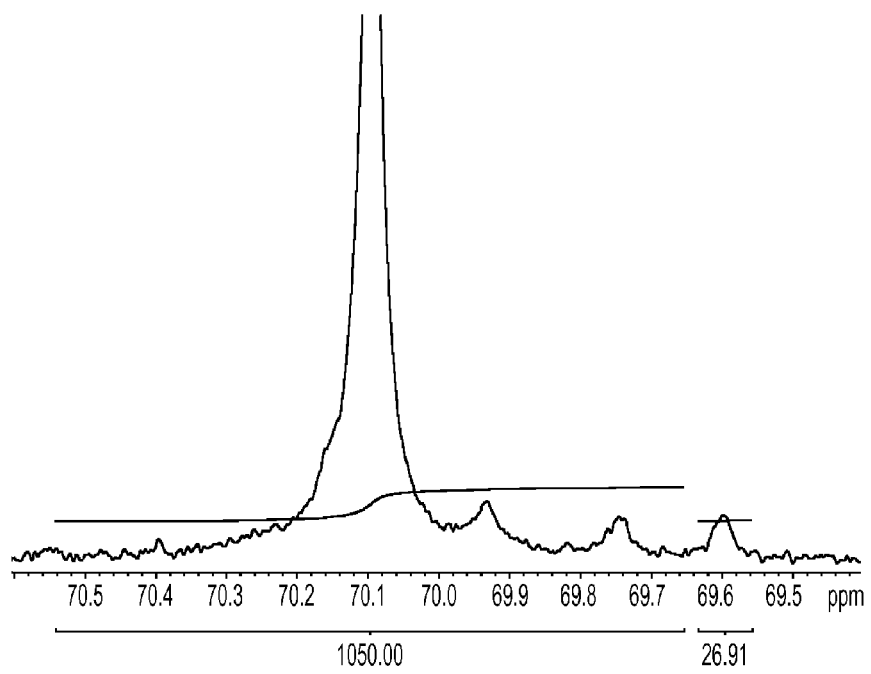

The polymerization procedure was the same as that for propylene oxide, except 2,3-epoxypropyl benzoate was used. Racemic catalyst solution (1.3 mg of racemic catalyst, 0.0011 mmol) and [PPN]OAc (1.3 mg, 0.0022 mmol) were added to a 4 mL vial containing a small stir bar. 2,3-Epoxypropyl benzoate (0.2 g, 1.1 mmol), previously cooled to −24° C. in a freezer in the dry box, was added by syringe to the vial. Dry toluene (0.8 mL) was added to bring the concentration of 2,3-epoxypropyl benzoate to 1 M in toluene. Conversion was determined to be >99% to poly(2,3-epoxypropyl benzoate) by
$^1$H NMR analysis. The crude polymer solution was then concentrated under vacuum overnight. Polymer tacticity (FIG. 23): [mm]:[mr+rm]:[rr]=[0.925]:[0.050]:[0.025]. %[mm] triad=92.5%. Note: residual toluene is present in the NMR spectrum.

$^{13}$C NMR (CDCl$_3$, 125 MHz): δ 166.28, 133.17, 130.06, 129.72, 128.55, 77.88, 70.09, 64.17.
(toluene: δ 137.84, 129.22, 128.41, 125.42, 21.55.)
$^1$H NMR (CDCl$_3$, 500 MHz): δ 7.84 (m, 2H), 7.33 (m, 1H), 7.22 (m, 2H), 4.31 (m, 1H), 4.17 (m, 1H), 3.60 (m, 3H).

M$_n$: 69,200
PDI: 1.5
T$_g$: 16° C.

Synthesis of Poly(Allyl Oxiran-2-ylmethyl Carbonate) (Table 2, Entry 10).

Figure 24:
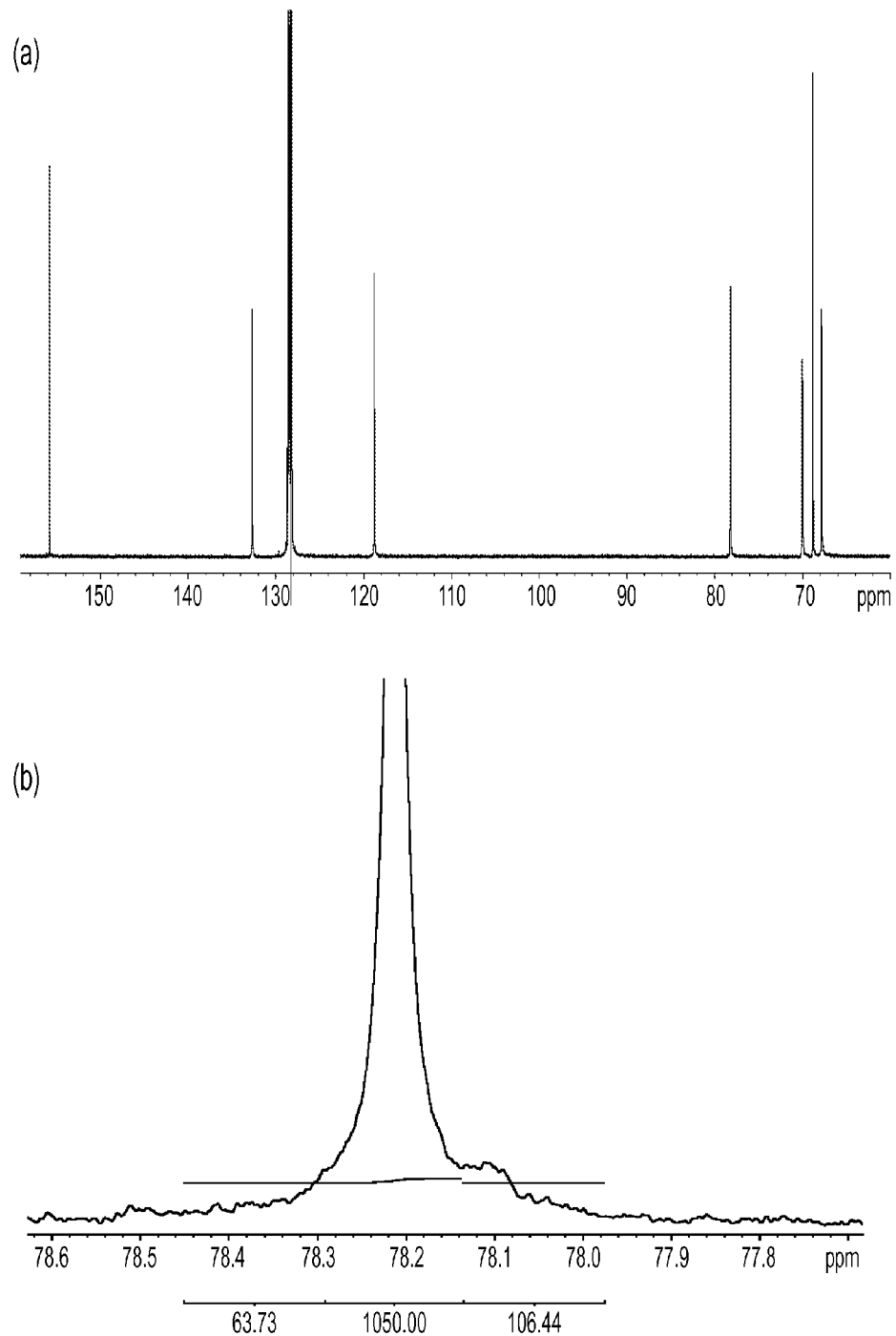
FIG. 24 depicts the $^{13}$C NMR spectra of Poly(Allyl Oxiran-2-ylmethyl Carbonate). a) Full spectrum. b) Methine carbon.

The polymerization procedure was the same as that for propylene oxide, except allyl oxiran-2-ylmethyl carbonate was used. Racemic catalyst solution (1.5 mg of racemic catalyst, 0.0013 mmol) and [PPN]OAc (1.5 mg, 0.0025 mmol) were added to a 4 mL vial containing a small stir bar. Allyl oxiran-2-ylmethyl carbonate (0.2 g, 1.3 mmol), previously cooled to −24° C. in a freezer in the dry box, was added by syringe to the vial. Dry toluene (0.9 mL) was added to bring the concentration of allyl oxirane-2-ylmethyl carbonate to 1 M in toluene. Conversion was determined to be >99% to poly(allyl oxirane-2-ylmethyl carbonate) by $^1$H NMR analysis. The crude polymer solution was then concentrated under vacuum overnight. Polymer tacticity (FIG. 24): [mm]:[mr+rm]:[rr]=[0.895]:[0.070]:[0.035]. %[mm] triad=89.5%.

$^{13}$C NMR (C$_6$D$_6$, 125 MHz): δ 155.80, 132.70, 118.79, 78.21, 70.0, 68.81, 67.83.

$^1$H NMR (C$_6$D$_6$, 500 MHz): δ 5.80 (ddt, J=17, 11, 5 Hz, 1H), 5.22 (dd, J=17.5, 1.5 Hz, 1H), 5.05 (m, 1H), 4.52 (d, J=5.5 Hz, 2H), 4.42 (dd, J=11, 2.5 Hz, 1H), 4.28 (dd, J=11, 5 Hz, 1H), 3.61 (m, 3H).

M$_n$: 65,000
PDI: 1.6
T$_g$: 17° C.

Synthesis of Poly(Styrene Oxide) (Table 2, Entry 11).

Figure 25:
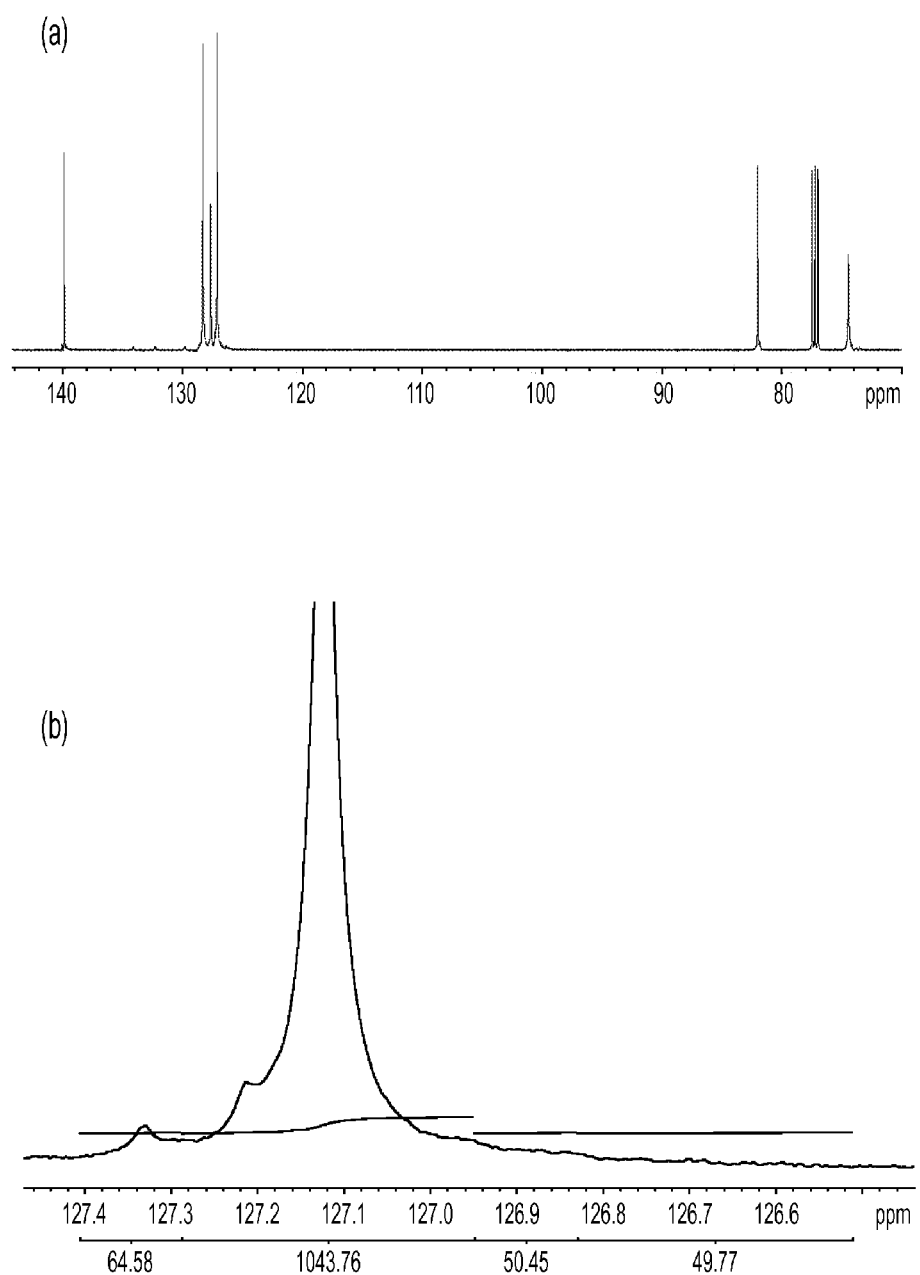
FIG. 25 depicts the $^{13}$C NMR spectra of Poly(Styrene Oxide). a) Full spectrum. b) Ortho carbon.

The polymerization procedure was the same as that for propylene oxide, except styrene oxide was used, and the polymerization was run in the presence of air. Racemic catalyst (4.0 mg, 0.0035 mmol) and [PPN]OAc (4.0 mg, 0.007 mmol) were added to a 4 mL vial containing a small stir bar. Styrene oxide (0.2 g, 1.7 mmol), previously cooled to −24° C. in a freezer in the dry box, was added by syringe to the vial. Dry toluene (0.63 mL) was added to make the concentration of styrene oxide 1 M in toluene. Conversion was determined to be >99% to poly(styrene oxide) by $^1$H NMR analysis. The crude polymer solution was then concentrated under vacuum overnight. Polymer tacticity (FIG. 25): [mm]:[mr+rm]:[rr]= [0.963]:[0.024]:[0.012]. %[mm] triad=96.3%. The $^{13}$C NMR ortho carbon resonance was used to determine the polymer tacticity due to better baseline resolution of the [rr] peak.

$^{13}$C NMR (CDCl$_3$, 125 MHz): δ 139.88, 128.32, 127.67, 127.12, 82.0, 74.44.

$^1$H NMR (CDCl$_3$, 500 MHz): δ 7.24-7.27 (m, 2H), 7.14-7.21 (m, 3H), 4.38 (dd, J=9, 4.5 Hz, 1H), 3.50 (dd, J=12.5, 10 Hz, 1H), 3.36 (dd, J=13.5, 5 Hz, 1H).

M$_n$: 97,700
PDI: 1.7
T$_g$: 49° C.

Synthesis of Poly(2-(4-Fluorophenyl)-oxirane) (Table 2, Entry 12).

Figure 26:
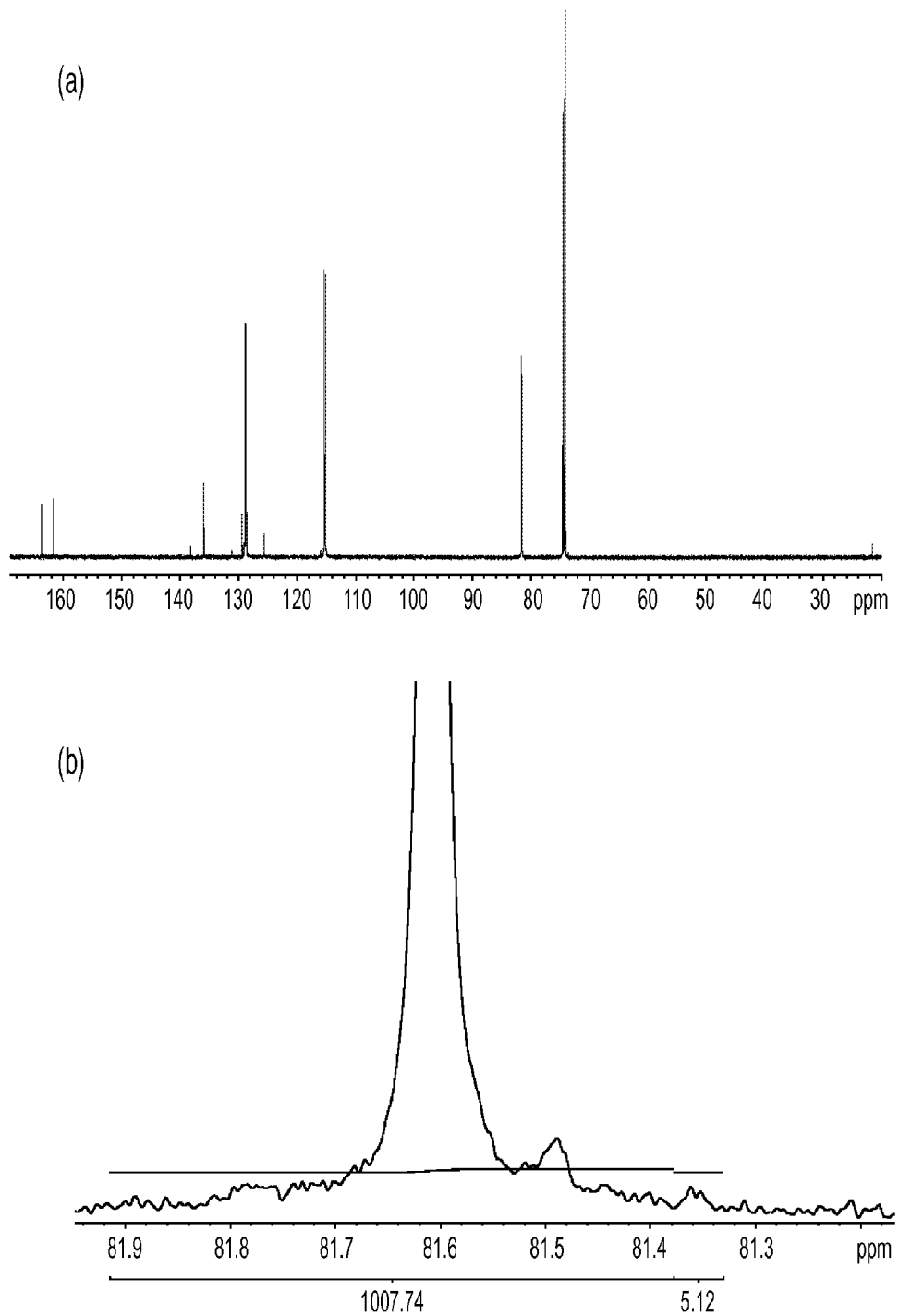
FIG. 26 depicts the $^{13}$C NMR spectra of Poly(2-(4-Fluorophenyl)-oxirane). a) Full spectrum. Note: residual toluene peaks present. b) Methine carbon.

The polymerization procedure was the same as that for propylene oxide, except 2-(4-fluorophenyl)-oxirane was used, and the polymerization was run in the presence of air. Racemic catalyst solution (1.7 mg of racemic catalyst, 0.0014 mmol) and [PPN]OAc (1.7 mg, 0.0028 mmol) were added to a 4 mL vial containing a stir bar. 2-(4-Fluorophenyl)-oxirane (0.2 g, 1.4 mmol), previously cooled to −24° C. in a freezer in the dry box, was added by syringe to the vial. Dry toluene (0.94 mL) was added to bring the concentration of 2-(4-fluorophenyl)-oxirane to 1 M in toluene. Conversion was determined to be >99% to poly(2-(4-fluorophenyl)-oxirane) by $^1$H NMR analysis. The crude polymer solution was then concentrated under vacuum overnight. NMR spectra were obtained in deuterated 1,1,2,2-tetrachloroethane at 120° C. Note: peaks due to residual toluene are present in the $^{13}$C NMR spectrum. Polymer tacticity (FIG. 26): [mm]:[mr+rm]: [rr]=[0.975]:[0.016]:[0.008]. %[mm] triad=97.5%.

$^{13}$C NMR (1,1,2,2-tetrachloroethane-d$_6$, 125 MHz, 120° C.): δ 163.14, 161.18, 135.37, 128.32 (d, J=31 Hz), 114.71 (d, J=85 Hz), 81.06.
(toluene: δ 137.63, 128.85, 128.02, 125.13, 21.08.)
$^1$H NMR (1,1,2,2-tetrachloroethane-d$_6$, 500 MHz): δ 7.12-7.19 (m, 2H), 6.91-7.0 (m, 2H), 4.30 (m, 1H), 3.50 (m, 1H), 3.39 (m, 1H).

M$_n$:120,000
PDI: 1.6
T$_g$: 50° C. T$_m$: 196° C.

Synthesis of Poly(1,1,1-Trifluoro-2,3-Epoxypropane) (Table 2, Entry 13).

Figure 27:
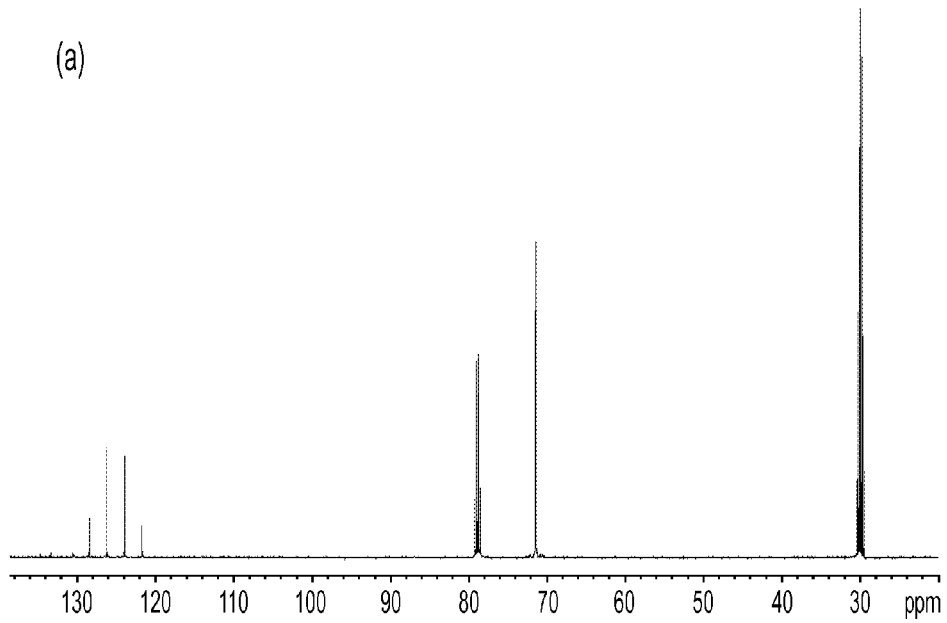
FIG. 27 depicts the $^{13}$C NMR spectra of Poly(1,1,1-Trifluoro-2,3-epoxypropane). a) Full spectrum. b) Methylene carbon.
Figure 27:
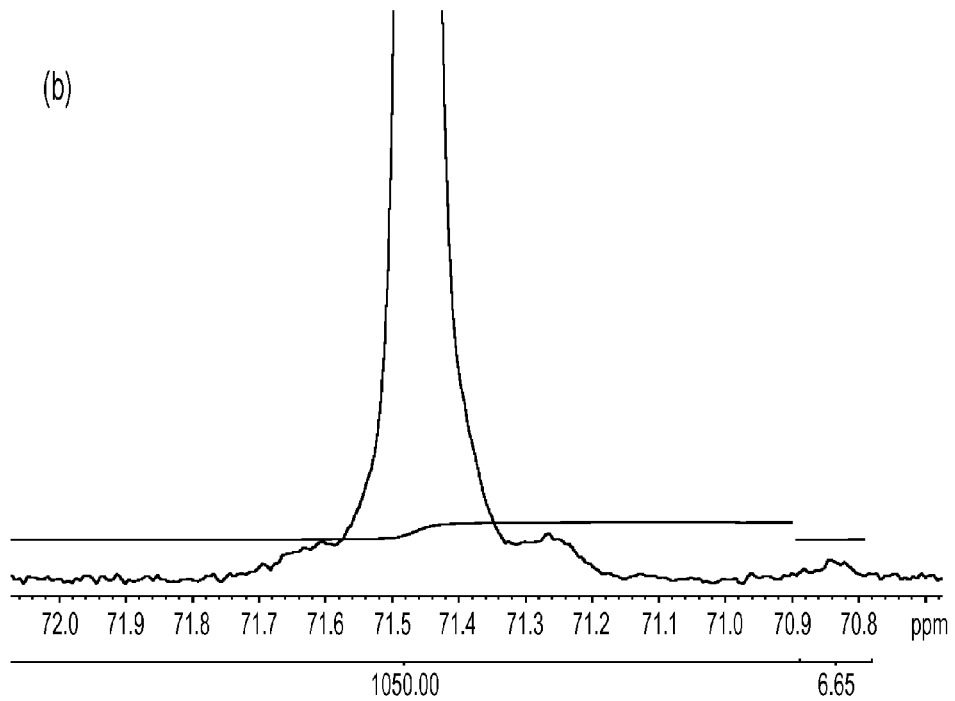

The polymerization procedure was the same as that for propylene oxide, except 1,1,1-trifluoro-2,3-epoxypropane was used. Racemic catalyst (5.2 mg, 0.0045 mmol) and [PPN] OAc (5.3 mg, 0.0089 mmol) were added to a 4 mL vial containing a stir bar. 1,1,1-Trifluoro-2,3-epoxypropane (0.5 g, 4.5 mmol), previously cooled to −24° C. in a freezer in the dry box, was added by syringe to the vial. Dry toluene (1.85 mL) was added to make the concentration of 1,1,1-trifluoro-2,3-epoxypropane 1 M in toluene. Conversion was determined to be >99% to poly(1,1,1-trifluoro-2,3-epoxypropane) by $^1$H NMR analysis. The crude polymer solution was then concentrated under vacuum overnight. NMR spectra were obtained in acetone-$d_6$. Polymer tacticity (FIG. 27): [mm]: [mr+rm]:[rr]=[0.981]:[0.013]:[0.006]. %[mm] triad=98.1%.

$^{13}$C NMR (Acetone-$d_6$, 125 MHz): δ 125.0 (quartet, J=2246, 1123 Hz, CF$_3$), 78.80 (quartet, J=237, 118 Hz, CHCF$_3$), 71.46.

$^1$H NMR (Acetone-$d_6$, 500 MHz): δ 4.32 (m, 1H), 4.18 (dd, J=11, 3 Hz, 1H), 4.02 (dd, J=11, 7 Hz, 1H).

$T_m$: 119° C.

A $T_g$ was not detected.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A bimetallic complex of formula I selected from the group consisting of formulas I-a, I-b, and I-c:

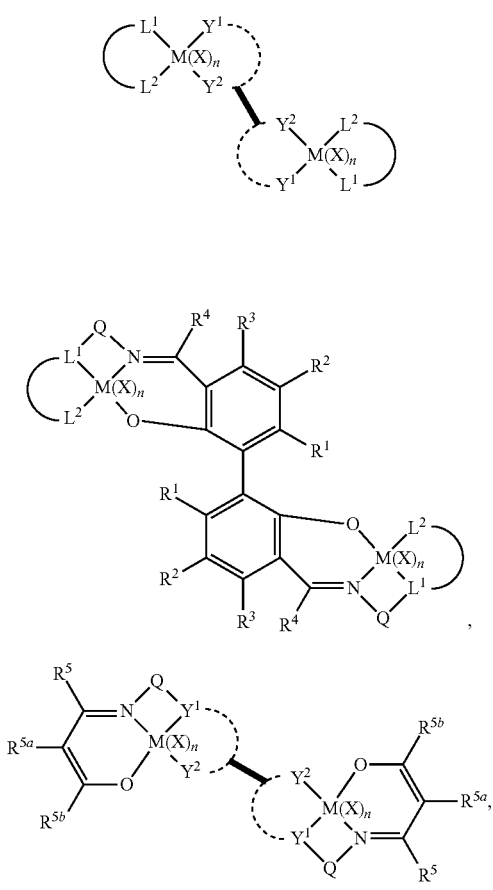

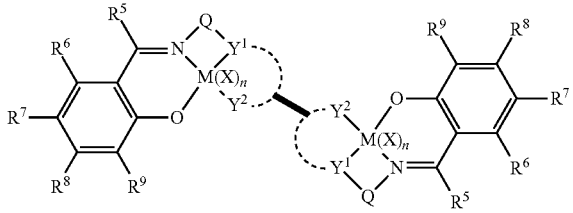

wherein:

M is a metal atom;

X is a nucleophile;

n is an integer from 0 to 2, inclusive each occurrence of L$^1$, L$^2$, Y$^1$, and Y$^2$ is independently —O—, —P(R')$_2$—, =NR'—, or —N(R')$_2$—;

each occurrence of

is an optionally substituted moiety selected from the group consisting of C$_{2-12}$ aliphatic, C$_{7-12}$ arylalkyl; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

each occurrence of

is an optionally substituted moiety selected from the group consisting of C$_{7-12}$ arylalkyl; 6-10-membered aryl; and 5-10-membered heteroaryl having 1-4 heteroatoms independently selected from nitrogen, oxygen, or sulfur;

\ represents a single bond directly attached to an aryl or heteroaryl ring of each

each occurrence of R' is hydrogen or an optionally substituted moiety selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)', —C(O)O—, —S—, —SO—, —SO$_2$—, —C(=S)—, —C(=NR$^y$)—, —C(=NOR$^y$)— or —N=N—; or two R' are taken together with their intervening atoms to form a monocyclic or bicyclic 5-12-membered ring;

wherein a substituent may comprise one or more organic cations;

each occurrence of Q is an optionally substituted moiety selected from the group consisting of a C$_3$-C$_{14}$ carbocycle, a C$_6$-C$_{10}$ aryl group, a C$_3$-C$_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —$OC(O)O$—, —O—, —$C(O)$—, —$OC(O)$—, —$C(O)O$—, —S—, —SO—, —$SO_2$—, —$C(=S)$—, —$C(=NR^y)$—, —$C(=NOR^y)$— or —N=N—;

each occurrence of $R^y$ is independently hydrogen or an optionally substituted $C_{1-6}$ aliphatic group;

each occurrence of $R^1$ and $R^2$ is independently hydrogen, halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^y$, —$OC(O)N(R^y)_2$, —$N(R^y)_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; or $R^1$ and $R^2$ are taken together with their intervening atoms to form an optionally substituted 4-14-membered carbocycle, an optionally substituted 4-14-membered heterocycle, an optionally substituted 6-10-membered aryl group or an optionally substituted 5-10-membered heteroaryl group having 1-4 heteroatoms independently selected from nitrogen, oxygen, or sulfur ring; and each occurrence of $R^3$ and $R^4$ is independently hydrogen, halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^y$, —$OC(O)N(R^y)_2$ —$N(R^y)_2$, —$NR^yC(O)R$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;

each occurrence of $R^5$, $R^{5a}$, and $R^{5b}$ is independently hydrogen, halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^y$, —$OC(O)N(R^y)_2$, —$N(R^y)_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; wherein adjacent $R^5$, $R^{5a}$, or $R^{5b}$ groups can be taken together to form an optionally substituted saturated, partially unsaturated, or aromatic 5- to 12-membered ring containing 0 to 4 heteroatoms;

each occurrence of $R^5$, $R^6$, $R^7$, $R^8$, and $R^9$ is independently hydrogen, halogen, —$NO_2$, —CN, —$SR^y$, —$S(O)R^y$, —$S(O)_2R^y$, —$NR^yC(O)R^y$, —$OC(O)R^y$, —$CO_2R^y$, —NCO, —$N_3$, —$OR^y$, —$OC(O)N(R^y)_2$, —$N(R^y)_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; wherein adjacent $R^6$, $R^7$, $R^8$, or $R^9$ groups can be taken together to form an optionally substituted saturated, partially unsaturated, or aromatic 5- to 12-membered ring containing 0 to 4 heteroatoms; and each occurrence of $R^y$ is independently hydrogen or an optionally substituted $C_{1-6}$ aliphatic group.

2. The bimetallic complex of claim 1, wherein the complex is of formula I-a:

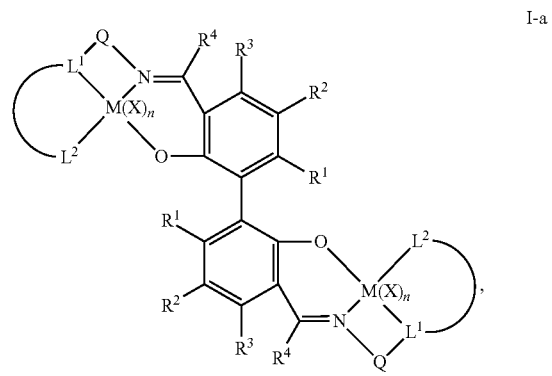

I-a

3. The bimetallic complex of claim 1, wherein the complex is of formula I-b:

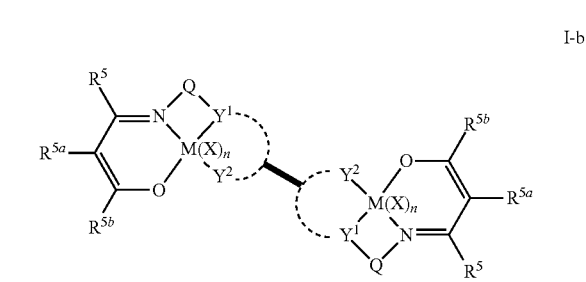

I-b

4. The bimetallic complex of claim 1, wherein the complex is of formula I-c:

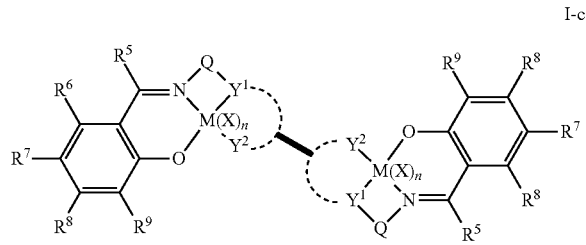

I-c

5. The bimetallic complex of claim 1, wherein the complex is of formula II:

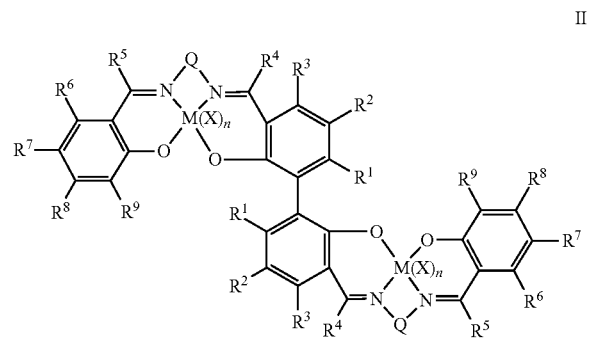

6. The bimetallic complex of claim 5, wherein M is selected from the group consisting of a transition metal from group 5-12, boron and aluminum.

7. The bimetallic complex of claim 6, wherein M is selected from the group consisting of Cr, Mn, V, Fe, Co, Mo, W, Ru, Ti, Al, Zr, Hf, and Ni.

8. The bimetallic complex of claim 7, wherein M is Co.

9. The bimetallic complex of claim 5, wherein Q is optionally substituted $C_{5-10}$ aliphatic.

10. The bimetallic complex of claim 5, wherein Q is optionally substituted 1,2-cyclohexyl.

11. The bimetallic complex of claim 10, wherein Q is (R,R)-1,2-cyclohexyl when the bond between the biaryl linkage is of S chirality.

12. The bimetallic complex of claim 10, wherein Q is (S,S)-1,2-cyclohexyl when the bond between the biaryl linkage is of R chirality.

13. The bimetallic complex of claim 5, wherein $R^1$ and $R^2$ are taken together with their intervening atoms to form a 6-membered aryl ring.

14. The bimetallic complex of claim 13, wherein $R^1$ and $R^2$ are taken together with their intervening atoms to form:

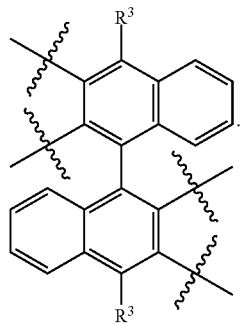

15. The bimetallic complex of claim 5, wherein $R^1$ and $R^2$ are taken together with their intervening atoms to form:

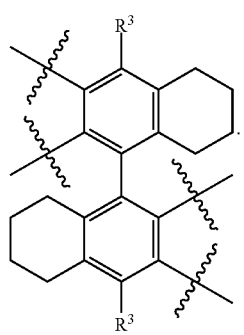

16. The bimetallic complex of claim 5, wherein each of $R^3$, $R^4$, $R^5$, $R^6$, and $R^8$ is hydrogen.

17. The bimetallic complex of claim 5, wherein each of $R^3$, $R^4$, $R^5$, $R^6$, $R^7$, $R^8$, and $R^9$ is hydrogen.

18. The bimetallic complex of claim 5, wherein one or more of $R^3$, $R^4$, $R^5$, $R^6$, $R^7$, $R^8$, and $R^9$ is substituted with an organic cation.

19. The bimetallic complex of claim 18, wherein the organic cation is a quaternary ammonium group.

20. The bimetallic complex of claim 5, wherein $R^7$ and $R^9$ are independently optionally substituted groups selected from the group consisting of $C_{1-12}$ aliphatic and $C_{1-12}$ heteroaliphatic having 1-4 heteroatoms independently selected from the group consisting of nitrogen, oxygen, and sulfur.

21. The bimetallic complex of claim 20, wherein $R^7$ and $R^9$ are independently an optionally substituted $C_{1-6}$ aliphatic group.

22. The bimetallic complex of claim 21, wherein $R^7$ and $R^9$ are t-butyl.

23. The bimetallic complex of claim 5, wherein the complex is racemic.

24. The bimetallic complex of claim 5, wherein the complex is non-racemic.

25. The bimetallic complex of claim 8, wherein the complex possesses axial symmetry.

26. The bimetallic complex of claim 5, wherein the complex is of formula II-a:

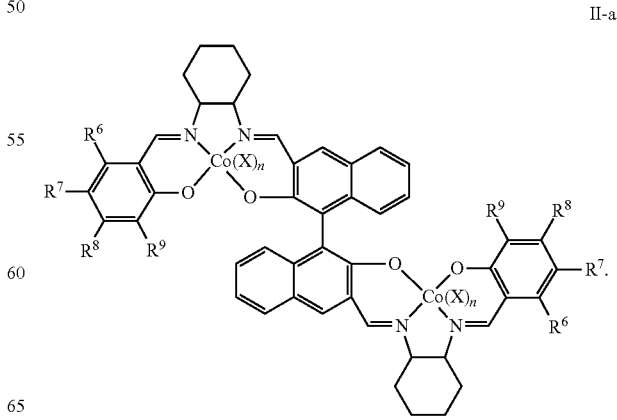

27. The bimetallic complex of claim 26, wherein the complex is of formula II-b:
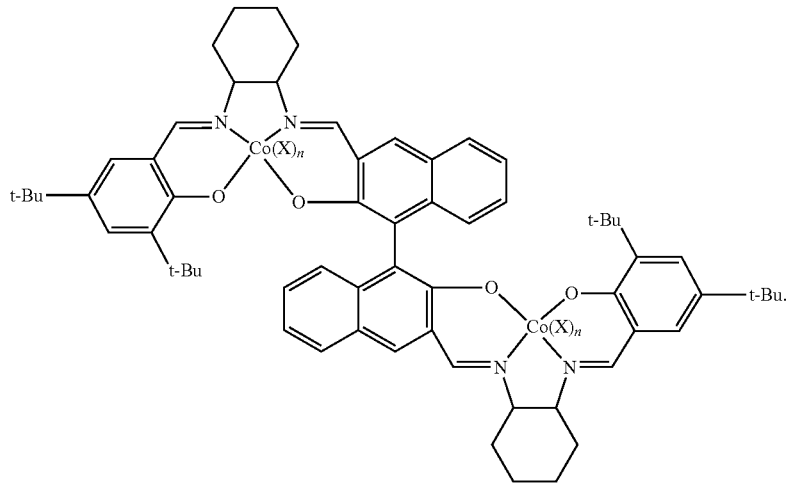
II-b
28. The bimetallic complex of claim 26, wherein the complex is selected from:
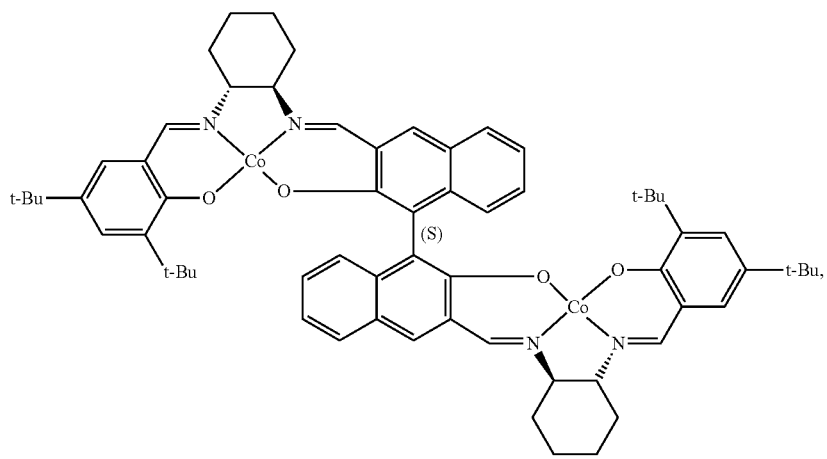
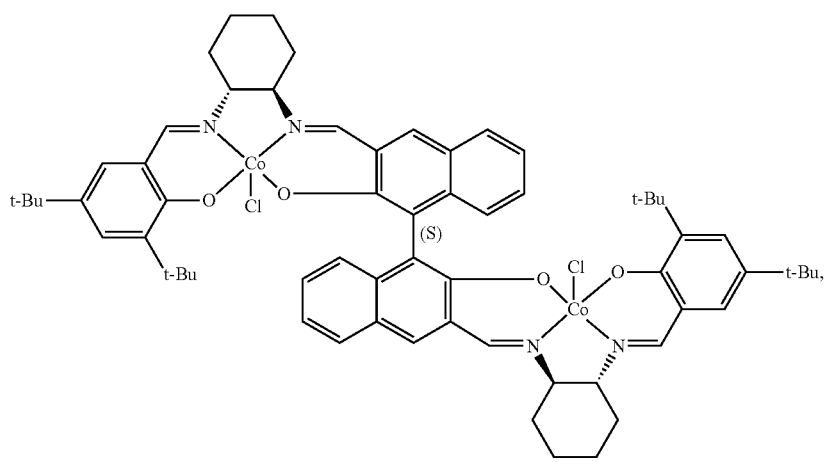

-continued
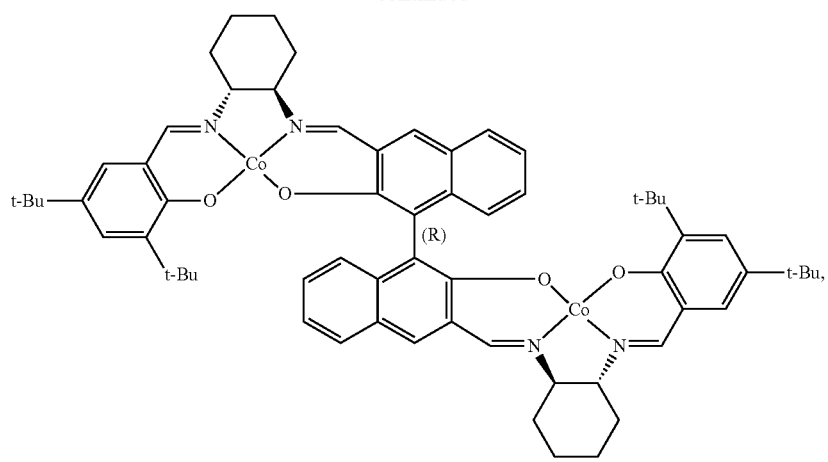
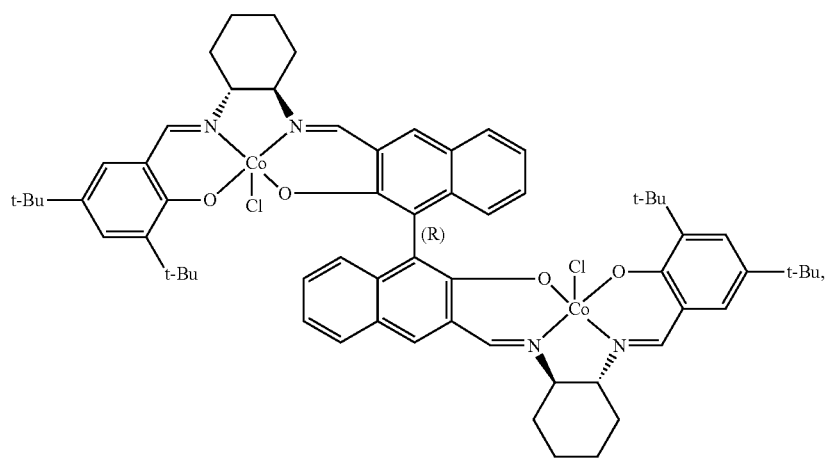
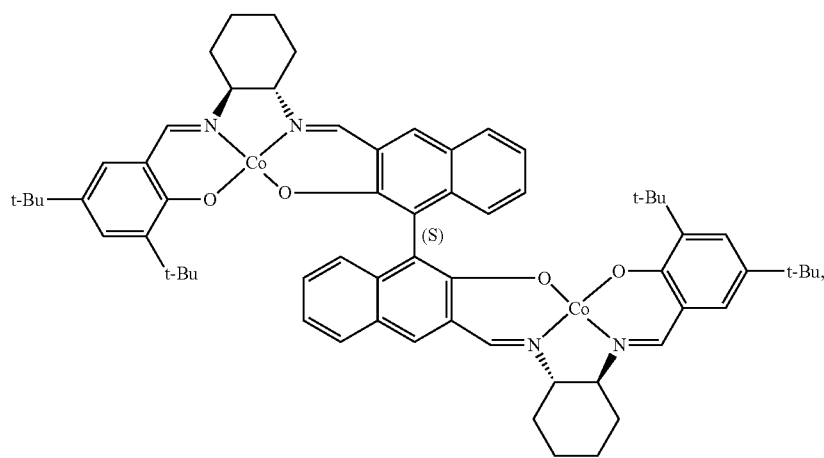

-continued
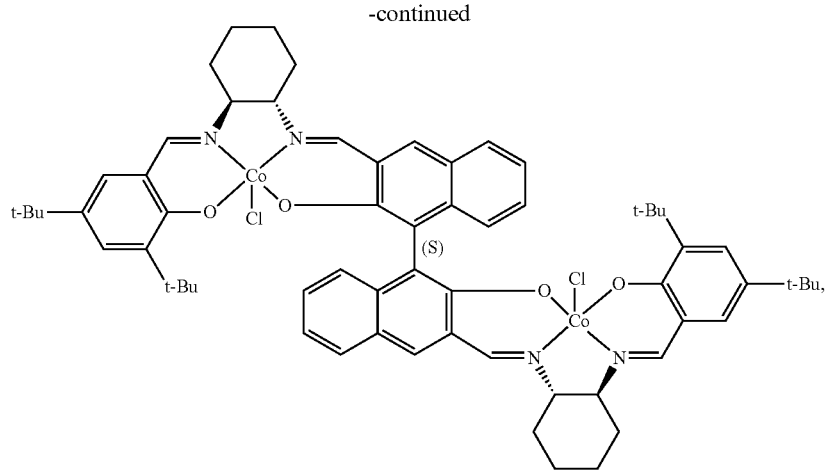
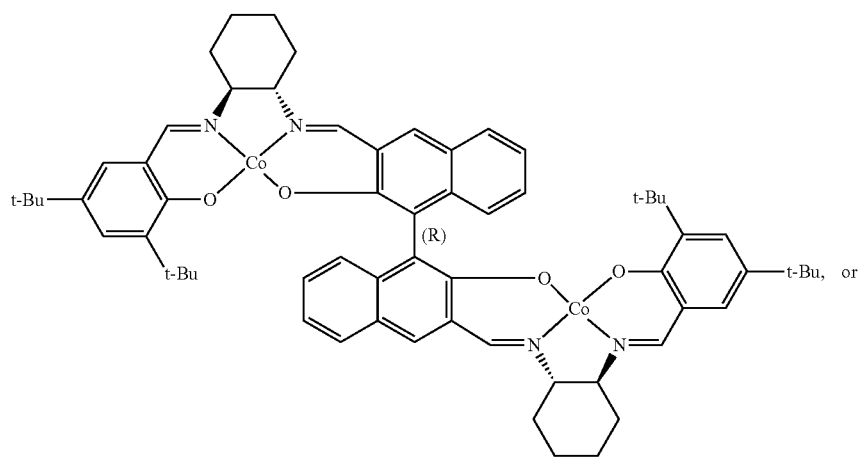
or
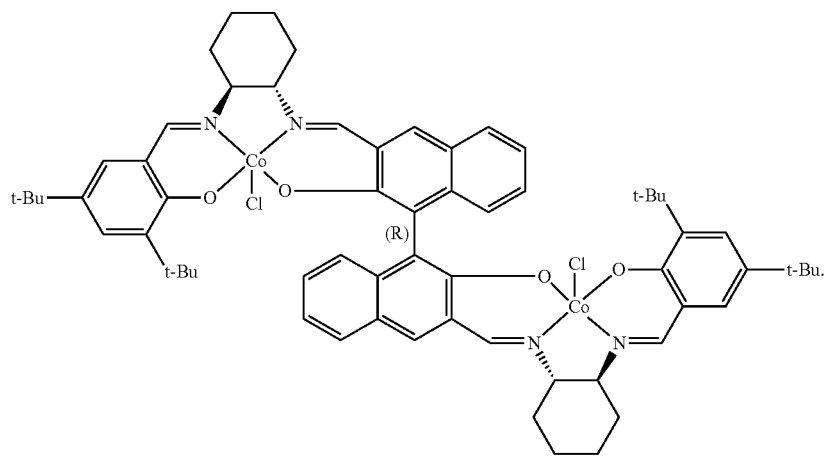

29. The bimetallic complex of claim 5, wherein the complex is of formula II-c:

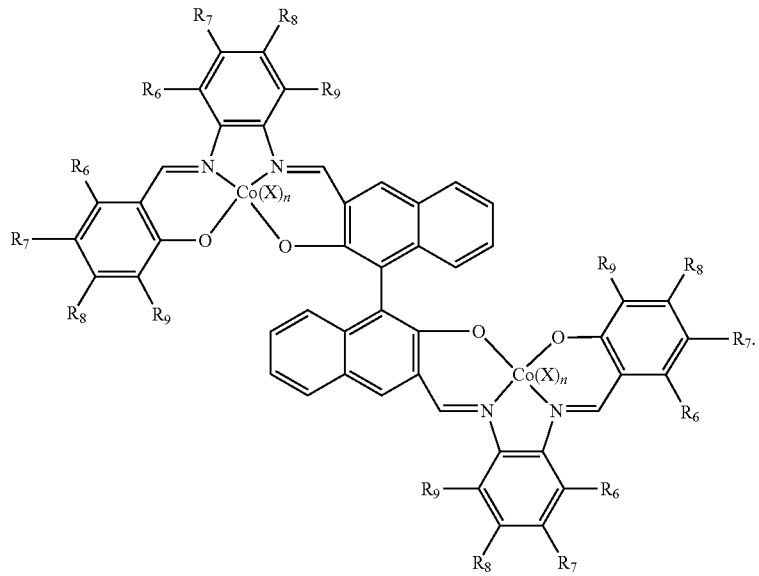

30. A method of polymerization, the method comprising:
a) providing a prochiral epoxide of formula:

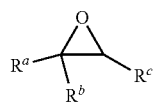

wherein:
- $R^a$ is an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; and
- each of $R^b$ and $R^c$ is independently hydrogen or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur;
- wherein any of ($R^a$ and $R^c$), ($R^b$ and $R^c$), and ($R^a$ and $R^b$) can be taken together with their intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted $C_5$-$C_{10}$ heteroaryl; and b) contacting the epoxide with the bimetallic complex of claim 1 to form a polymer of formula:

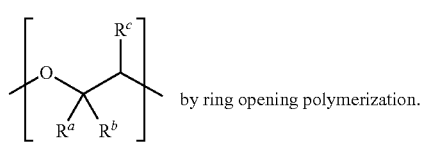

by ring opening polymerization.

31. The method of claim 30, further comprising a step, after step (a), of adding at least one additional epoxide having the formula

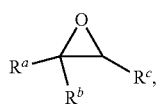

wherein each of the additional epoxide has a structure different from the structure of the epoxide provided in step (a) such that the polymer formed in step (b) is a co-polymer of two or more epoxides.

32. The method of claim 30, wherein the bimetallic complex of claim 1 is of formula II:

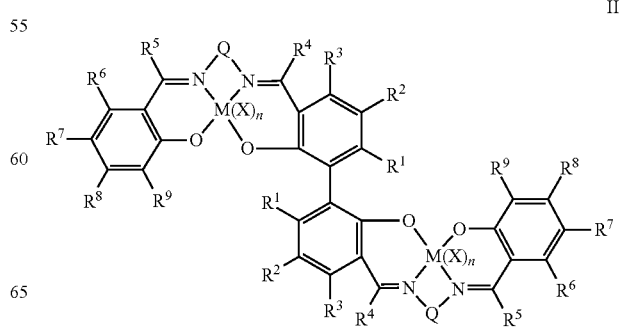

wherein:

M is a main group metal;

each occurrence of Q is an optionally substituted moiety selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —$OC(O)O$—, —$O$—, —$C(O)$—, —$OC(O)$—, —$C(O)O$—, —$S$—, —$SO$—, —$SO_2$—, —$C(=S)$—, —$C(=NR^y)$—, —$C(=NOR^y)$— or —$N=N$—;

each occurrence of $R^y$ is independently hydrogen or an optionally substituted $C_{1-6}$ aliphatic group;

each occurrence of $R^1$ and $R^2$ is independently hydrogen, halogen, —$NO_2$, —$CN$, —$SR^y$, —$S(O)R^y$, —$S(O)_2R^y$, —$NR^yC(O)R^y$, —$OC(O)R^y$, —$CO_2R^y$, —$NCO$, —$N_3$, —$OR^y$, —$OC(O)N(R^y)_2$, —$N(R^y)_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; or $R^1$ and $R^2$ are taken together with their intervening atoms to form an optionally substituted 4-14-membered carbocycle, an optionally substituted 4-14-membered heterocycle, an optionally substituted 6-10-membered aryl group or an optionally substituted 5-10-membered heteroaryl group having 1-4 heteroatoms independently selected from nitrogen, oxygen, or sulfur ring; and each occurrence of $R^3$, $R^4$, $R^5$, $R^6$, $R^7$, $R^8$, and $R^9$ is independently hydrogen, halogen, —$NO_2$, —$CN$, —$SR^y$, —$S(O)R^y$, —$S(O)_2R^y$, —$NR^yC(O)R^y$, —$OC(O)R^y$, —$CO_2R^y$, —$NCO$, —$N_3$, —$OR^y$, —$OC(O)N(R^y)_2$, —$N(R^y)_2$, —$NR^yC(O)R^y$, —$NR^yC(O)OR^y$; or an optionally substituted group selected from the group consisting of $C_{1-12}$ aliphatic; $C_{1-12}$ heteroaliphatic having 1-4 heteroatoms independently selected from the group consisting of nitrogen, oxygen, and sulfur; 6-10-membered aryl; 5-10-membered heteroaryl having 1-4 heteroatoms independently selected from nitrogen, oxygen, or sulfur; and 4-7-membered heterocyclic having 1-2 heteroatoms independently selected from the group consisting of nitrogen, oxygen, and sulfur; wherein adjacent $R^6$, $R^7$, $R^8$, or $R^9$ groups can be taken together to form an optionally substituted saturated, partially unsaturated, or aromatic 5- to 12-membered ring containing 0 to 4 heteroatoms.

33. The method of claim 30, wherein the epoxide is contacted with the bimetallic complex in the presence of comprise one or more co-catalysts.

34. The method of claim 33, wherein the co-catalyst is selected from the group consisting of an amine, a phosphonium salt, an ammonium salt, an arsonium salt, and a combination of any two or more of the above.

35. The method of claim 33, wherein the co-catalyst is PPN—X, where X is a nucleophile.

36. The method of claim 35, wherein the co-catalyst is PPNOAc.

37. The method of claim 32, wherein the enantiomeric excess of the polymer is greater than 90%.

38. The method of claim 32, wherein the enantiomeric excess of the polymer is greater than 95%.

39. The method of claim 32, wherein the enantiomeric excess of the polymer is greater than 97%.

40. The method of claim 32, wherein the enantiomeric excess of the polymer is greater than 98%.

41. The method of claim 32, wherein the enantiomeric excess of the polymer is greater than 99%.

42. The method of claim 32, wherein the polymerization is enantioselective.

43. The method of claim 32, wherein the method is a kinetic resolution.

44. The method of claim 32, wherein the polymerization is living.

45. The method of claim 42, further comprising the step of recovering unreacted epoxide, wherein the recovered epoxide is enantiomerically enriched.

46. The method of claim 45, wherein the enantiomeric excess of the recovered epoxide is greater than 90%.

47. The method of claim 45, wherein the enantiomeric excess of the recovered epoxide is greater than 95%.

* * * * *